United States Patent [19]

Petersen et al.

[11] Patent Number: 5,607,942
[45] Date of Patent: Mar. 4, 1997

[54] 7-(1-PYRROLIDINYL)-3-QUINOLONE- AND -NAPHTHYRIDONE-CARBOXYLIC ACID DERIVATIVES AS ANTIBACTERIAL AGENTS AND FEED ADDITIVES

[75] Inventors: Uwe Petersen, Leverkusen; Thomas Schenke, Bergisch-Gladbach; Andreas Krebs, Odenthal-Holz; Klaus Grohe; Michael Schriewer, both of Odenthal; Ingo Haller, Wuppertal; Karl G. Metzger, Wuppertal; Rainer Endermann, Wuppertal; Hans-Joachim Zeiler, Velbert, all of Germany

[73] Assignee: Bayer Aktiengesellschaft, Leverkusen, Germany

[21] Appl. No.: 406,448

[22] Filed: Mar. 20, 1995

Related U.S. Application Data

[62] Division of Ser. No. 737,631, Jul. 30, 1991, Pat. No. 5,416,096, which is a division of Ser. No. 580,906, Sep. 10, 1990, Pat. No. 5,059,597, which is a division of Ser. No. 375,434, Jun. 30, 1989, Pat. No. 4,990,517.

[30] Foreign Application Priority Data

Jul. 15, 1988 [DE] Germany .......................... 38 24 072.6
Mar. 1, 1989 [DE] Germany .......................... 39 06 365.8

[51] Int. Cl.⁶ ...................... A61K 31/47; C07D 471/04
[52] U.S. Cl. ............................... 546/200; 546/113
[58] Field of Search ............................. 546/113; 514/300

[56] References Cited

U.S. PATENT DOCUMENTS

| | | | |
|---|---|---|---|
| 4,698,350 | 10/1987 | Daum et al. | 514/312 |
| 4,771,055 | 9/1988 | Domagala et al. | 514/312 |
| 4,859,776 | 8/1989 | Chu et al. | 546/123 |
| 4,889,857 | 12/1989 | Araki et al. | 514/235.2 |
| 4,990,517 | 2/1991 | Petersen et al. | 514/300 |
| 5,043,156 | 8/1991 | Matsumoto et al. | 424/85.1 |
| 5,075,319 | 12/1991 | Lesher et al. | 514/312 |
| 5,457,104 | 10/1995 | Bartel et al. | 514/234.5 |

FOREIGN PATENT DOCUMENTS

| | | |
|---|---|---|
| 0106489 | 4/1984 | European Pat. Off. |
| 0241206 | 10/1987 | European Pat. Off. |

OTHER PUBLICATIONS

Horst Spielmann et al, Erste ergebnisse der Validierung von in vitro Phototoxizitatstests im Rahmen eines EG/COLIPA Projektes, ALTEX Jan. 1994, 22–31.
Sparfloxacin Monograph Adis, 35–39 (1994).
James H. Paton et al, Clinical Features and Management of Adverse Effects of Quinolone Antibacterials, Drug Safety, 6 1991, pp. 9–27.
John M. Domagala, Quinolone activity and side–effect relationships, Journal of Antimicrobial Chemotherapy (1994) 33, 685–706.

(List continued on next page.)

*Primary Examiner*—Richard L. Raymond
*Attorney, Agent, or Firm*—Sprung Horn Kramer & Woods

[57] ABSTRACT 7-(1-Pyrrolidinyl)-3-quinolone- and -naphthyridone-carboxylic acid derivatives as antibacterial agents and feed additives, of the formula

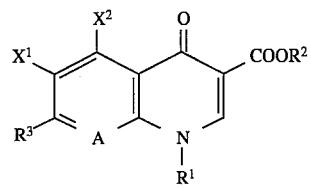

in which $X^1$ is halogen, $X^2$ is hydrogen, halogen, amino or other radical, $R^1$ is alkyl, cycloalkyl, optionally substituted phenyl or other radical, $R^2$ is hydrogen, alkyl or a dioxolylmethyl radical, $R^3$ is

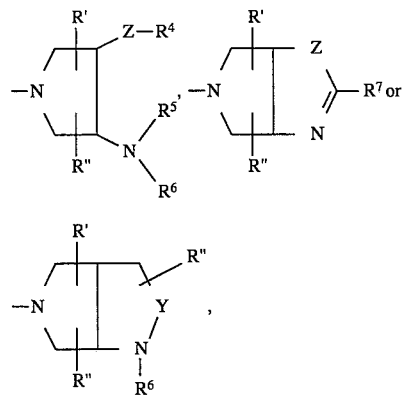

and A is N, CH, C-halogen, or the like, or forms a bridge with $R^1$,
and addition products thereof.

8 Claims, No Drawings

OTHER PUBLICATIONS

Emad Rizk, A worldwide clinical overview of lomefloxacin, a once-daily fluoroquinolone, International Journal of Antimicrobial Agents, 2 (1992), 67–78.

M. Amdur et al., *Casarett and Doull's Toxicology: The Basic Science of Poisons* 4th ed., McGraw–Hill, Inc., New York, 1993, pp. 33 and 476–477.

M. Furukawa et al., *Iyakuhin Kenkyu,* 21(5), pp. 989–97 (1990).

Chemical Abstracts, vol. 4, 1986, p. 521, No. 50861t, Dainippon.

Chemical Abstracts, vol. 111, 1989, p. 742, No. 97210q, Iwata.

Chemical Abstracts, vol. 111, 1989, p. 721, No. 153779w, Chiba.

Egawa et al Journal of Medicinal Chemistry, vol. 27, No. 12, Dec. 1984 pp. 1543–1549.

Liebig's Ann. der Chemie, vol. 677 (1964) p. 155, Birkofer.

7-(1-PYRROLIDINYL)-3-QUINOLONE- AND -NAPHTHYRIDONE-CARBOXYLIC ACID DERIVATIVES AS ANTIBACTERIAL AGENTS AND FEED ADDITIVES

This application is a divisional of application Ser. No. 07/737,631, filed Jul. 30, 1991, now U.S. Pat. No. 5,416,096, which is a divisional of application Ser. No. 07/580,906, filed on Sep. 10, 1990, now Pat. No. 5,059,597, which is a division of application Ser. No. 07/375,434, filed Jun. 30, 1979, now Pat. No. 4,990,517.

The invention relates to new 7-(1-pyrrolidinyl)-3-quinolone- and naphthyridonecarboxylic acid derivatives, processes for their preparation and antibacterial agents and feed additives containing them.

A number of 3-quinolone- and naphthyridonecarboxylic acids which are substituted in the 7-position by a pyrrolidinyl ring have already been disclosed. German Patent Application 3,318,145 and European Patent Applications 106,489 and 153,826.

It has been found that the 7-(1-pyrrolidinyl)-3-quinolone- and naphthyridonecarboxylic acid derivatives of the formula (I)

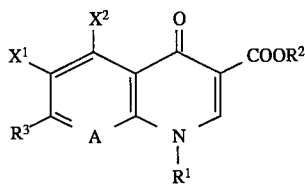

in which
$X^1$ represents halogen,
$X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio or halogen,
$R^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino or phenyl which is optionally substituted by 1 or 2 fluorine atoms,
$R^2$ represents hydrogen, alkyl having 1 to 4 carbon atoms or (5-methyl-2-oxo-1,3-dioxol-4-yl)-methyl,
$R^3$ represents a radical of the structure

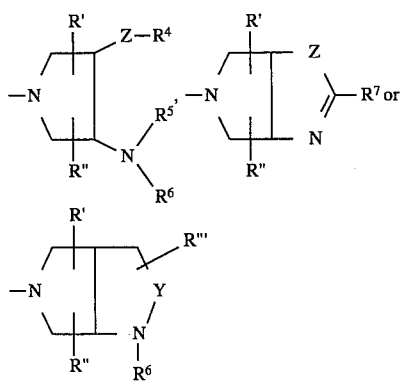

wherein
$R^4$ can represent H, $C_1-C_4$-alkyl, aryl or $C_1-C_4$-acyl,
$R^5$ can represent H, $C_1-C_4$-alkyl, OH or $OCH_3$, it also being possible for $R^4$ and $R^5$ together to denote a $C_1-C_3$-alkylene bridge which is optionally mono- or disubstituted by methyl, $R^6$ can represent H, optionally hydroxyl-substituted $C_1-C_4$-alkyl, as well as aryl, heteroaryl, benzyl, $C_1-C_4$-alkoxycarbonyl, $C_1-C_4$-acyl, (5-methyl-2-oxo-1,3-dioxol-4-yl)-methyl, or $C_3-C_6$-cycloalkyl,
$R^7$ can represent H or $C_1-C_4$-alkyl,
R' can represent H, $CH_3$ or phenyl,
R" can represent H, $CH_3$ or phenyl,
R'" can represent H or $CH_3$,
Y can represent O, $CH_2$, $CH_2CH_2$ or $CH_2$—O, it being possible for the $CH_2$—O group to be linked to the nitrogen either via or via $CH_2$, and
Z can represent O or S, and
A represents N or C—$R^8$, wherein
$R^8$ represents H, halogen, methyl, cyano, nitro, hydroxyl or methoxy or, together with $R^1$, can form a bridge having the structure

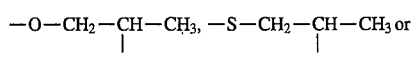

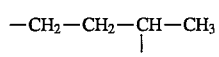

and pharmaceutically usable hydrates and acid addition salts thereof and the alkali metal, alkaline earth metal, silver and guanidinium salts of the underlying carboxylic acids, have a high antibacterial action, in particular in the Gram-positive region.

Preferred compounds are those of the formula (I)

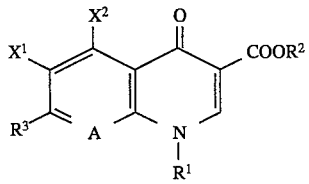

in which
$X^1$ represents fluorine or chlorine,
$X^2$ represents hydrogen, amino, alkylamino having 1 or 2 carbon atoms, dimethylamino, hydroxyl, methoxy, mercapto, methylthio, phenylthio, fluorine or chlorine,
$R^1$ represents alkyl having 1 to 3 carbon atoms, alkenyl having 2 or 3 carbon atoms, cycloalkyl having 3 to 5 carbon atoms, 2-hydroxyethyl, 2-fluoroethyl, methoxy, amino, methylamino, ethylamino, dimethylamino or phenyl which is optionally substituted by 1 or 2 fluorine atoms,
$R^2$ represents hydrogen, alkyl having 1 to 3 carbon atoms or (5-methyl-2-oxo-1,3-dioxol-4-yl)-methyl,
$R^3$ represents a radical having the structure

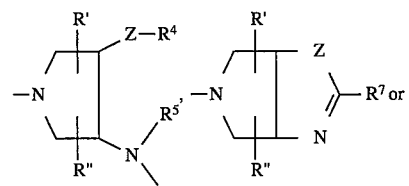

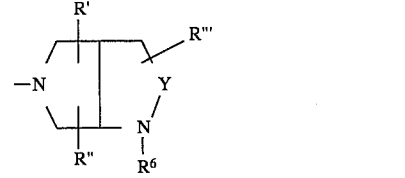

wherein $R^4$ can represent H, $C_1$–$C_3$-alkyl or $C_1$–$C_2$-acyl, $R^5$ can represent H, $C_1$–$C_3$-alkyl, OH or $OCH_3$, it also being possible for $R^4$ and $R^5$ together to denote a $C_1$–$C_2$-alkylene bridge which is optionally mono- or disubstituted by methyl, $R^6$ can represent H, optionally hydroxyl-substituted $C_1$–$C_3$-alkyl, as well as phenyl, benzyl, $C_1$–$C_4$-alkoxycarbonyl, $C_1$–$C_2$-acyl, (5-methyl-2-oxo-1,3-dioxol-4-yl)-methyl, or $C_3$–$C_5$-cycloalkyl, $R^7$ can represent H or $C_1$–$C_2$-alkyl, R' can represent H or $CH_3$, R" can represent H or $CH_3$, R''' can represent H or $CH_3$, Y can represent O, $CH_2$, $CH_2$, $CH_2CH_2$ or $CH_2$—O, it being possible for the $CH_2$—O group to be linked the nitrogen either via O or via $CH_2$, and Z can represent O or S, and A represents N or C—$R^8$, wherein $R^8$ represents H, fluorine, chlorine, bromine, methyl, nitro, hydroxyl or methoxy or together with $R^1$ can form a bridge having the structure

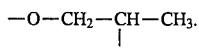

Particularly preferred compounds are those of the formula (I)

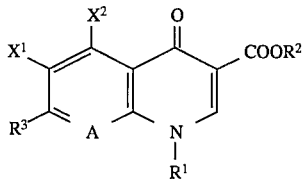

in which $X^1$ represents fluorine, $X^2$ represents hydrogen, amino, methylamino or fluorine, $R^1$ represents alkyl having 1 or 2 carbon atoms, vinyl, cyclopropyl, 2-hydroxyethyl, 2-fluoroethyl, methoxy, methylamino, 4-fluorophenyl or 2,4-difluorophenyl, $R^2$ represents hydrogen or alkyl having 1 or 2 carbon atoms, $R^3$ represents a radical having the structure

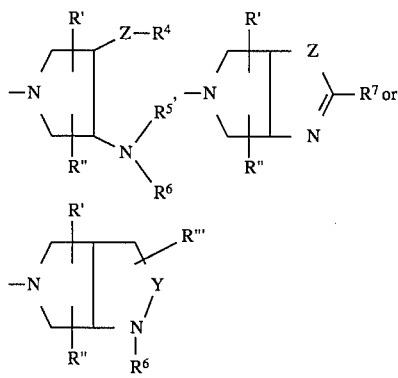

wherein $R^4$ can represent H, $C_1$–$C_2$-alkyl or acetyl, $R^5$ can represent H or $C_1$–$C_2$-alkyl, it also being possible for $R^4$ and $R^5$ together to form a $C_1$–$C_2$-alkylene bridge which is optionally substituted by methyl, $R^6$ can represent H, $CH_3$, $C_2H_5$, $HOCH_2CH_2$, benzyl, $C_1$–$C_4$-alkoxycarbonyl or $C_1$–$C_2$-acyl, $R^7$ can represent H or $CH_3$, R' can represent H or $CH_3$, R" can represent H or $CH_3$, R''' can represent H or $CH_3$, Y can represent O, $CH_2$, $CH_2CH_2$ or $CH_2$—O, it being possible for the $CH_2$—O group to be linked to the nitrogen either via O or via $CH_2$, and Z can represent O or S, and A represents N or C—$R^8$ wherein $R^8$ represents H, fluorine or chlorine, or together with $R^1$ also can form a bridge having the structure

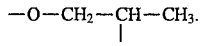

It has furthermore been found that the compounds of the formula (I) are obtained by a process in which compounds of the formula (II)

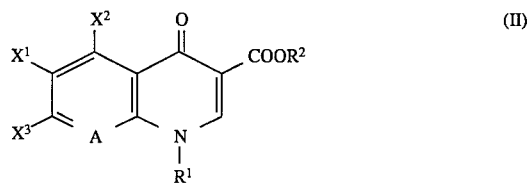

in which $R^1$, $R^2$, $X^1$ and $X^2$ have the abovementioned meanings and $X^3$ represents halogen, in particular fluorine or chlorine, are reacted with compounds of the formula (III)

in which $R^3$ has the abovementioned meaning, if appropriate in the presence of acid entrainers, and if appropriate protective groups contained in $R^3$ are removed (method A).

Compounds of the formula (I) according to the invention

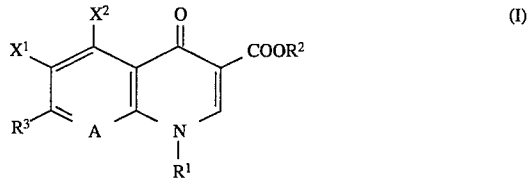

in which $X^1$, $R^1$, $R^2$, $R^3$ and A have the abovementioned meanings and $X^2$ represents amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms or arylthio, can also be obtained by reacting a compound of the formula (IV)

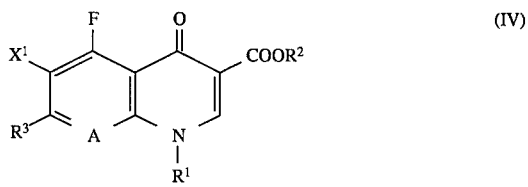

in which $X^1$, $R^1$, $R^2$, $R^3$ and A have the abovementioned meanings, with compounds of the formula (V)

$$X^2\text{—H} \qquad (V)$$

in which $X^2$ has the abovementioned meaning,
if appropriate in the presence of acid entrainers (method B).

Compounds of the formula (Ia) according to the invention

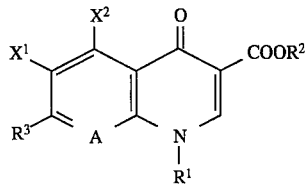

in which
$X^1$, $X^2$, $R^1$, $R^2$ and A have the abovementioned meanings
and $R^3$ represents a radical having the structure

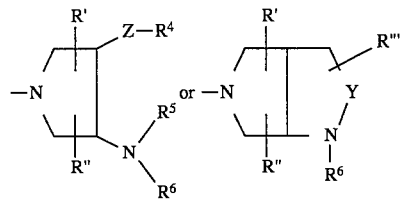

wherein
$R^4$, $R^5$, $R^6$, R', R", R''', Y and Z have the abovementioned meanings,
can also be obtained by a process in which a compound of the formula (VI)

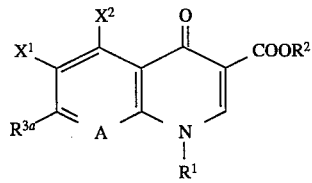

in which
$X^1$, $X^2$, $R^1$, $R^2$ and A have the abovementioned meanings and
$R^{3a}$ represents a radical having the structure

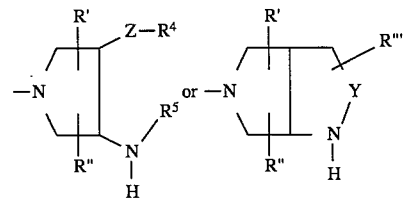

wherein $R^4$, $R^5$, R', R", R''', Y and Z have the abovementioned meanings,
is reacted with compounds of the formula (VII)

$$R^6-X^a \qquad (VII)$$

in which
$R^6$ has the abovementioned meaning and
$X^a$ represents chlorine, bromine, iodine, hydroxyl or acyloxy,
if appropriate in the presence of acid entrainers (method C).

If, for example, 1-cyclopropyl-6,7,8-trifluoro-1,4-dihydro-4-oxo-3-quinolinecarboxylic acid and 1-methyloctahydropyrrolo[3,4-b]pyridine are used as starting substances, the course of the reaction can be represented by the following equation:

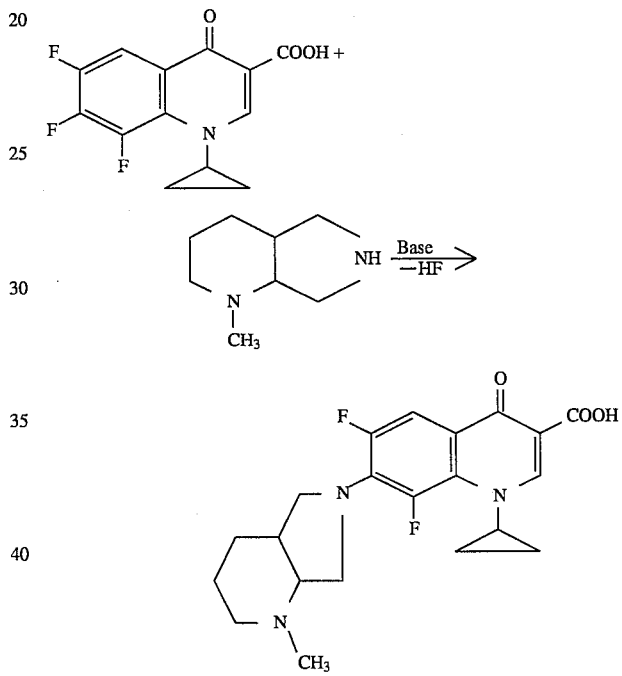

If, for example, 7-chloro-6-fluoro-1-(4-fluorophenyl)-1,4-dihydro-4-oxo-1,8-naphthyridine-3-carboxylic acid and cis-3-tert.-butoxycarbonylamino-4-methoxy-pyrrolidine are used as starting substances, the course of the reaction can be represented by the following equation:

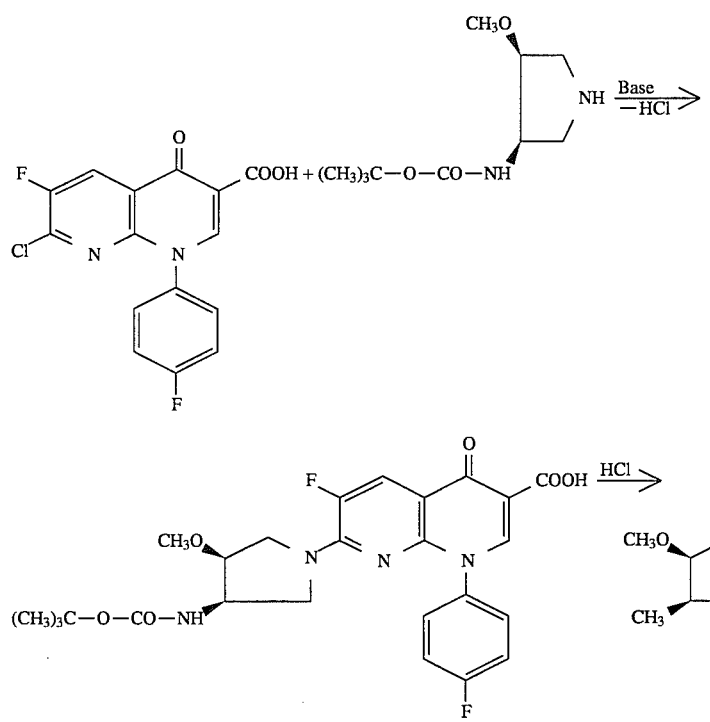

If, for example, 1-cyclopropyl-5,6,8-trifluoro-1,4-dihydro-7-(2-methyl-2,7-diazbicyclo[3.3.0]oct-3-yl)-4-oxo-3-quinolinecarboxylic acid and ammonia are used as starting substances, the course of the reaction can be represented by the following equation:

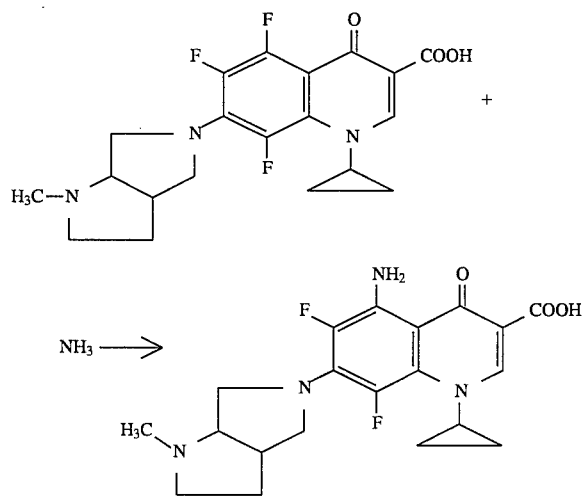

If, for example, 1-cyclopropyl-7-(2,7-diazabicyclo-[3.3.0]oct-7-yl)-6-fluoro-1,4-dihydro-4-oxo-3-quinolinecarboxylic acid and ethanol/hydrogen chloride are used as starting substances, the course of the reaction can be represented by the following equation:

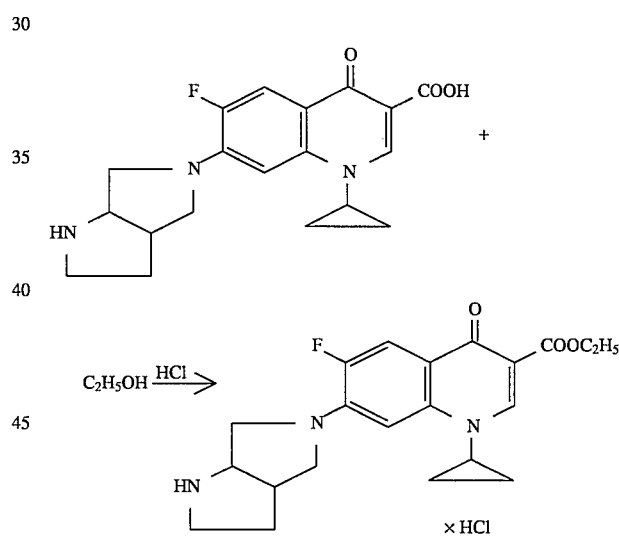

The compounds of the formula (II) used as starting substances are known or can be prepared by known methods. Examples which may be mentioned are:
7-chloro-1-cyclopropyl-6-fluoro-1,4-dihydro-4-oxo-3-quinolinecarboxylic acid (German Patent Application 3,142,854),
1-cyclopropyl-6,7-difluoro-1,4-dihydro-4-oxo-3-quinolinecarboxylic acid (European Patent Application 113,091),
6-chloro-1-cyclopropyl-7,8-difluoro-1,4-dihydro-4-oxo-3-quinolinecarboxylic acid (German Patent Application 3,420,743),
8-chloro-1-cyclopropyl-6,7-difluoro-1,4-dihydro-4-oxo-3-quinolinecarboxylic acid (German Patent Application 3,420,743),
1-cyclopropyl-6,7,8-trifluoro-1,4-dihydro-4-oxo-3-quinolinecarboxylic acid (German Patent Application 3,318,145), 6,8-dichloro-1-cyclopropyl-7-fluoro-1,4-dihydro-4-oxo-3-quinolinecarboxylic acid (German Patent Application 3,420,743),
1-cyclopropyl-6,7-difluoro-1,4-dihydro-8-methyl-4-oxo-3-quinolinecarboxylic acid,
1-cyclopropyl-7-chloro-6-fluoro-1,4-dihydro-8-nitro-4-oxo-3-quinolinecarboxylic acid,
6,7-difluoro-1-ethyl-1,4-dihydro-4-oxo-3-quinolinecarboxylic acid,
7-chloro-6-fluoro-1-ethyl-1,4-dihydro-4-oxo-3-quinolinecarboxylic acid,
7-chloro-6-fluoro-1,4-dihydro-1-(2-hydroxyethyl)-4-oxo-quinolinecarboxylic acid,
6,7-difluoro-1-(2-fluoroethyl)-1,4-dihydro-4-oxo-3-quinolinecarboxylic acid,
8-chloro-1-(2,4-difluorophenyl)-6,7-difluoro-1,4-dihydro-4-oxo-3-quinolinecarboxylic acid (European Patent Application 235,762),
7-chloro-6-fluoro-1,4-dihydro-1-methoxy-4-oxo-3-quinolinecarboxylic acid,
7-chloro-6-fluoro-1,4-dihydro-1-methylamino-4-oxo-3-quinolinecarboxylic acid,
6,7-difluoro-1,4-dihydro-4-oxo-1-phenyl-3-quinolinecarboxylic acid,
7-chloro-1-cyclopropyl-6-fluoro-1,4-dihydro-4-oxo-1,8-naphthyridine-3-carboxylic acid,
6,7-dichloro-1-cyclopropyl-1,4-dihydro-4-oxo-1,8-naphthyridine-3-carboxylic acid,
ethyl 1-cyclopropyl-6,7,8-trifluoro-1,4-dihydro-4-oxo-3-quinolinecarboxylate (German Patent Application 3,318, 145),
9,10-difluoro-2,3-dihydro-3-methyl-7-oxo-7H-pyrido[1,2,3-de][1,4]benzoxazine-6-carboxylic acid (European Patent Application 47,005),
8,9-difluoro-6,7-dihydro-5-methyl-1-oxo-1H,5H-benzo[i,j]-quinolizine-2-carboxylic acid,
7-chloro-6-fluoro-1-phenyl-1,4-dihydro-4-oxo-1,8-naphthyridine-3-thyridine-3-carboxylic acid (European Patent Application 153,580),
7-chloro-6-fluoro-1-(4-fluorophenyl)-1,4-dihydro-4-oxo-1,8-naphthyridine-3-carboxylic acid (European Patent Application 153,580),
6,7,8-trifluoro-1,4-dihydro-1-methylamino-4-oxo-3-quinolinecarboxylic acid (German Patent Application 3,409, 922),
1-amino-6,7,8-trifluoro-1,4-dihydro-4-oxo-3-quinolinecarboxylic acid (German Patent Application 3,409,922),
6,7,8-trifluoro-1,4-dihydro-1-dimethylamino-4-oxo-3-quinolinecarboxylic acid (German Patent Application 3,409,922),
7-chloro-6-fluoro-1,4-dihydro-8-nitro-4-oxo-1-phenyl-3-quinolinecarboxylic acid,
7-chloro-6-fluoro-1-(4-fluorophenyl)-1,4-dihydro-8-nitro-4-oxo-3-quinolinecarboxylic acid,
6,7-difluoro-1-(4-fluorophenyl)-1,4-dihydro-8-methyl-4-oxo-3-quinolinecarboxylic acid,
6-chloro-7-fluoro-1-(4-fluorophenyl)-1,4-dihydro-4-oxo-3-quinolinecarboxylic acid (European Patent Application 131,839),
5,6,7,8-tetrafluoro-1-(2,4-difluorophenyl)-1,4-dihydro-4-oxo-3-quinolinecarboxylic acid,
5,7-dichloro-6-fluoro-1-(2,4-difluorophenyl)-1,4-dihydro-4-oxo-3-quinolinecarboxylic acid,
5,7-dichloro-1-cyclopropyl-6-fluoro-1,4-dihydro-4-oxo-3-quinolinecarboxylic acid,
6-chloro-7-fluoro-1-(2,4-difluorophenyl)-1,4-dihydro-4-oxo-3-quinolinecarboxylic acid (European Patent Application 131,839),
6,7,8-trifluoro-1-(4-fluorophenyl)-1,4-dihydro-4-oxo-3-quinolinecarboxylic acid (European Patent Application 154,780),
6,7,8-trifluoro-1-(2,4-difluorophenyl)-1,4-dihydro-4-oxo-3-quinolinecarboxylic acid (European Patent Application 154,780),
6,7,8-trifluoro-1,4-dihydro-4-oxo-1-phenyl-3-quinolinecarboxylic acid (European Patent Application 154,780),
7-chloro-1-ethyl-6-fluoro-1,4-dihydro-4-oxo-1,8-naphthyridine-3-carboxylic acid,
6,7-difluoro-1,4-dihydro-4-oxo-1-vinyl-3-quinolinecarboxylic acid,
1-cyclopropl-5,6,7,8-tetrafluoro-1,4-dihydro-4-oxo-3-quinolinecarboxylic acid,
5-amino-1-cyclopropyl-6,7,8-trifluoro-1,4-dihydro-4-oxo-3-quinolinecarboxylic acid,
1-cyclopropyl-6,7,8-trifluoro-1,4-dihydro-5-hydroxy-4-oxo-3-quinolinecarboxylic acid, and
1-cyclopropyl-6,7-difluoro-1,4-dihydro-8-methoxy-4-oxo-3-quinolinecarboxylic acid.

The compounds of the formula (III) used as starting compounds are new in some cases. They can be prepared by the following processes.

1. Starting from the N-protected 3,4-epoxypyrrolidine (1) (German Offenlegungsschrift (German Published Specification) 1,929,237 and U.S. Pat. No. 4,254,135), which can optionally also carry one or two methyl or phenyl radicals, the starting compounds of the formula (IIIa)–(IIIe) are prepared.

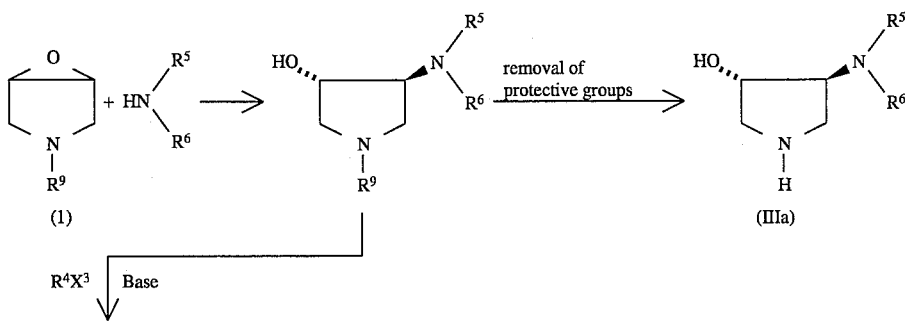

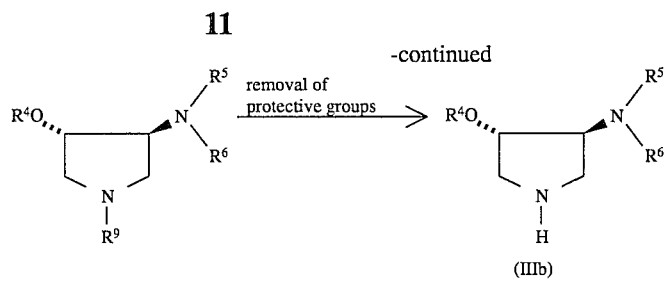
(IIIb)
$R^9$=benzyl, acyl, alkoxycarbonyl, benzyloxycarbonyl, tri-alkylsilyl or sulphonyl (examples of protective groups),
$X^3$=a leaving group, such as halogen, or alkyl- or aryl-sulphonyloxy
2. Starting compounds of the formula (IIIf) are obtained from 2-(1,2-dichloroethyl)-oxirane via the following reaction sequence:
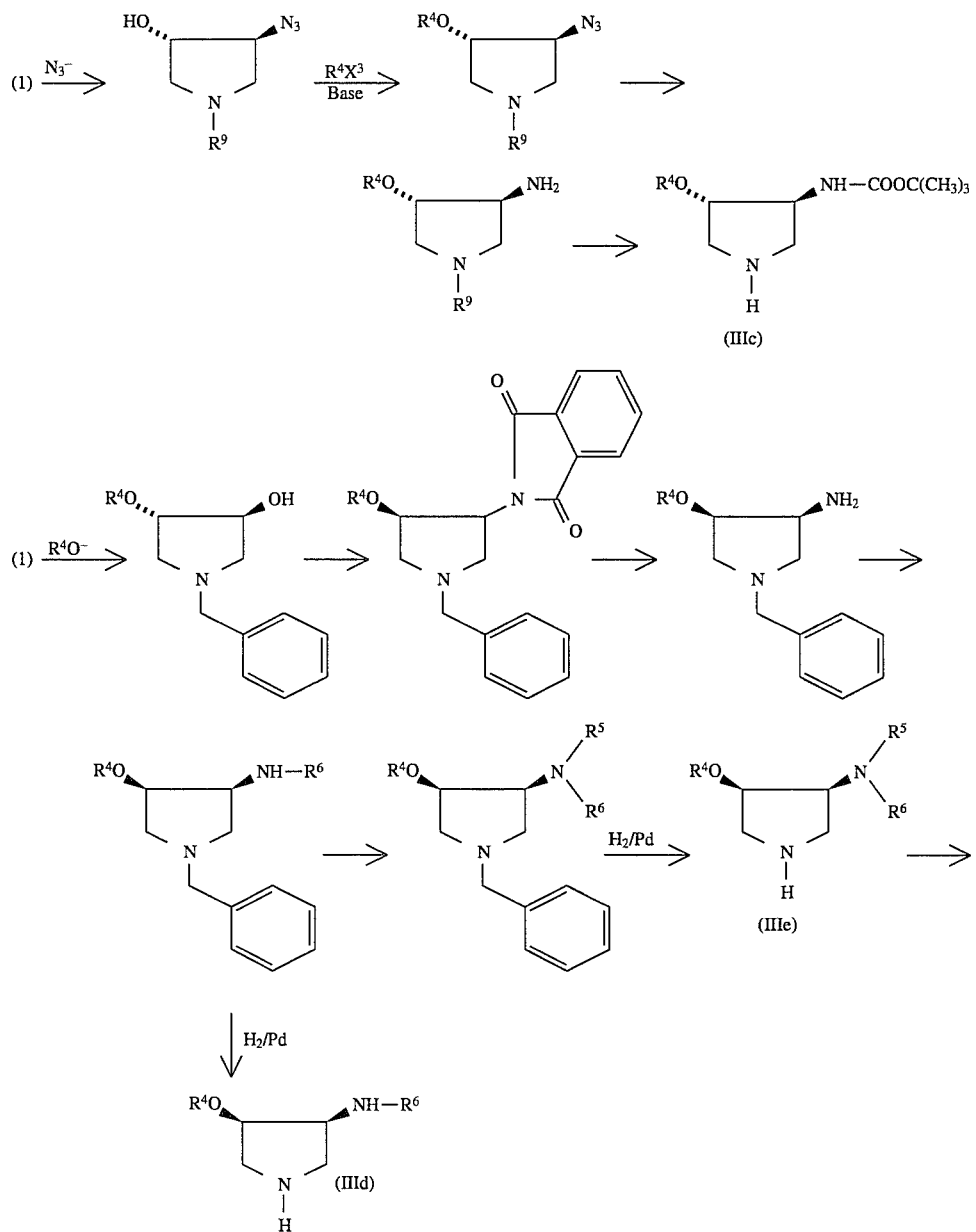

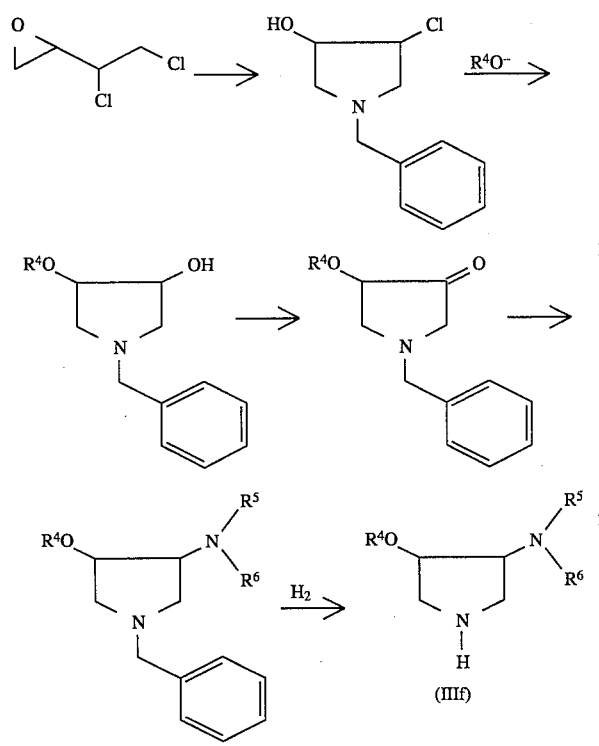

3. By addition of azides onto N-benzylmaleimides which are optionally substituted by one or two methyl or phenyl radicals, starting compounds of the, formula (III g) can be prepared,

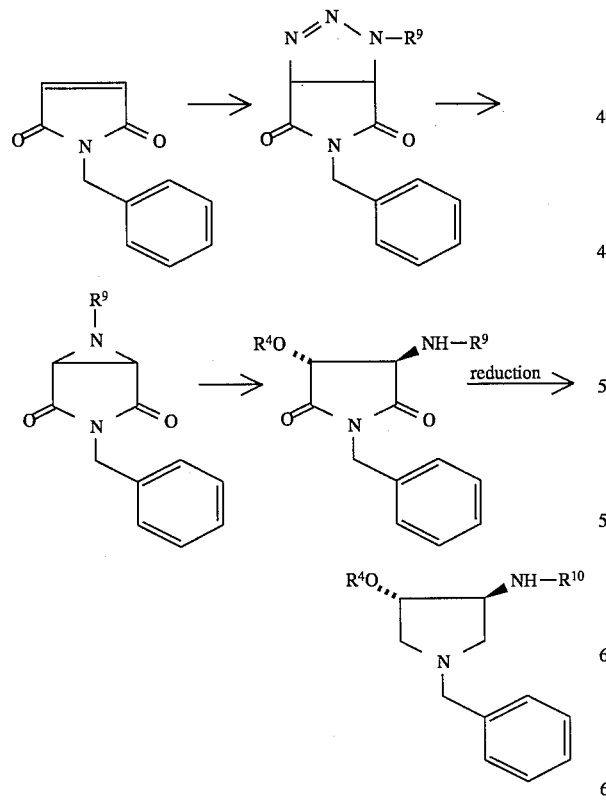

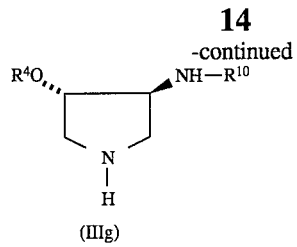

$R^{10}$=H, alkyl or benzyl.

4. From the 3,4-epoxypyrrolidines (1), the starting compounds of the formula (III h) are obtained via cyclization with thionyl chloride:

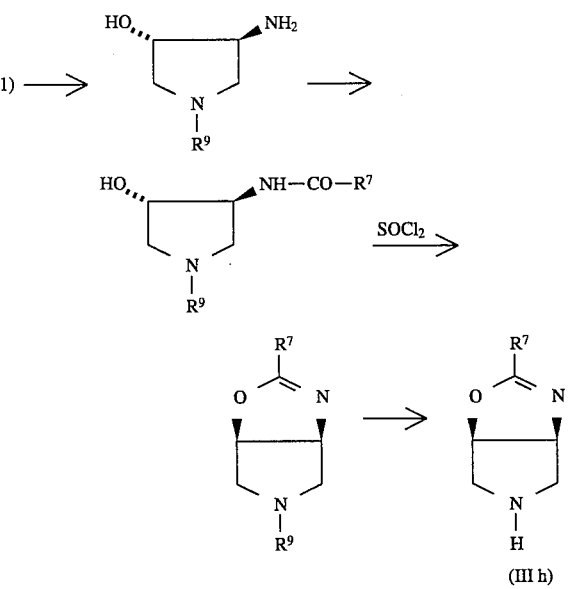

5. By reaction of the 3,4-epoxypyrrolidines (1) with ethanolamines, the starting compounds of the formula (III i) are obtained by intramolecular etherification:

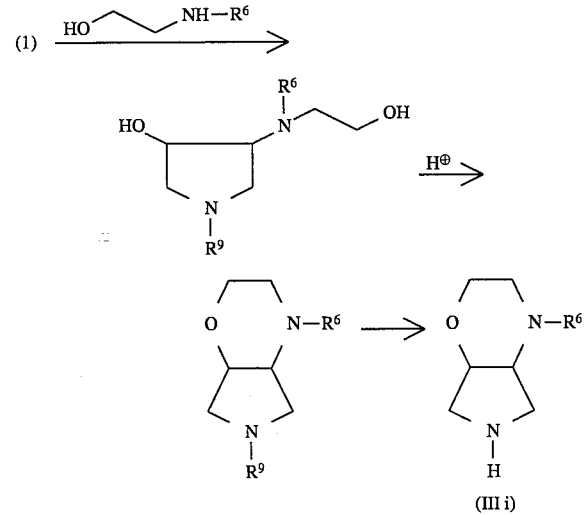

6. The starting compounds of the formula (III j) are obtained from aminoacetaldehyde dimethyl acetal via intramolecular 1,3-dipolar cycloaddition.

15
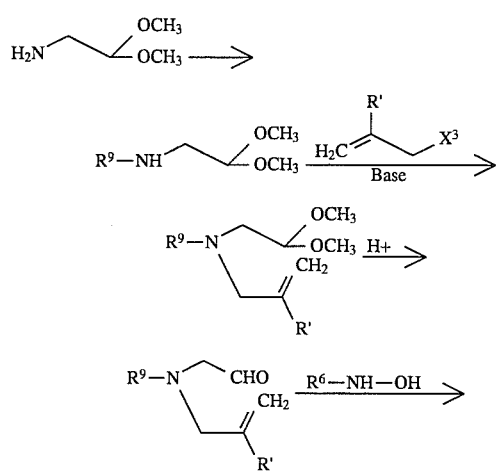
16
-continued
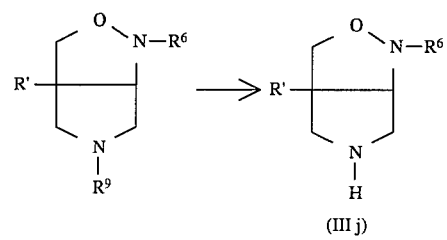
7. Starting from pyridine-2,3-dicarboxylic acid benzylimide, starting compounds (III k) or (III l) are prepared via the reaction steps shown.
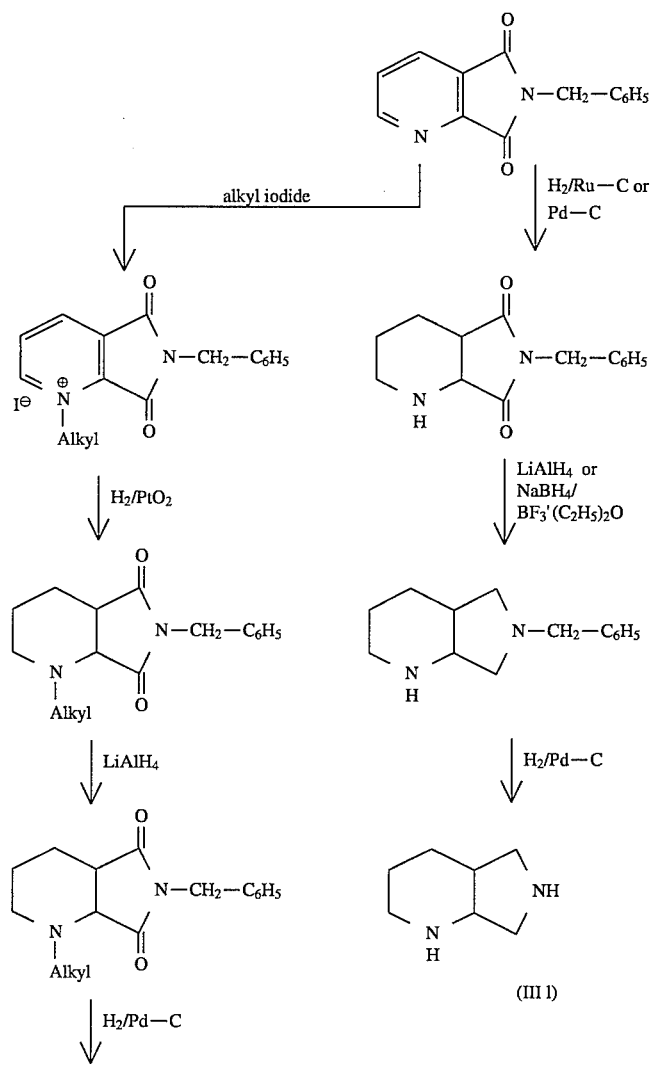

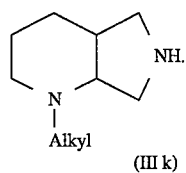
(III k)

8. N-Benzyl-maleimide adds onto 2-chloroethylamines to give 3-(2-chloroethylamino)-succinimides, which are converted into the starting compounds of the formula (III m):

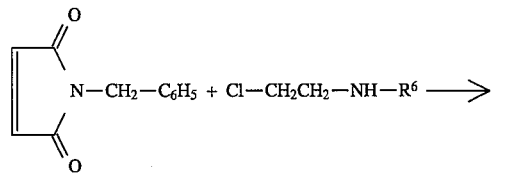

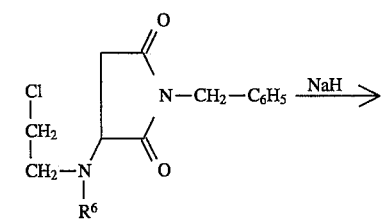

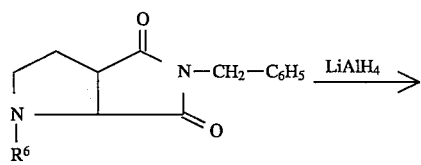

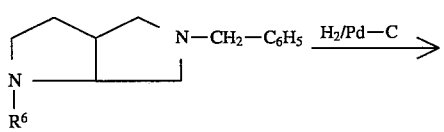

(III m)

9. 2-Methyl-2-propenal-dimethylhydrazone reacts with N-benzylmaleimide to give a cycloadduct, which can be converted into the starting compound (IIIn) by the reaction sequence shown.

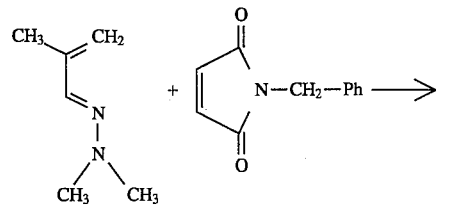

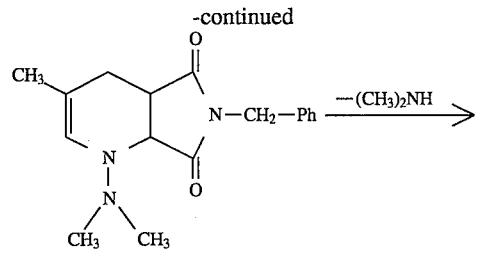

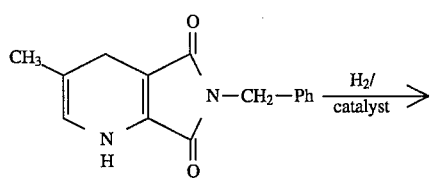

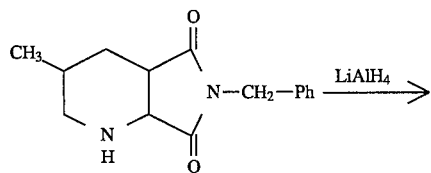

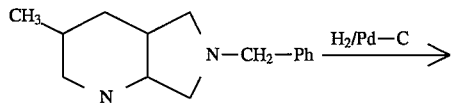

(III n)

10. Starting compounds of the formulae (IIIo), (IIIp) or (IIIq) can be obtained in the following way, starting from N-protected 2,5-dihydropyrroles (3-pyrrolines) by addition of sulphenyl chlorides:

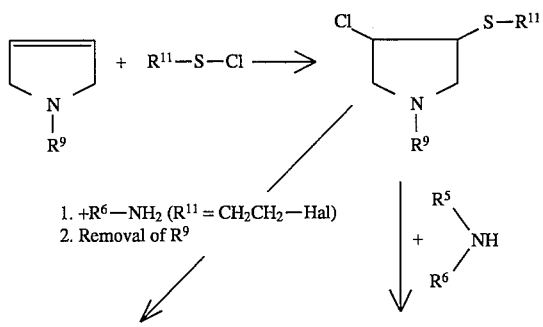

1. +$R^6$—$NH_2$ ($R^{11}$ = $CH_2CH_2$—Hal)
2. Removal of $R^9$

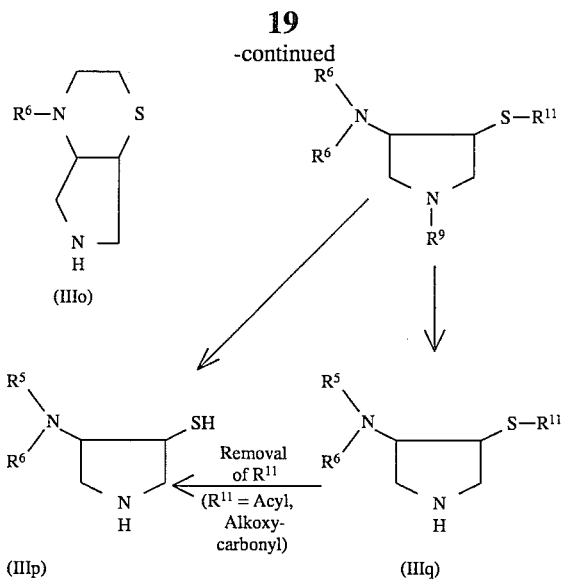

$R^{11} = C_1-C_4$-alkyl which is optionally substituted by halogen or phenyl, which is optionally substituted by halogen, nitro, alkyl or alkoxy, as well as acyl or alkoxycarbonyl.

The following starting compounds, for example, can be prepared in accordance with these general equations. They can be prepared and employed as diastereomer mixtures or in the diastereomerically pure or enantiomerically pure form.

4-amino-3-hydroxypyrrolidine,
3-hydroxy-4-methylaminopyrrolidine,
4-dimethylamino-3-hydroxypyrrolidine,
4-ethylamino-3-hydroxypyrrolidine,
3-amino-4-methoxypyrrolidine,
4-methoxy-3-methylaminopyrrolidine,
3-dimethylamino-4-methoxypyrrolidine,
3-ethylamino-4-methoxypyrrolidine,
3-amino-4-ethoxypyrrolidine,
4-ethoxy-3-methylaminopyrrolidine,
3-dimethylamino-4-ethoxypyrrolidine,
4-ethoxy-3-ethylaminopyrrolidine,
3-hydroxy-4-hydroxyaminopyrrolidine,
3-hydroxy-4-methoxyaminopyrrolidine,
3-hydroxyamino-4-methoxypyrrolidine,
4-methoxy-3-methoxyaminopyrrolidine,
3-benzylamino-4-methoxypyrrolidine,
4-methoxy-3-(5-methyl-2-oxo-1,3-dioxol-4-yl)-methylamino)-pyrrolidine,
3-amino-4-methylmercaptopyrrolidine,
3-acetoxy-4-dimethylaminopyrrolidine,
3-acetamido-4-methoxypyrrolidine,
4-methoxy-3-methoxycarbonylaminopyrrolidine,
3-formamido-4-methoxypyrrolidine,
3-amino-4-methoxy-2-methylpyrrolidine,
3-amino-4-methoxy-5-methylpyrrolidine,
4-methoxy-2-methyl-3-methylaminopyrrolidine,
4-methoxy-5-methyl-3-methylaminopyrrolidine,
3-amino-4-methoxy-2-phenylpyrrolidine,
4-methoxy-3-methylamino-5-phenylpyrrolidine,
3-methyl-2,7-diazabicyclo[3.3.0]octane,
4-methyl-2,7-diazabicyclo[3.3.0]octane,
5-methyl-2,7-diazabicyclo[3.3.0]octane,
3,5-dimethyl-2,7-diazabicyclo[3.3.0]octane,
1,5-dimethyl-2,7-diazabicyclo[3.3.0]octane,
2-oxa-4,7-diazabicyclo[3.3.0]octane
3,3-dimethyl-2-oxa-4,7-diazabicyclo[3.3.0]octane,
3-oxa-2,7-diazabicyclo[3.3.0]octane
1,2-dimethyl-3-oxa-2,7-diazabicyclo[3.3.0]octane,
2,5-dimethyl-3-oxa-2,7-diazabicyclo[3.3.0]octane,
2,8-dimethyl-3-oxa-2,7-diazabicyclo[3.3.0]octane,
5-methyl-3-oxa-2,7-diazabicyclo[3.3.0]octane,
2-oxa-4,7-diazabicyclo[3.3.0]oct-3-ene,
3-methyl-2-oxa-4,7-diazabicyclo[3.3.0]oct-3-ene,
3-phenyl-2-oxa-4,7-diazabicyclo[3.3.0]oct-3-ene,
6-methyl-2-oxa-4,7-diazabicyclo[3.3.0]oct-3-ene,
8-methyl-2-oxa-4,7-diazabicyclo[3.3.0]oct-3-ene,
3-methyl-2,8-diazabicyclo[4.3.0]nonane,
4-methyl-2,8-diazabicyclo[4.3.0]nonane,
5-methyl-2,8-diazabicyclo[4.3.0]nonane,
6-methyl-2,8-diazabicyclo[4.3.0]nonane,
3-methyl-2-oxa-5,8-diazabicyclo[4.3.0]nonane,
4-methyl-2-oxa-5,8-diazabicyclo[4.3.0]nonane,
1-methyl-2-oxa-5,8-diazabicyclo[4.3.0]nonane,
3,5-dimethyl-2-oxa-5,8-diazabicyclo[4.3.0]nonane,
2-thia-5,8-diazabicyclo[4.3.0]nonane,
5-methyl-2-thia-5,8-diazabicyclo[4.3.0]nonane,
3,5-dimethyl-2-thia-5,8-diazabicyclo[4.3.0]nonane,
3-oxa-2,8-diazabicyclo[4.3.0]nonane,
2-methyl-9-oxa-2,8-diazabicyclo[4.3.0]nonane,
4-methyl-3-oxa-2,8-diazabicyclo[4.3.0]nonane,
2,5-dimethyl-3-oxa-2,8-diazabicyclo[4.3.0]nonane,
3-oxa-5,8-diazabicyclo[4.3.0]nonane,
5-methyl-3-oxa-5,8-diazabicyclo[4.3.0]nonane,
1,5-dimethyl-3-oxa-5,8-diazabicyclo[4.3.0]nonane and
4,4-dimethyl-3-oxa-5,8-diazabicyclo[4.3.0]nonane.

The reaction of (II) with (III) according to method A, in which the compounds (III) can also be employed in the form of their hydrochlorides, is preferably carried out in a diluent, such as dimethyl sulphoxide, N,N-dimethylformamide, N-methylpyrrolidone, hexamethyl-phosphoric acid triamide, sulpholane, acetonitrile, water, an alcohol, such as methanol, ethanol, n-propanol or isopropanol, glycol monomethyl ether or pyridine. Mixtures of these diluents can also be used or the reaction can be carried out without any solvent.

Acid-binding agents which can be used are all the customary inorganic and organic acid-binding agents. These include, preferably, the alkali metal hydroxides, alkali metal carbonates, organic amines and amidines. Particularly suitable acid-binding agents which may be mentioned specifically are: triethylamine, 1,4-diazabicyclo[2.2.2]octane (DABCO), 1,8-diazabicyclo[5,4,0]undec-7-ene (DBU) or excess amine (III).

The reaction temperatures can be varied within a substantial range. The reaction is in general carried between about 20° and 200° C. preferably between 80° and 180° C.

The reaction can be carried out under normal pressure, and also under elevated pressure. It is in general carried out under pressures between about 1 and 100 bar, preferably between 1 and 10 bar.

In carrying out the process according to the invention, 1 to 15 mols, preferably 1 to 6 mols, of the compound (III) are employed per mol of the carboxylic acid (II).

Free hydroxyl groups can be protected during the reaction by a suitable hydroxyl-protective group, for example by the tetrahydropyranyl radical, and can be liberated again when the reaction has ended (see J. F .W. McOmie, Protective Groups in Organic Chemistry (1973), page 104).

Free amino functions can be protected during the reaction by a suitable amino-protective group, for example by the ethoxycarbonyl or tert.-butoxycarbonyl radical, and liberated again when the reaction has ended by treatment with a suitable acid, such as hydrochloric acid or trifluoroacetic acid (see Houben-Weyl, Methoden der organischen Chemie (Methods of Organic Chemistry), Volume E4, page 144 (1983); and J. F. W. McOmie, Protective Groups in Organic Chemistry (1973), page 43).

The reaction of (IV) with (V) according to method B is preferably carried out in a diluent, such as dimethyl sulphoxide, dioxane, N,N-dimethylformamide, N-methyl-pyrrolidone, hexamethyl-phosphoric acid triamide, sulpholane, water, an alcohol, such as methanol, ethanol, n-propanol or isopropanol, glycol monomethyl ether or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Particularly suitable acid-binding agents which may be mentioned specifically are: triethylamine, 1,4-diazabicyclo[2.2.2]octane (DABCO) or 1,8-diazabicyclo[5.4.0]undec-7-ene (DBU).

The reaction temperatures can be varied within a substantial range. The reaction is in general carried out between about 70° and about 200° C. preferably between 100° and 180° C.

The reaction can be carried out under normal pressure, and also under increased pressure. It is in general carried out under pressures of between about 1 bar and about 100 bar, preferably between 1 and 10 bar.

In carrying out the process according to the invention by method B, 1 to 50 mols, preferably 1 to 30 mols, of the compound (V) are employed per mol of the compound (IV).

To prepare the esters according to the invention, the carboxylic acid on which they are based is preferably reacted in excess alcohol in the presence of strong acids, such as sulphuric acid, anhydrous hydrochloric acid, methanesulphonic acid, p-toluenesulphonic acid or acid ion exchangers, at temperatures from about 20° to 200° C., preferably about 60° to 120° C. The water of reaction formed can also be removed by azeotropic distillation with chloroform, carbon tetrachloride, benzene or toluene.

The esters are also advantageously prepared by heating the acid on which they are based with dimethylformamide dialkyl acetal in a solvent, such as dimethylformamide.

The 5-methyl-2-oxo-1,3-dioxol-4-yl-methyl esters used as a prodrug are obtained by reaction of an alkali metal salt of the carboxylic acid on which they are based with 4-bromomethyl- or 4-chloromethyl-5-methyl-1,3-dioxol-2-one in a solvent, such as dimethylformamide, dimethylacetamide, N-methylpyrrolidone, dimethyl sulphoxide or tetramethylurea at temperatures of about 0° to 100° C., preferably 0° to 50° C.

The acid addition salts of the compounds according to the invention are prepared in the customary manner, for example by dissolving the betaine in excess aqueous acid and precipitating the salt with a water-miscible organic solvent, such as methanol, ethanol, acetone or acetonitrile. It is also possible to heat equivalent amounts of the betaine and acid in water or an alcohol, such as glycol monomethyl ether, and then to evaporate the mixture to dryness or filter off the precipitated salt with suction. Pharmaceutically usable salts are to be understood as, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in excess alkali metal or alkaline earth metal hydroxide solution, filtering from the undissolved betaine and evaporating the filtrate to dryness. Sodium, potassium or calcium salts are pharmaceutically suitable. The corresponding silver salts are obtained by reaction of an alkali metal or alkaline earth metal salt with a suitable silver salt, such as silver nitrate.

The compounds listed by way of example in Table 1 can also be prepared, in addition to the active compounds mentioned in the examples, it being possible for these compounds to be present both as diastereomer mixtures or as the diastereomerically pure or enantiomerically pure compounds.

TABLE 1

Structure: quinolone core with substituents $X^1$, $X^2$, $R^3$, A, $R^1$ on the ring and $COOR^2$ at the 3-position.

| $R^1$ | $R^2$ | $R^3$ | $X^1$ | $X^2$ | A |
|---|---|---|---|---|---|
| cyclopropyl | H | morpholinyl-piperazine (O,NH) N— | F | H | CH |
| cyclopropyl | $C_2H_5$ | morpholinyl-piperazine (O,NH) N— | F | H | CF |
| cyclopropyl | H | thiomorpholinyl-piperazine (S,NH) N— | F | H | CF |

TABLE 1-continued
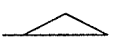
| R¹ | R² | R³ | X¹ | X² | A |
|---|---|---|---|---|---|
| 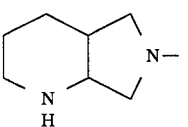 | H | 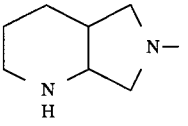 | F | H | C–OCH₃ |
| C₂H₅ | H | 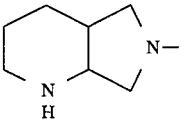 | F | H | CH |
| C₂H₅ | H | 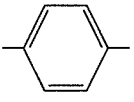 | F | NH₂ | CF |
| 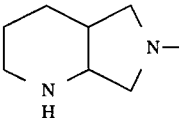 | H | 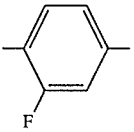 | F | H | CF |
| 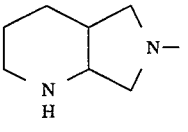 | H | 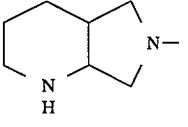 | F | H | CF |
| –CH=CH₂ | H | 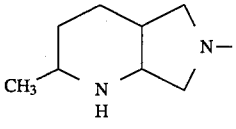 | F | H | CH |
| HO–CH₂CH₂– | H | 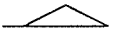 | F | H | CH |
| 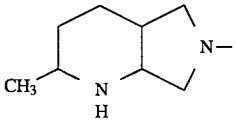 | H |  | F | F | CF |
| 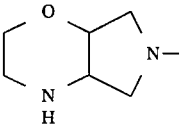 | H |  | F | F | CF |
| 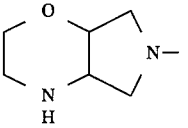 | –C₂H₅ | 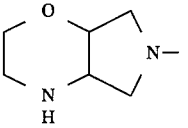 | F | H | CF |

TABLE 1-continued

| R¹ | R² | R³ | X¹ | X² | A |
|---|---|---|---|---|---|
| cyclopropyl | CH₂-O-C(=O)-O-C(CH₃)= | octahydropyrrolo[3,4-b][1,4]oxazine | F | H | CF |
| cyclopropyl | H | octahydropyrrolo[3,4-b][1,4]oxazine | F | NH₂ | CF |
| cyclopropyl | H | octahydropyrrolo[3,4-b][1,4]oxazine | F | OH | CF |
| cyclopropyl | H | octahydropyrrolo[3,4-b][1,4]oxazine | F | H | CCl |
| cyclopropyl | H | octahydropyrrolo[3,4-b][1,4]oxazine | F | H | CH |
| cyclopropyl | H | octahydropyrrolo[3,4-b][1,4]oxazine | F | H | N |
| cyclopropyl | H | 2-methyl-octahydropyrrolo[3,4-b][1,4]oxazine | F | H | CF |
| cyclopropyl | H | 2-methyl-octahydropyrrolo[3,4-b][1,4]oxazine | F | F | CF |
| cyclopropyl | H | 3-methyl-octahydropyrrolo[3,4-b][1,4]oxazine | F | H | CF |
| cyclopropyl | H | 4a-methyl-octahydro-1,6-naphthyridine | F | F | CF |

TABLE 1-continued
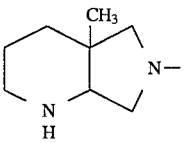
| R¹ | R² | R³ | X¹ | X² | A |
|---|---|---|---|---|---|
| F—CH₂CH₂ | H | 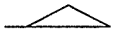 | F | H | CH |
| 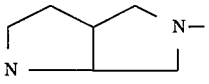 (cyclopropyl) | H |  | F | NH₂ | CF |
| 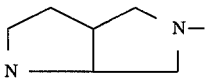 | H |  | F | H | N |
| 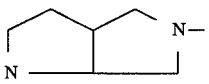 | H | 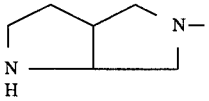 | F | H | CCl |
| CH₃O | H | 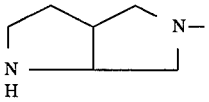 | F | H | CH |
| CH₃—NH— | H |  | F | H | CF |
| 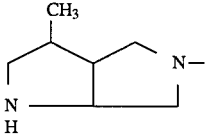 | H | 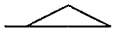 | F | H | CF |
| 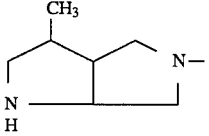 | H | 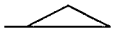 | F | H | CCl |
| 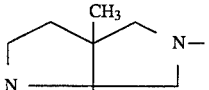 | H | 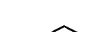 | F | H | CF |
|  | H | (CH₃O, H₂N substituted pyrrolidine) | F | H | C—CH₃ |

TABLE 1-continued
| R¹ | R² | R³ | X¹ | X² | A |
|---|---|---|---|---|---|
| 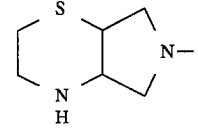 | H |  | F | H | CH |
| 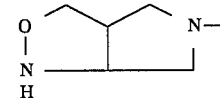 | H |  | F | H | CF |
| 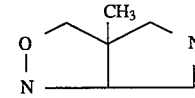 | H |  | F | H | CH |
| 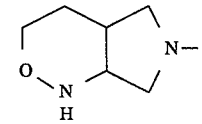 | H |  | F | H | CF |
| 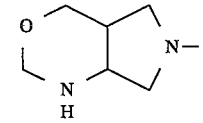 | H |  | F | H | CH |
| 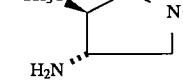 | H |  | F | H | CCl |
| 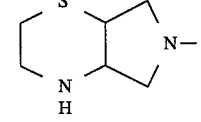 | H |  | F | H | Cl |
| 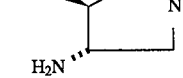 | H |  | F | H | N |
| 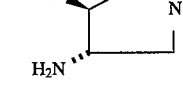 | H | 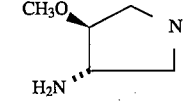 | F | NH₂ | CF |
| —C₂H₅ | H |  | F | H | CF |
|  | C₂H₅ | | F | H | CF |

TABLE 1-continued
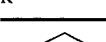
| R¹ | R² | R³ | X¹ | X² | A |
|---|---|---|---|---|---|
| 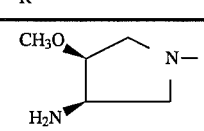 | H | 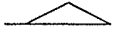 | F | H | N |
| 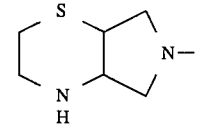 | H | 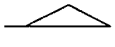 | F | H | N |
| 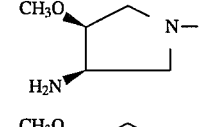 | CH₃ | 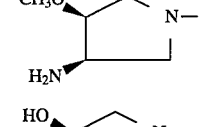 | F | H | CF |
| —C₂H₅ | H |  | F | H | N |
| 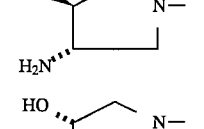 | H |  | F | H | CF |
| 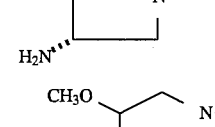 | H |  | F | H | CF |
| 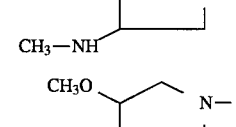 | H |  | F | H | CH |
| 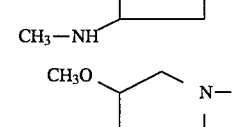 | H |  | F | H | C—CH₃ |
| 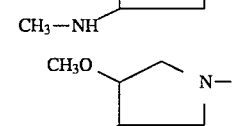 | H |  | F | H | CCl |
| 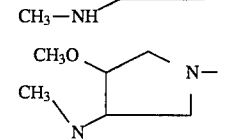 | H |  | F | H | N |
|  | H | (CH₃O, CH₃, CH₃ dimethylamino pyrrolidine) | F | H | CF |

TABLE 1-continued
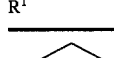
| R¹ | R² | R³ | X¹ | X² | A |
|---|---|---|---|---|---|
| 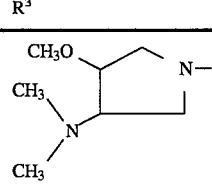 | H | 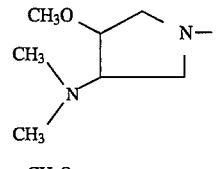 | F | NH₂ | CF |
| —C₂H₅ | H | 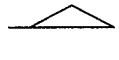 | F | H | CH |
| 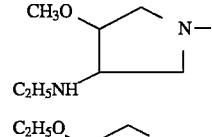 | H | 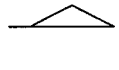 | F | H | CF |
| 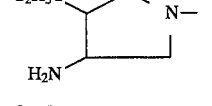 | H |  | F | H | CF |
| 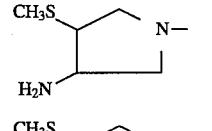 | H | 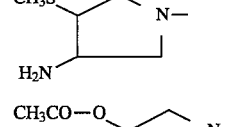 | F | H | CF |
| —C₂H₅ | H |  | F | H | CH |
| 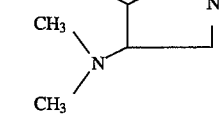 | H |  | F | H | CH |
| 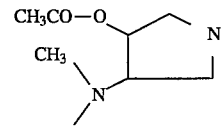 | H | 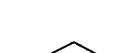 | F | H | CF |
| 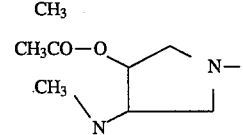 | H |  | F | H | CCl |
| 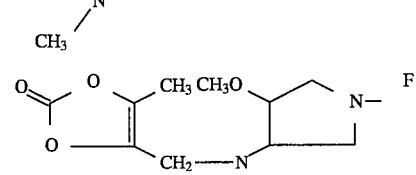 | H | | F | H | CH |

TABLE 1-continued
| R¹ | R² | R³ | X¹ | X² | A |
|---|---|---|---|---|---|
| 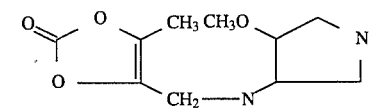 | H |  | F | H | CF |
| 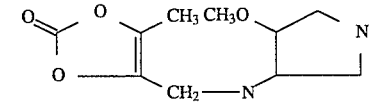 | H |  | F | H | CCl |
| 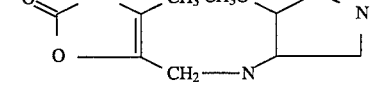 | H |  | F | H | N |
| 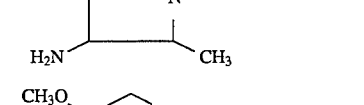 | H |  | F | H | CF |
| 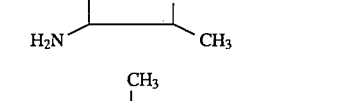 | H |  | F | H | CCl |
| 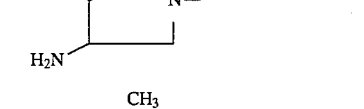 | H |  | F | H | CF |
| 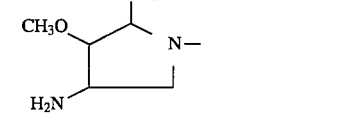 | H |  | F | H | CH |
| 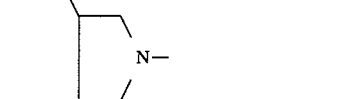 | H |  | F | H | CF |
| 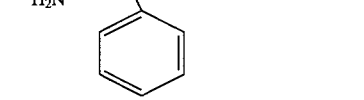 | H | | F | H | CF |

TABLE 1-continued

[Structure shown at top of table: quinolone core with X¹, X², R³, A, R¹, R² and COOR² substituents]

| R¹ | R² | R³ | X¹ | X² | A |
|---|---|---|---|---|---|
| cyclopropyl | H | 3-methoxy-4-(benzylaminomethyl)pyrrolidin-1-yl (CH₃O on pyrrolidine C3, -CH₂-NH-CH₂-Ph on C4) | F | H | CF |
| cyclopropyl | H | 3-methoxy-4-amino-pyrrolidin-1-yl (CH₃O on C3, H₂N on C4) | F | H | C-CH₃ |
| cyclopropyl | H | 3-methoxy-4-(methoxycarbonylamino)pyrrolidin-1-yl (CH₃O-CONH-) | F | H | CF |
| cyclopropyl | H | 3-methoxy-4-(methoxymethylideneamino)pyrrolidin-1-yl (OCH—NH-) | F | H | CF |
| cyclopropyl | H | 3-methoxy-4-(methoxymethylideneamino)pyrrolidin-1-yl (OCH—NH-) | F | H | CCl |
| cyclopropyl | H | 3-methoxy-4-(hydroxyamino)pyrrolidin-1-yl (HO—NH-) | F | H | CF |
| cyclopropyl | H | 3-methoxy-4-(methoxyamino)pyrrolidin-1-yl (CH₃O—NH-) | F | H | CF |
| cyclopropyl | H | 3-methoxy-4-(methoxycarbonylamino)pyrrolidin-1-yl (CH₃O—CONH-) | F | H | CCl |
| cyclopropyl | H | 3-methoxy-4-(methoxycarbonylamino)pyrrolidin-1-yl (CH₃O—CONH-) | F | H | CH |
| cyclopropyl | H | 3-(oxazolin-2-yl)pyrrolidin-1-yl | F | H | CH |
| cyclopropyl | H | 3-(oxazolin-2-yl)pyrrolidin-1-yl | F | H | CF |
| cyclopropyl | H | 3-(oxazolin-2-yl)pyrrolidin-1-yl | F | H | CCl |

TABLE 1-continued

Structure: pyridone core with X¹, X², R³, A substituents, COOR² group, and N-R¹

| R¹ | R² | R³ | X¹ | X² | A |
|---|---|---|---|---|---|
| cyclopropyl | H | 2-acetyl-hexahydropyrrolo[3,4-b]pyrrol-5-yl (with CH₃C(=O), N, O) | F | H | CF |
| 4-fluorophenyl | H | 2-acetyl-hexahydropyrrolo[3,4-b]pyrrol-5-yl (with CH₃C(=O), N, O) | F | H | CF |
| cyclopropyl | H | hexahydropyrrolo[3,4-b][1,4]oxazin-6-yl (O, NH) | F | H | C—CH₃ |
| cyclopropyl | H | hexahydropyrrolo[3,4-b][1,4]thiazin-6-yl (S, NH) | F | H | C—CH₃ |
| cyclopropyl | H | octahydropyrrolo[3,4-b]pyridin-6-yl (NH) | F | H | C—CH₃ |
| 2,4-difluorophenyl | H | octahydropyrrolo[3,4-b]pyridin-6-yl (NH) | F | H | N |
| 2,4-difluorophenyl | H | octahydropyrrolo[3,4-b]pyridin-6-yl (NH) | F | H | CH |
| 2,4-difluorophenyl | H | octahydropyrrolo[3,4-b]pyridin-6-yl (NH) | F | H | CCl |
| 2,4-difluorophenyl | C₂H₅ | octahydropyrrolo[3,4-b]pyridin-6-yl (NH) | F | F | CF |
| 4-fluorophenyl | H | octahydropyrrolo[3,4-b]pyridin-6-yl (N-CH₂CH₂OH) | F | NH₂ | CF |

TABLE 1-continued
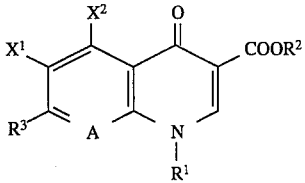

TABLE 1-continued
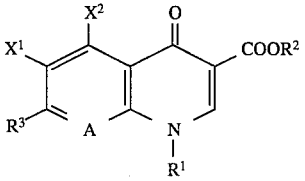
| R¹ | R² | R³ | X¹ | X² | A |
|---|---|---|---|---|---|
| 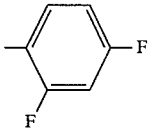 | H | 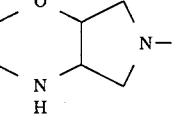 | F | H | N |
| 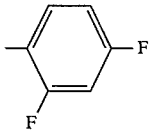 | H | 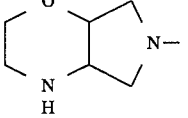 | F | N | CH |
| 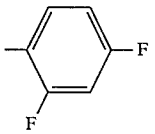 | H | 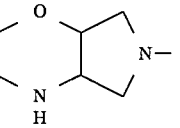 | F | H | CCl |
| 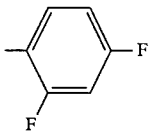 | H | 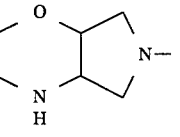 | F | F | CF |
| 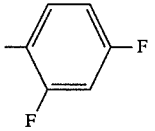 | H | 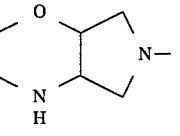 | F | NH₂ | CF |
| 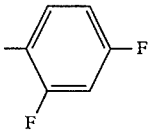 | H | 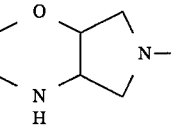 | F | Cl | CH |
| 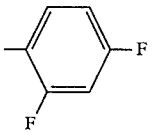 | H | 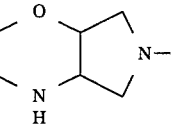 | F | Cl | CF |
| 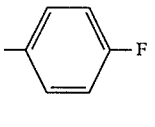 | H | 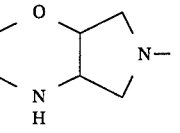 | F | H | N |
| 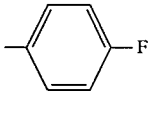 | H | 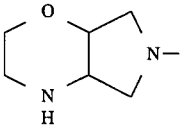 | F | H | CF |

TABLE 1-continued

Structure: pyridone core with X², O, COOR² at top; X¹, R³, A, N-R¹ around ring.

| R¹ | R² | R³ | X¹ | X² | A |
|---|---|---|---|---|---|
| 4-F-phenyl | H | octahydropyrrolo-oxazine (O, NH) | F | H | CH |
| 4-F-phenyl | H | octahydropyrrolo-oxazine (O, NH) | F | H | CCl |
| 4-F-phenyl | H | octahydropyrrolo-oxazine (O, NH) | F | F | CF |
| 4-F-phenyl | H | octahydropyrrolo-oxazine (O, NH) | F | NH₂ | CF |
| 4-F-phenyl | H | octahydropyrrolo-oxazine (O, NH) | F | Cl | CH |
| 4-F-phenyl | H | octahydropyrrolo-oxazine (O, NH) | F | Cl | CF |
| 2,4-diF-phenyl | H | octahydropyrrolo-pyridine (NH) | F | H | CF |
| 2,4-diF-phenyl | H | octahydropyrrolo-pyrrole (NH) | F | H | CH |
| 2,4-diF-phenyl | H | octahydropyrrolo-pyrrole (NH) | F | H | CCl |
| 2,4-diF-phenyl | H | octahydropyrrolo-pyrrole (NH) | F | F | CF |

TABLE 1-continued
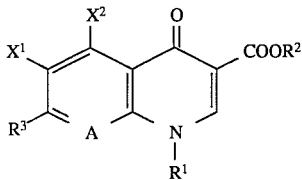
| R¹ | R² | R³ | X¹ | X² | A |
|---|---|---|---|---|---|
| 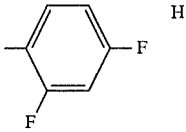 | H | 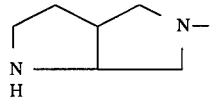 | F | NH₂ | CF |
| 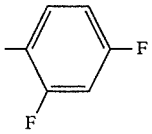 | H | 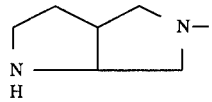 | F | Cl | Cl |
| 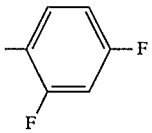 | H | 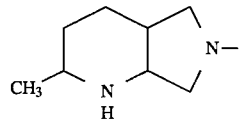 | F | H | CF |
| 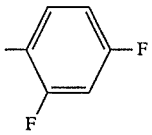 | H | 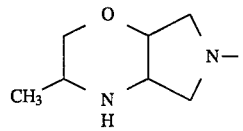 | F | H | N |
| 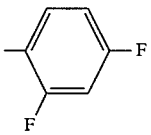 | H | 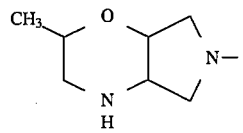 | F | H | N |
| 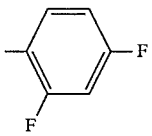 | H | 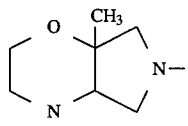 | F | H | N |
| 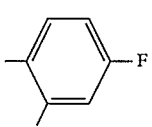 | H | 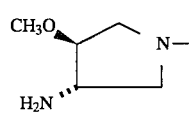 | F | H | N |
| 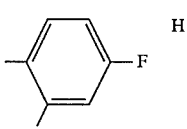 | H | 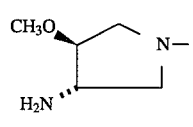 | F | H | CH |
| 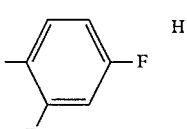 | H | 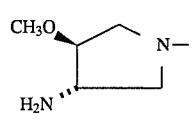 | F | H | CCl |

TABLE 1-continued

| R¹ | R² | R³ | X¹ | X² | A |
|---|---|---|---|---|---|
| 2,4-difluorophenyl | H | 3-amino-4-methoxypyrrolidin-1-yl | F | F | CF |
| 2,4-difluorophenyl | H | 3-amino-4-methoxypyrrolidin-1-yl | F | NH₂ | CF |
| 2,4-difluorophenyl | H | 3-amino-4-methoxypyrrolidin-1-yl | F | Cl | CH |
| 2,4-difluorophenyl | H | 3-amino-4-methoxypyrrolidin-1-yl | F | Cl | CF |
| 2,4-difluorophenyl | H | 3-amino-4-ethoxypyrrolidin-1-yl | F | H | N |
| 2,4-difluorophenyl | H | 3-amino-4-ethoxypyrrolidin-1-yl | F | H | CF |
| 2,4-difluorophenyl | H | 3-amino-4-ethoxypyrrolidin-1-yl | F | H | CH |
| 2,4-difluorophenyl | H | 3-amino-4-methoxypyrrolidin-1-yl | F | H | N |
| 2,4-difluorophenyl | H | 3-amino-4-methoxypyrrolidin-1-yl | F | H | CH |

TABLE 1-continued

Structure:

$X^1$, $X^2$ substituents on a vinyl group connected to a pyridone ring bearing $COOR^2$ at position 3, oxo at position 4, $R^3$ at position 7, with ring atom $A$ and $N-R^1$.

| $R^1$ | $R^2$ | $R^3$ | $X^1$ | $X^2$ | A |
|---|---|---|---|---|---|
| 2,4-difluorophenyl | H | 3-methoxy-4-amino-pyrrolidin-1-yl | F | H | CCl |
| 2,4-difluorophenyl | H | 3-methoxy-4-amino-pyrrolidin-1-yl | F | F | CF |
| 2,4-difluorophenyl | H | 3-methoxy-4-amino-pyrrolidin-1-yl | F | $NH_2$ | CF |
| 2,4-difluorophenyl | H | 3-methoxy-4-amino-pyrrolidin-1-yl | F | Cl | CH |
| 2,4-difluorophenyl | H | 3-methoxy-4-amino-pyrrolidin-1-yl | F | Cl | CF |
| 2,4-difluorophenyl | H | 3-ethoxy-4-amino-pyrrolidin-1-yl | F | H | N |
| 2,4-difluorophenyl | H | 3-ethoxy-4-amino-pyrrolidin-1-yl | F | H | CF |
| 2,4-difluorophenyl | H | 3-ethoxy-4-amino-pyrrolidin-1-yl | F | H | CH |

Example of a tablet according to the invention
Each tablet contains:

| | |
|---|---|
| Compound of Example 1 | 583.0 mg |
| Microcrystalline cellulose | 55.0 mg |
| corn starch | 72.0 mg |
| Insoluble poly-(1-vinyl-2-pyrrolidone) | 30.0 mg |
| Highly disperse silica | 5.0 mg |
| Magnesium stearate | 5.0 mg |
| | 750.0 mg |

The lacquer shell contains:

| | |
|---|---|
| Poly-(O-hydroxypropyl-O-methyl)-cellulose 15 cp | 6.0 mg |
| Macrogol 4000, recommended INN polyethylene glycols (DAB) | 2.0 mg |
| Titanium (IV) oxide | 2.0 mg |
| | 10.0 mg |

The compounds according to the invention, while having a low toxicity, exhibit a broad antibacterial spectrum against Gram-positive and Gram-negative germs, in particular against Enterobacteriaceae; above all also against those which are resistant towards various antibiotics, such as, for example, penicillins, cephalosporins, aminoglycosides, sulphonamides and tetracyclines.

These useful properties enable them to be used as chemotherapeutic active compounds in medicine and as substances for preserving inorganic and organic materials, in particular all types of organic materials, for example polymers, lubricants, paints, fibers, leather, paper and wood, and foodstuffs and water.

The compounds according to the invention are active against a very broad spectrum of microorganisms. Gram-negative and Gram-positive bacteria and bacteria-like microrganisms can be combated and the diseases caused by these pathogens can be prevented, alleviated and/or cured with the aid of these compounds.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases caused by the following pathogens or by mixtures of the following pathogens can be treated and/or prevented:

Gram-positive *cocci*, for example Staphylococci (*Staph. aureus* and *Staph. epidermidis*) and Streptococci (*Strept. agalactiae, Strept. faecalis, Strept. pneumoniae* and *Strept. pyogenes*); Gram-negative *cocci* (*Neisseria gonorrhoeae*). and Gram-negative rod-shaped *bacilli*, such as Enterobacteriaceae, for example *Escherichia coli, Haemophilus influenzae,* Citrobacter (*Citrob. freundii* and *Citrob. divernis*), Salmonella and Shigella; and furthermore Klebsiella (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia and Yersinia, and the genus Acinetobacter. The antibacterial spectrum moreover includes the genus Pseudomonas (*Ps. aeruginosa* and *Ps. maltophilia*) as well as strictly anaerobic bacteria, such as, for example, *Bacteroides fragilis,* representatives of the genus Peptococcus, Peptostreptococcus and the genus Clostridium; and furthermore Mycoplasma (*M. pneumoniae, M. hominis* and *M. urealyticum*) and Mycobacteria, for example *Mycobacterium tuberculosis*.

The above list of pathogens is to be interpreted merely as examples and in no way as limiting. Examples which may be mentioned of diseases which are caused by the pathogens or mixed infections mentioned and can be prevented, alleviated or cured by the compounds according to the invention are:

infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis and infections of the nervous system, salpingitis, endometritis, genital infections, pelveoperitonitis and eye infections.

As well as in humans, bacterial infections can also be treated in other species. Examples which may be mentioned are:

Pigs: colidiarrhoea, enterotoxaemia, sepsis, dysentery, salmonellosis, mastitis-metritis-agalactia syndrome and mastitis;

Ruminants (cattle, sheep and goats): diarrhoea, sepsis, bronchopneumonia, salmonellosis, pasteurellosis, mycoplasmosis and genital infections;

Horses: bronchopneumonias, joint ill, puerperal and postpuerperal infections and salmonellosis;

Dogs and cats: bronchopneumonia, diarrhoea, dermatitis, otitis, Urinary tract infections and prostatitis;

Poultry (chickens, turkeys, quail pigeons, ornamental birds and others): mycoplasmosis, *E. coli* infections, chronic respiratory tract infections, salmonellosis, pasteurellosis and psittacosis.

Bacterial diseases in the rearing and keeping of stock and ornamental fishes can also be treated, the antibacterial spectrum extending beyond the abovementioned pathogens to further pathogens, such as, for example, Pasteurella, Brucella, Campylobacter, Listeria, Erysipelothrix, Corynebacteria, Borrelia, Treponema, Nocardia, Rickettsia and Yersinia.

The present invention includes pharmaceutical formulations which contain, in addition to non-toxic, inert pharmaceutically suitable excipients, one or more compounds according to the invention or consist of one or more active compounds according to the invention, and processes for the preparation of these formulations.

The present invention also includes pharmaceutical formulations in dosage units. This means that the formulations are present in the form of individual parts, for example tablets, coated tablets, capsules, pills, suppositories and ampoules, the active compound content of which corresponds to a fraction or a multiple of an individual dose. The dosage units can contain, for examples 1, 2, 3 or 4 individual doses or ½, 1/3 or ¼ of an individual dose. An individual dose preferably contains the/amount of active compound which is administered in one application and which usually corresponds to a whole, one half, one third or a quarter of a daily dose.

Non-toxic inert pharmaceutically suitable excipients are to be understood as solid, semi-solid or liquid diluents, fillers and formulation auxiliaries of all types.

Preferred pharmaceutical formulations which may be mentioned are tablets, coated tablets, capsules, pills, granules, suppositories, solutions, suspensions and emulsions, pastes, ointments, gels, creams, lotions, dusting powders and sprays.

Tablets, coated tablets, capsules, pills and granules can contain the active compound or compounds in addition to the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glgcerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, coated tablets, capsules, pills and granules can be provided with the. customary coatings and shells, optionally containing opacifying agents, and can also be of a composition such that they release the active compound or compounds only or preferentially in a certain part of the intestinal tract, if appropriate in a delayed manner, examples of embedding compositions which can be used being polymeric substances and waxes.

If appropriate, the active compound or compounds can also be present in microencapsulated form with one or more of the abovementioned excipients.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Dusting powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl, alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polgethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally or locally (dusting powder, ointment, drops) and for the therapy of infections in hollow spaces and body cavities. Possible suitable formulations are injection solutions, solutions and suspensions for oral therapy and gels, infusion formulations, emulsions, ointments or drops. Ophthalmological and dermatological formulations, silver salts and other salts, eardrops, eye ointments, dusting powders or solutions can be used for local therapy. In the case of animals, intake can also be in suitable formulations via the feed or drinking water. Gels, powders, dusting powders, tablets, delayed release tablets, premixes, concentrates, granules, pellets, boli, capsules, aerosols, sprays and inhalants can furthermore be used on humans and animals. The compounds according to the invention can moreover be incorporated into other carrier materials, such as, for example, plastics (chains of plastic for local therapy), collagen or bone cement.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place.

Thus in some cases it can suffice to manage with less than the abovementioned amount of active compound, while in other cases the abovementioned amount of active compound must be exceeded. The particular optimum dosage and mode of administration required for the active compounds can easily be determined by any expert on the basis of his expert knowledge.

The new compounds can be administered in the customary concentrations and formulations together with the feed or with feed formulations or with the drinking water. Infection by Gram-negative or Gram-positive bacteria can in this way be prevented, alleviated and/or cured and promotion of growth and an improvement in feed utilization can in this way be achieved.

The minimum inhibitory concentrations (MIC) were determined by the series dilution method on Iso-Sensitest agar (Oxoid). For each test substance, a series of agar plates which contained concentrations of the active compound which decreased by a dilution factor of two each time was prepared. The agar plates were inoculated with a multi-point inoculator (Denley). Overnight cultures of the pathogens which had first been diluted so that each inoculation point contained about $10^4$ colony-forming particles were used for the inoculation. The inoculated agar plates were incubated at 37° C. and the germ growth was read off after about 20 hours. The MIC value (μg/ml) indicates the lowest active compound concentration at which no germ growth was to be detected with the naked eye.

The MIC values of some of the compounds according to the invention are shown in comparison with ciprofloxacin in the following table.

| | MIC values (mg/l) determined by the agar dilution test (Denley multipoint inoculator; Iso-sensitest agar) | | | | | | | |
|---|---|---|---|---|---|---|---|---|
| Test strain | Example 1 | 2 | 3 | 4 | 5 | 8 | 9 | 10 |
| Escherichia coli Neumann | ≦0.015 | ≦0.015 | ≦0.015 | ≦0.015 | ≦0.015 | ≦0.015 | 0.25 | 0.125 |
| Proteus mirabilis 8223 | 1 | 4 | 1 | 0.5 | 2 | 2 | 8 | 16 |
| Proteus vulgaris 1017 | ≦0.015 | 0.125 | ≦0.015 | ≦0.015 | 0.03 | 0.06 | 0.5 | 1 |
| Morganella morganii 932 | ≦0.015 | 0.03 | 0.03 | ≦0.015 | ≦0.015 | 0.06 | 0.5 | 0.5 |
| Providencia-stuartei 12052 | 1 | 4 | 2 | 0.5 | 4 | 4 | 32 | 64 |
| Staphylococcus aureus FK | | | | | | | | |
| 422 | 0.06 | 0.125 | 0.06 | ≦0.015 | 0.125 | 0.03 | 0.06 | 0.125 |
| 1756 | 0.06 | 0.125 | 0.06 | ≦0.015 | 0.125 | 0.03 | 0.06 | 0.125 |
| 133 | 0.06 | 0.125 | 0.03 | ≦0.015 | 0.125 | 0.03 | 0.06 | 0.125 |
| Enterococcus faocalis | | | | | | | | |
| 27101 | 0.125 | — | 0.125 | 0.06 | 0.25 | 0.125 | 0.25 | 2 |
| 9790 | 0.125 | 0.5 | 0.25 | 0.06 | 0.25 | 0.125 | 0.25 | 2 |
| Test strain | Example 13 | 14 | 15 | 16 | 17 | 18 | Ciprofloxacin | |
| Escherichia coli Neumann | 0.06 | 0.06 | ≦0.015 | 0.06 | 0.125 | 0.03 | ≦0.015 | |
| Proteus mirabilis 8223 | 1 | 4 | 0.5 | 4 | 8 | 1 | 1 | |
| Proteus vulgaris 1017 | 0.03 | 0.5 | 0.03 | 0.06 | 0.5 | 0.06 | ≦0.015 | |
| Morganella morganii 932 | 0.125 | 0.25 | 0.03 | 0.06 | 0.5 | 0.06 | ≦0.015 | |
| Providencia-stuartei 12052 | 2 | 4 | 1 | 32 | 8 | 4 | 4 | |
| Staphylococcus aureus FK | | | | | | | | |
| 422 | 0.06 | 0.25 | 0.03 | 0.125 | 0.5 | 0.125 | 0.25 | |
| 1756 | 0.06 | 0.25 | 0.03 | 0.125 | 0.5 | 0.125 | 0.25 | |
| 133 | 0.06 | 0.25 | 0.03 | 0.125 | 0.5 | 0.125 | 0.25 | |
| Enterococcus faecalis | | | | | | | | |
| 27101 | 0.215 | 0.25 | 0.03 | 0.5 | 1 | 0.25 | 0.05 | |
| 9790 | 0.25 | 0.5 | — | 0.5 | 2 | 0.5 | 0.25 | |

The following examples illustrate the invention:
Preparation of the intermediate products:

Example A tert.-Butyl N-(cis-4-methoxy-pyrrolidin-3-yl)-carbamate a) trans-1-Benzyl-3-hydroxy-4-methoxypyrrolidine 34.9 g (0.2 mol) of 3-benzyl-6-oxa-3-azabicyclo[3.1.0] hexane (U.S. Pat. No. 4,0254,135) are heated with 3.6 g (20 mmol) of sodium methylate solution (30% strength) at 120° C. in 200 ml of absolute methanol in an autoclave for 10 hours. After cooling, the mixture is neutralized with 1.2 g (20 mmol) of acetic acid and the solvent is removed on a rotary evaporator. The residue is taken up in tetrahydrofuran and the sodium acetate is filtered off. The filtrate is concentrated and the residue is distilled.

Yield: 40.9 g (91% of theory)
Boiling point: 112°–116° C./0.1 mbar
Content: 92% pure b) cis-3-Amino-1-benzyl-4-methoxy-pyrrolidine 5.6 g (25 mmol) of trans-1-benzyl-3-hydroxy-4-methoxy-pyrrolidine and 8.6 g (33 mmol) of triphenylphosphine are initially introduced into 40 ml of absolute tetrahydrofuran and a solution of 6 g (34 mmol) of diethyl azodicarboxylate in 40 ml of absolute tetrahydrofuran is added dropwise at 0° C. 3.9 g (27 mmol) of phthalimide are then added in small portions at 0° C. in the course of one hour. The mixture is stirred at room temperature overnight and concentrated. The residue is dissolved in 80 ml of ethyl acetate and 80 ml of petroleum ether are added. The mixture is left to crystallize out overnight and the crystals (triphenylphosphine oxide and diethyl hydrazine-dicarboxylate) are filtered off. The filtrate is concentrated and the residue is heated under reflux With 60 ml of concentrated hydrochloric acid overnight. The undissolved residues are decanted and the solution is concentrated. The residue is taken up in a little water and the solution is rendered alkaline with solid potassium carbonate and extracted five times with 50 ml of chloroform. The extract is dried over potassium carbonate and concentrated and the residue is distilled.

Yield: 3.4 g (65.9% of theory)

Boiling point: 95° C./0.2 mbar c) tert.-Butyl N-(cis-1-benzyl-4-methoxypyrrolidin-3-yl)-carbamate 3 g (14.5 mmol) of cis-3-amino-1-benzyl-4-methoxy-pyrrolidine and 11 ml of tert.-butanol are added to a solution of 0.65 g of NaOH in 8 ml of water. 3.5 g (16 mmol) of di-tert.-butyl dicarbonate are added dropwise. The mixture is stirred at room temperature overnight, the inorganic salts are filtered off with suction and the filtrate is extracted with chloroform. The extract is dried over potassium carbonate and concentrated and the residue is distilled.

Yield: 3.8 g (85.5% of theory)

Boiling point: 130°–140° C./0.05 mbar d) tert.-Butyl N-(cis-4-methoxypyrrolidin-3-yl)-carbamate 3.5 g (11.4 mmol) of tert.-butyl N-(cis-1-benzyl-4-methoxypyrrolidin-3-yl)-carbamate are hydrogenated in 100 ml of methanol on 2 g of palladium-on-active charcoal (10% of Pd) at 100° C. under 100 bar. The catalyst is filtered off, the filtrate is concentrated and the residue is distilled.

Yield: 1.9 g (81.6% of theory)

Boiling point: 84° C./0.1 mbar

Example B tert.-Butyl N-(trans-4-methoxy-pyrrolidin-3-yl) carbamate a) trans-3-Amino-1-benzyl-4-methoxy-pyrrolidine 27 g (0.41 mol) of sodium azide are dissolved in 50 ml of water, and 17.5 g (0.1 mol) of 3-benzyl-6-oxa-3-azabicyclo[3.1.0]hexane in 300 ml of dioxane are added. The mixture is heated under reflux for 72 hours and concentrated, the inorganic salts are dissolved in water and the mixture is extracted with chloroform. The extract is dried over potassium carbonate and concentrated. The residue is dissolved in 50 ml of absolute tetrahydrofuran and the solution is added dropwise to 4 g of sodium hydride (80% strength in paraffin oil) in 200 ml of absolute tetrahydrofuran. The mixture is heated under reflux for one hour and 15 g (0.1 mol) of methyl iodide are then added dropwise. The mixture is subsequently heated under reflux overnight and concentrated, the residue is taken up in water and the mixture is extracted with chloroform. The extract is dried over potassium carbonate and concentrated and the residue is distilled. 13.1 g of a material which is 73% pure according to the gas chromatogram are obtained. 12.7 g of this material in 40 ml of absolute tetrahydrofuran are added dropwise to a suspension of 4 g of lithium aluminum hydride in 150 ml of absolute tetrahydrofuran and the mixture is heated under reflux for 2 hours. Excess lithium aluminum hydride is decomposed by careful dropwise addition of 4 ml portions of water and 15% strength potassium hydroxide solution and again 4 ml of water. The inorganic salts are filtered off with suction and washed several times with chloroform. The organic phases are dried over potassium carbonate and concentrated and the residue is distilled.

Yield: 9 g (32.8% of theory)

Boiling point: 91° C./0.07 mbar

The product has a content of 75%, determined by gas chromatography (area method).

b) tert.-Butyl N-(trans-1-benzyl-4-methoxypyrrolidin-3-yl)carbamate 8.2 g (30 mmol) of trans-3-amino-1-benzyl-4-methoxy-pyrrolidine and 21 ml of tert.-butanol are added to a solution of 1.3 g of NaOH in 15 ml of water. 7.1 g (31 mmol) of di-tert.-butyl dicarbonate are added dropwise and the mixture is then stirred at room temperature overnight. Inorganic salts are filtered off with suction, the filtrate is extracted with chloroform, the extract is dried over potassium carbonate and concentrated and the residue is distilled.

Yield: 7.7 g (84.4% of theory)

Boiling point: 148° C./0.1 mbar

Melting point: 88°–90° C.

c) tert.-Butyl N-(trans-4-methoxypyrrolidin-3-yl) carbamate 6.7 g (22 mmol) of tert.-butyl N-(trans-1-benzyl-4-methoxypyrrolidin-3-yl)carbamate are hydrogenated in 150 ml of methanol on 2 g of palladium-on-active charcoal (10% of Pd) under 100 bar at 100° C. The catalyst is filtered off with suction, the filtrate is concentrated and the residue is distilled.

Yield: 2.2 g (46% of theory)

Boiling point: 94° C./0.05 mbar

Example C trans-3-Amino-4-hydroxy-pyrrolidine a) trans-3-Amino-1-benzyl-4-hydroxy-pyrrolidine 8.9 g (50 mmol) of 3-benzyl-6-oxa-3-azabicyclo[3.1.0]hexane are heated in 75 ml of ammonia solution (25% strength) at 120° C. in an autoclave for 8 hours. The solution is concentrated and the residue is distilled.

Yield: 6 g (62.4% of theory)

Boiling point: 130°–140° C./0.1 bar

Melting point: 82°–84° C.

b) trans-3-Amino-4-hydroxy-pyrrolidine 5.2 g. (27 mol) of trans-3-amino-1-benzyl-4-hydroxypyrrolidine are hydrogenated in 40 ml of methanol on 1 g of palladium-on-active charcoal (10% of Pd) at 100° C. under 100 bar. The catalyst is filtered off with suction, the filtrate is concentrated and the residue is distilled.

Yield: 1 g (36.3% of theory)

Boiling points 110° C./0.3 mbar

Example D trans-4-Hydroxy-3-(2-hydroxyethylamino)-pyrrolidine a) trans-1-Benzyl-4-hydroxy-3-(2-hydroxyethylamino)pyrrolidine 40 g (0.22 mol) of 3-benzyl-6-oxa-3-azabicyclo[3.1.0]hexane are heated under reflux with 42 g (0.68 mol) of 2-aminoethanol in 450 ml of water overnight. The solution is extracted once with tert.-butyl methyl ether and the aqueous phase is concentrated, The residue is distilled.

Yield: 34.1 g ( 65.6% of theory)

Boiling point: 190° C./0.1 mbar b) trans,4-Hydroxy-3-(2-hydroxyethylamino)-pyrrolidine trans-1-Benzyl-4-hydroxy-3-(2-hydroxyethylamino)-pyrrolidine is hydrogenated analogously to Example C b) to give the reaction product as an oil.

EXAMPLE E trans-4-Hydroxy-3-(2-hydroxyethyl-methyl-amino)pyrrolidine a) trans-1-Benzyl-4-hydroxy-3-(2-hydroxyethyl-methylamino)-pyrrolidine 17.5 g (0.1 mol ) of 3-benzyl-6-oxa-3-azabicyclo[3.1.0]-hexane are reacted with 17 g (0.1 mol ) of methylaminoethanol in 200 ml of water analogously to Example D a).

Yield: 18.2 g (73% of theory )

Boiling point: 180°–190° C./0.1 mbar b) trans-4-Hydroxy-3-(2-hydroxyethyl-methyl-amino)pyrrolidine trans-1-Benzyl-4-hydroxy-3-(2-hydroxyethyl-methylamino)pyrrolidine is hydrogenated analogously to Example C b) to give the reaction product as an oily compound.

EXAMPLE F

2-Oxa-5,8-diazabicyclo[4.3.0]nonane dihydrochloride a) 8-Benzyl-2-oxa-5,8-diazabicyclo[4.3.0]nonane 15.6 g (66 mmol) of 1-benzyl-4-hydroxy-3-(2-hydroxyethyl-amino)pyrrolidine are heated under reflux in a mixture of 60 ml of concentrated sulphuric acid and 20 ml of water for 6 hours. The mixture is rendered alkaline with concentrated sodium hydroxide solution, the sodium sulphate which has precipitated is filtered off with suction and the filtrate is extracted with chloroform. The extract is dried over potassium carbonate and concentrated and the residue is distilled.

Yield: 4.1 g (28.5% of theory)

Boiling point: 122°–128° C. (0.08 mbar )

b) 2-Oxa-5,8-diazabicyclo[4.3.0]nonane dihydrochloride

A solution of 4 g (18.2 mmol) of 8-benzyl-2-oxa-5,8-diazabicyclo[4.3.0]nonane in 100 ml of methanol and 3.5 ml of concentrated hydrochloric acid is hydrogenated on 2 g of palladium-on-active charcoal (10% of Pd) at 80° C. under 100 bar. The catalyst is filtered off and washed with water. The filtrates are concentrated and the product is crystallized by trituration with a little methanol. The crystals are filtered off with suction, washed with acetone and dried in air.

Yields 1.85 g (51% of theory)

Melting points 280° C. with decomposition c) 2-Oxa-5,8-diazabicyclo[4.3.0]nonane 7.2 g (33 mmol) of 8-benzyl-2-oxa-5,8-diazabicyclo-[4.3.0]nonane are hydrogenated in 400 ml of methanol with 2.5 g of palladium-on-active charcoal (10% of Pd) under 50 bar at 100° C. The catalyst is filtered off with suction, the filtrate is concentrated and the residue is distilled.

Yields 3.1 g (73.4% of theory)

Boiling points 58° C./9.1 mbar.

d) trans-2-Oxa-5,8-diazabicyclo/4.3.0/nonane

3-Benzyl-6-oxa-3-azabicyclo[3.1.0]hexane is reacted with 2-(benzylamino)-ethanol, analogously to Example D a), to give trans-1-benzyl-3-[N-benzyl-N-(2-hydroxy-ethyl)-amino]-4-hydroxypyrrolidine which is then reacted analogously to Example F a) to give 5,8-dibenzyl-2-oxa-5,8-diazabicyclo[4.3.0]nonane which is purified by chromatography (silica gel, cyclohexane/tert.-butyl methyl ether/ethyl acetate 1:1:1).

The hydrogenolytic debenzylation is carried out analogously to Example F c) to give trans-2-oxa-5,8-diazabicyclo [4.3.0]-nonane, boiling point: 60° C./0.1 mbar.

EXAMPLE G

5-Methyl-2-oxa-5,8-diazabicyclo[4.3.0]nonane dihydrochloride a) 8-Benzyl-5methyl-2-oxa-5,8-diazabicyclo[4.3.0]nonane 18 g (71.9 mmol) of 1-benzyl-4-hydroxy-3-(2-hydroxyethyl-methyl-amino)-pyrrolidine are reacted in 60 ml of concentrated sulphuric acid and 30 ml of water as in Example F a).

Yield:. 10 g (60% of theory)

Boiling point: 122° C./0.08 mbar b) 5-Methyl-2-oxa-5,8-diazabicyclo[4.3.0]nonane dihydrochloride A solution of 9.4 g (40 mmol) of 8-benzyl-5-methyl-2-oxa-5,8-diazabicyclo[4.3.0]nonane in 150 ml of methanol and 7.4 ml of concentrated hydrochloric acid is hydrogenated on 3 g of palladium-on-active charcoal (10% of Pd) at 80° C. under 100 bar. The catalyst is filtered off with suction and the filtrate is concentrated. The residue is triturated with butanol/acetone 1:1 and the crystals are filtered off with suction and dried over $P_4O_{10}$ in a desiccator. The product is very hygroscopic.

Yield: 8.2 g (95% of theory)

Mass spectrum: m/e 142 ($M^+$), 112 ($M^+$—$CH_2O$), 100 ($M^+$—$CH_2$—$N=CH_2$), 82 ($C_4H_4NO^+$), 68 ($C_4H_6N^+$)

EXAMPLE H

2-Methyl-3-oxa-2,7-diazabicyclo[3.3.0]octane a) Ethyl N-(2,2-dimethoxyethyl-carbamate 214 g (2 mol) of ethyl chloroformate are added dropwise to 214 g (2 mol) of aminoacetaldehyde dimethyl acetal in 1 l of toluene and 90 g of NaOH in 500 ml of water at 10° C. The mixture is stirred at room temperature for a further 2 hours and the aqueous phase is separated off, saturated with sodium chloride and extracted with toluene. The toluene solutions are dried over magnesium sulphate and concentrated and the residue is distilled.

Yield: 338 g (95.4% of theory)

Boiling point: 60° C./0.03 mbar b) Ethyl N-allyl-N-(2,2-dimethoxyethyl)-carbamate 20 g of sodium hydride (80% strength in paraffin oil) are initially introduced into 500 ml of toluene and 89 g (0.5 mol) of ethyl N-(2,2-dimethoxyethyl)-carbamate are added dropwise at 80° C. The mixture is stirred at 80° C. for one hour and 73 g (0.6 mol) of allyl bromide are then added dropwise in the course of three hours. The mixture is stirred at 80° C. overnight, the salts are dissolved with water and the organic phase is separated off. The aqueous phase is extracted with toluene, the organic phases are dried over potassium carbonate and concentrated and the residue is distilled.

Yield: 68 g (62.5% of theory)

Boiling point: 65° C./0.09 mbar c) Ethyl N-allyl-N-(2-oxoethyl)-carbamate 68 g (0.313 mol) of ethyl N-allyl-N-(2,2-dimethoxyethyl)-carbamate are heated with 150 ml of formic acid at 100° C. for one hour. The mixture is poured onto ice and extracted several times with methylene chloride, the organic phases are washed with sodium bicarbonate solution, dried over magnesium sulphate and concentrated and the residue is distilled.

Yield: 46.7 g (87.2% of theory)

Boiling point: 58° C./0.09 mbar d) Ethyl 2-methyl-3-oxa-2,7-diazabicyclo[3.3.0]octane-7-carboxylate 10 g (0.12 mol) of methylhydroxylamine hydrochloride are dissolved in 50 ml of methanol, the solution is cooled in an ice-bath and 22 g (0.12 mol) of 30% strength sodium methylate solution in methanol are added dropwise. The sodium chloride is filtered off with suction and the salt is washed with 80 ml of toluene. The methylhydroxylamine solution is added dropwise in the course of one hour to 20 g (0.117 mol) of ethyl N-(2-(oxoethyl)-carbamate, which is heated under reflux in 160 ml of toluene, using a water separator. The mixture is heated under reflux overnight and the product is extracted twice with 80 ml of 10% strength hydrochloric acid each time. The hydrochloric acid solutions are saturated with potassium carbonate and extracted six times with 200 ml of chloroform each time. The extract is dried over $K_2CO_3$ and concentrated and the residue is distilled.

Yield: 18.6 g (79.5% of theory)

Melting point: 93° C./0.09 mbar e) 2-Methyl-3-oxa-2,7-diazabicyclo[3.3.0]octane 13 g (65 mmol) of ethyl 2-methyl-3-Oxa-2,7-diazabicyclo[3.3.0]octane-7-carboxylate are heated under reflux in 300 ml of water with 41 g of $Ba(OH)_2 \cdot 8H_2O$ overnight.

Potassium carbonate is added, the barium carbonate which has precipitated out is filtered off with suction and the filtrate is extracted ten times with 100 ml of chloroform each time. The extract is dried over potassium carbonate and concentrated and the residue is distilled.

Yield: 5.4 g (65% of theory)

Boiling point: 80° C./10 mbar

EXAMPLE I

1-Methyl-octahydropyrrolo[3,4-b]pyrrole (2-methyl-2,7-diazabicyclo[3.3.0]octane)

a) 1-Benzyl-3-(2-chloroethyl-methyl-amino)-pyrrolidine-2,5-dione 74.8 g (0.4 mol) of N-benzylmaleimide [Arch. Pharm. 308, 489 (1975)] and 52.0 g (0.4 mol) of 2-chloroethylmethylamine hydrochloride are initially introduced into 400 ml of dioxane and 40.4 g (0.4 mol) of triethylamine are added dropwise at 20° C. The mixture is then boiled under reflux for 5 hours. The batch is subsequently poured into 2 l of ice-water and extracted with 3 portions of 400 ml of chloroform and the extract is washed with water, dried over sodium sulphate and concentrated on a rotary evaporator. Chromatography of the residue (101.1 g) on silica gel using ethyl acetate:petroleum ether (1:2) gives 56.8 g (51% of theory) of an oil.

$R_F$ value: 0.33 (silica gel, ethyl acetate/petroleum ether= 1:2), b) 5-Benzyl-4,6-dioxo-1-methyl-octahydropyrrolo[3,4-b]-pyrrole 7.2 g (0.24 mol) of an 80% strength sodium hydride suspension in mineral oil are suspended in 150 ml of absolute dimethylformamide (dried over calcium hydride), and 62 g (0.22 mol) of 1-benzyl-3-(2-chloroethyl-methyl-amino)-pyrrolidine-2,5-dione are added dropwise as a solution in 50 ml of absolute dimethylformamide at room temperature. During this, an exothermic reaction takes place with foaming. The mixture is diluted with a further 50 ml of absolute dimethylformamide and subsequently stirred at room temperature for 1 hour and is then poured into ice-water and extracted with methylene chloride. The extract is washed with water, dried with sodium sulphate and concentrated on a rotary evaporator. The residue is chromatographed on silica gel using ethyl acetate:petroleum ether, initially (1:2) and later(1:1). 16.4 g of educt are initially recovered here, and 17.2 g (44% of theory, based on the educt reacted) of an oily product are then isolated.

$R_f$ value=0.26 (silica gel, ethyl acetate:petroleum ether= 1:1).

c) 5-Benzyl-1-methyl-octahydropyrrolo[3,4-b]pyrrole 1.52 g (40 mmol) of lithium aluminum hydride are initially introduced into 30 ml of anhydrous tetrahydrofuran, and 4.9 g (20 mmol) of 5-benzyl-4,6-dioxo-1-methyl-octahydropyrrolo[3,4-b]pyrrole are added dropwise as a solution in 15 ml of anhydrous tetrahydrofuran. The mixture is then subsequently stirred at the boiling point for 3 hours. 1.5 ml of water, 1.5 ml of 15% strength potassium hydroxide solution and 4.5 ml of water are added dropwise in succession to the batch and the precipitate is then filtered off with suction and washed with tetrahydrofuran. The filtrate is concentrated on a rotary evaporator and the residue is distilled. 3.1 g (72% of theory) of a colorless distillate of boiling point 80° C./0.07 mbar are obtained.

d) 1-Methyl-octahydropyrrolo[3,4-b]pyrrole 6.49 g (30 mmol) of 5-benzyl-1-methyl-octahydropyrrolo[3,4-b]pyrrole are dissolved in 100 ml of absolute ether, and 5.2 g of hydrogen chloride dried over phosphorus pentoxide are passed in. The hydrochloride suspension formed is concentrated in vacuo and the residue is taken up in 100 ml of methanol. It is then hydrogenated with 2 g of Pd-on-C (5% strength) at 80° C. under 50 bar for 4 hours. The catalyst is subsequently filtered off, the filtrate is concentrated and 30 ml of 40% strength sodium hydroxide solution and 50 ml of ether are added to the residue. The ethereal phase is separated off and the aqueous phase is extracted with 2×50 ml of ether. The combined organic phases are dried over sodium sulphate and concentrated and the residue is distilled. 1.3 g (34% of theory) of a colorless oil of boiling point 65°–66° C./12 mbar are obtained.

Purity=>99%

EXAMPLE J

Octahydropyrrolo[3,4-b]pyrrole (2,7-diazabicyclo[3.3.0] octane)

a) 1-Benzyl-3-2-chloroethylamino)-pyrrolidine-2,5-dione 74.8 g (0.4 mol) of N-benzylmaleimide are reacted with 58 g (0.5 mol) of 2-chloroethylamine hydrochloride and 50.5 g (0.5 mol) of triethylamine in accordance with the working instructions of Example Ia. After working up by chromatography, 81.6 g (77% of theory) of an oil with an $R_F$ value of 0.24 (on silica gel using ethyl acetate: petroleum ether=1:1) are obtained.

b) 5-Benzyl-4,6-dioxo-octahydropyrrolo[3,4-b]pyrrole 17.4 g (0.58 mmol) of sodium hydride suspension are reacted with 119 g (0.45 mol) of 1-benzyl-3-(2-chloroethylamino)-pyrrolidine-2,5-dione in 550 ml of absolute dimethylformamide in accordance with the working instructions of Example Ib. After the mixture has been left to stand overnight, it is worked up under aqueous conditions. On purification by chromatography, impurities are first eluted with ethyl acetate and the product is then eluted with ethyl acetate:methanol (3:1) ($R_F$ value 0.55) 57.7 g of product (56% of theory) are isolated.

c) 5-Benzyl-octahydropyrrolo[3,4-b]pyrrole 57.7 g (0.25 mol) of crude 5-benzyl-4,6-dioxo-octahydropyrrolo[3,4-b]pyrrole are reduced with 21.4 g (0.56 mol) of lithium aluminum hydride by boiling in 700 ml of absolute tetrahydrofuran for 10 hours in accordance with the working instructions of Example Ic. Working up by distillation gives 21.0 g (41.1% of theory) of an oil of boiling point 95° C./0.1 mbar.

d) Octahydropyrrolo[3,4-b]pyrrole 21.0 g (0.104 mol) of 5-benzyl-octahydropyrrolo[3,4-b]pyrrole are initially introduced into 180 ml of ice-cooled methanol, and 17.3 ml (0.208 mol) of concentrated hydrochloric acid are added. The mixture is then hydrogenated with 2 g Of Pd-on-C (5% strength) at 90° C. under 100 bar for 4 hours. The catalyst is filtered off, 37.4 g (0.208 mol) of 30% strength sodium methylate solution are added to the filtrate, the mixture is filtered again and the filtrate is concentrated. The residue is distilled through a small Vigreux column. 5.6 g of a colorless oil (48% of theory) of boiling point 93°–95° C./30mbar, which fumes in air and slowly solidifies in the receiver (melting point 40° C.) are obtained.

EXAMPLE K

Octahydropyrrolo[3,4-b]pyridine (2,8-diazabicyclo[4.3.0]nonane)

a) 6-Benzyl-5,7-dioxo-octahydropyrrolo[3,4-b]pyridine 47.6 g (0.2 mol) of pyridine-2,3-dicarboxylic acid N-benzylimide (British Patent 1,086,637; Chem. Abstr. 68, 95695w) are hydrogenated in 400 ml of glycol monomethyl ether over 15 g of ruthenium-on-active charcoal (5% strength) at 90° C. under 100 bar until the calculated amount of hydrogen has been taken up. The catalyst is then filtered off and the filtrate is concentrated on a rotary evaporator. 44 g of an oily crude product are obtained.

The corresponding hydrogenation with palladium-on-active charcoal (5% strength) gives a quantitative yield of a pure product of melting point 67°–69° C.

b) 6-Benzyl-octahydropyrrolo[3,4-b]pyridine 44 g (about 0.18 mol ) of crude or pure 6-benzyl-5,7-dioxo-octahydropyrrolo[3,4-b]pyridine are reduced with 15.2 g (0.40 mol ) of lithium aluminum hydride in 390 ml of absolute tetrahydrofuran in the course of 10 hours in accordance ,with the working instructions of Example Ic. 24.4 g of a colorless oil having a boiling point of 93°–95° C./0.06 mbar are obtained on distillation.

c) Octahydropyrrolo[3,4-b]pyridine 69 g (0.32 mol) of 6-benzyl-octahydropyrrolo[3,4-b]pyridine are hydrogenated in 450 ml of methanol over 7 g of palladium-on-active charcoal (5% strength) at 90° C./90 bar in the course of 3 hours. The catalyst is then filtered off, the filtrate is concentrated and the residue is distilled. 33.8 g (84% of theory) of a colorless solid having a melting point of 65°–67° C. and a boiling point of 78° C./9 mbar are obtained.

EXAMPLE L

1-Methyl-octahydropyrrolo[3,4-b]pyridine (2-methyl-2,8-diazabicyclo[4.3.0]nonane)

a) 1-Methyl-pyridinium-2,3-dicarboxylic acid N-benzylimide iodide 190.5 g (0.8 mol) of pyridine-2,3-dicarboxylic acid N-benzylimide are dissolved in 800 ml of nitromethane, while heating, and 136 g (0.96 mol) of methyl iodide are added dropwise. The mixture is then boiled for 8 hours while cooling under reflux (cooling water 0° C.). After cooling, the solid is filtered off with suction and washed with methylene chloride. 123 g of dark red crystals having a melting point of 162°–165° C. (decomposition) are obtained.

b) 6-Benzyl-1-methyl-5,7-dioxo-octahydropyrrolo[3,4-b]pyridine 38 g (0.1 mol) of 1-methyl-pyridinium-2,3-dicarboxylic acid N-benzylimide iodide are hydrogenated over 1 g of platinum oxide in 450 ml of glycol monomethyl ether at 30° C. under 70 bar until the uptake of hydrogen has ended (51 hours). The catalyst is filtered off, the filtrate is concentrated, the residue is taken up in 300 ml of chloroform and the solution is washed 2× with 300 ml of 10% strength sodium carbonate solution each time and with 300 ml of water. After drying over sodium sulphate, it is concentrated 27 g of an oily residue remain.

c) 6-Benzyl-1-methyl-octahydropyrrolo[3,4-b]pyridine 19.2 g (0.08 mol) of crude 6-benzyl-1-methyl-5,7-dioxooctahydropyrrolo[3,4-b]pyridine are reduced with 6.1 g (0.16 mol ) of lithium aluminum hydride in absolute tetrahydrofuran in accordance with the working instructions of Example Ic.

Yield: 9.5 g (52% of theory),

Boiling point: 93°–96° C./0.1 mbar.

d) 1-Methyl-octahydropyrrolo[3,4-b]pyridine 11.7 g (54 mmol) of 6-benzyl-1-methyl-octahydropyrrolo[3,4-b]pyridine as the dihydrochloride are hydrogenated in 100 ml of methanol over palladium-on-active charcoal in accordance with the working instructions of Example Id. Working up by distillation gives 2.6 g (34% of theory) of a colorless oil of boiling point 83°–85°/12 mbar).

EXAMPLE M trans-4-Methoxy-3-methylamino-pyrrolidine dihydrochloride a) trans-1-Benzyl-3-benzylmethylamino-4-hydroxypyrrolidine 19.4 g (0.1 mol) of 90% strength 3-benzyl-6-oxa-3-azabicyclo[3.1.0]hexane are heated under reflux with 14.5 g (0.12 mol) of benzylmethylamine in 100 ml of dioxane and 200 ml of water overnight. The mixture is extracted with $CHCl_3$, the extracts are dried with $K_2CO_3$ and concentrated and the residue is subjected to incipient distillation up to 160° C. (oil bath temperature).

Crude yield: 18.3 g

Content: 100% (determined by gas chromatography)

b) trans-1-Benzyl-3-benzylmethylamino-4-methoxypyrolidine 17.3 g (58 mmol) of crude trans-1-benzyl-3-benzyl-methylamino-4-hydroxy-pyrrolidine in 80 ml of absolute tetrahydrofuran are added dropwise to 2.8 g (93.3 mmol) of 80% strength sodium hydride in 40 ml of absolute tetrahydrofuran and the mixture is heated under reflux at the same time. When the evolution of hydrogen has ended, 8.7 g (61 mmol) of methyl iodide are added dropwise and the mixture is then heated under reflux overnight. It is poured into ice-water and extracted with toluene, the extracts are dried with $K_2CO_3$ and concentrated and the residue is distilled.

Yield: 9.7 g (52% of theory)

Boiling point: 140°–150° C./0.1 mbar c) trans-4-Methoxy-3-methyl amino-pyrrolidine dihydrochloride 9.3 g (29 mmol) of trans-1-benzyl-3-benzylmethylamino-4-methoxy-pyrrolidine are dissolved in 100 ml of methanol, 4.8 ml of concentrated hydrochloric acid are added and the mixture is hydrogenated on 4 g of 10% strength Pd-on-active charcoal at 90° C. under 100 bar. The catalyst is filtered off with suction, the filtrate is concentrated and the residue is recrystallized from isopropanol/methanol.

Yield: 3.7 g (62.8% of theory)

Melting points: 157°–162° C.

EXAMPLE N 2,5-Dimethyl-3-oxa-2,7-diazabicyclo[3.3.0 ]octane a) N-(2-Methylprop-2-enyl)-N-(2,2-dimethoxyethyl)urethane 89 g (0.5 mol) of N-(2,2-dimethoxyethyl)-urethane are added dropwise to 20 g of sodium hydride (80% strength) in 500 ml of absolute toluene at 90° C. When no further hydrogen is formed, 54 g (0.6 mol ) of methallyl chloride are added dropwise and the mixture is stirred overnight at 90° C. The sodium chloride which has precipitated out is dissolved with a little water, the organic phase is separated off, dried over $K_2CO_3$ and concentrated and the residue is distilled.

Yield: 71.3 g (61.7% of theory)
Boiling point: 60° C./0.08 mbar b) N-(2-Methylprop-2-enyl)-N-(2-oxoethyl)-urethane 11.5 g (50 mmol) of N-(2-methylprop-2-enyl)-N-(2,2-dimethoxyethyl)-urethane and 1.25 g (5 mmol) of pyridinium p-toluenesulphate in 100 ml of acetone and 10 ml of water are heated under reflux for two days. The mixture is concentrated and the residue is distilled.

Yield: 5.3 g (61.2% of theory)
Boiling point: 73° C./0.1 mbar c) Ethyl 2,5-dimethyl-3-oxa-2,7-diazabicyclo[3.3.0]-octane-7-carboxylate 21.7 g of 30% strength sodium methylate solution are added dropwise to 10 g (0.12 mol) of N-Methylhydroxylamine hydrochloride in 26 ml of methanol. The sodium chloride is filtered off with suction and washed with 8 ml of methanol and 80 ml of toluene. This solution is added dropwise to 19.2 g (0.11 mol) of N-(2-methyl-prop-2-enyl)-N-(2-oxoethyl)-urethane, which is heated under reflux in 160 ml of toluene using a water separator. The mixture is heated under reflex overnight, the product is extracted with 160 ml of 10% strength hydrochloric acid and the hydrochloric acid solution is rendered alkaline with potassium carbonate and extracted with six portions, of 200 ml of $CHCl_3$. The extracts are dried over $K_2CO_3$ and concentrated and the residue is distilled.

Yield: 13 g (55% of theory)
Boiling point: 88°–95° C./0.08 mbar d) 2,5-Dimethyl-3-oxa-2,7-diazabicyclo[3.3.0]octane 13 g (60.6 mmol ) of ethyl 2,5-dimethyl-3-oxa-2,7-diazabicyclo[3.3.0]octane-7-carboxylate are heated under reflux with 33 g of $Ba(OH)_2 \cdot 8H_2O$ in 330 ml of water overnight. The $BaCO_3$ is filtered off with suction, $K_2CO_3$ is added to the filtrate, the solid is filtered off with suction again and the filtrate is extracted ten times with 100 ml of $CHCl_3$ each time. The extracts are dried over $K_2CO_3$ and concentrated and the residue is distilled.

Yield: 5.9 g (63.7% of theory)
Boiling point: 64° C./5 mbar

EXAMPLE O 2,8-Dimethyl-3-oxa-2,7-diazabicyclo[3.3.0]octane a) N-(1,1-Dimethoxyprop-2-yl)-urethane 80 g (0.73 mol) of ethyl chloroformate are added dropwise to 86.2 g (0.72 mol) of 2-aminopropionaldehyde dimethyl acetal in 350 ml of toluene and 32 g (0.8 mol) of NaOH in 300 ml of water. The mixture is stirred at room temperature for a further 2 hours, the organic phase is separated off, the aqueous phase is extracted with toluene and the toluene solutions are dried over $K_2CO_3$. The solution is concentrated and the residue is distilled.

Yield: 132 g (95% of theory)
Boiling point: 55° C./0.06 mbar b) N-Allyl-N-(1,1-dimethoxyprop-2-yl)-urethane 131 g (0.686 mol) of N-(1,1-dimethoxyprop-2-yl)-urethane are added dropwise to 25 g of sodium hydride (80% strength) in 700 ml of absolute toluene at 90° C. When the evolution of hydrogen has ended, 61.2 g (0.8 mol) of allyl chloride are added dropwise at 90° C. and the mixture is stirred overnight at 90° C. The sodium chloride which has precipitated out is dissolved with water, the organic phase is separated off, dried over $K_2CO_3$ and concentrated and the residue is distilled.

Yield: 78 g (31.7% of theory)
Boiling point: 62°–69° C./0.06 mbar.
Content: 64.5% pure (determined by gas chromatography)

c) N-Allyl-N-(1-oxoprop-2-yl)-urethane 76.5 g (0.213 mol) of 64.5% pure N-allyl-N-(1,1-dimethoxyprop-2-yl)-urethane are heated in 180 ml of formic acid at 100° C. for one hour. The mixture is poured into ice-water and extracted with $CH_2Cl_2$, the extracts are washed neutral with $NaHCO_3$ solution, dried over $MgSO_4$ and concentrated and the residue is distilled.

Yield: 36 g (80.9% of theory)
Boiling point: 97°–102° C./8 mbar
Contents 88.8% pure (determined by gas chromatography)

d) Ethyl 2,8-dimethyl-3-oxa-2,7-diazabicyclo[3.3.0]-octane-7-carboxylate

A methanolic methylhydroxylamine solution is prepared from 16.4 g (0.2 mol) of N-methylhydroxylamine hydrochloride in 33 ml of absolute methanol and 36 g (0.2 mol) of 30% strength sodium methylate solution, and the solution formed is diluted with 130 ml of toluene and added dropwise to 354 g (0.17 mol) of N-allyl-N-(1-oxoprop-2-yl)-urethane in 250 ml of toluene, which is heated under reflux using a water separator. The mixture is heated under reflux overnight, the product is extracted with dilute hydrochloric acid and the hydrochloric acid solution is rendered alkaline with $K_2CO_3$ and extracted with $CHCl_3$. The extract is dried over $K_2CO_3$ and concentrated and the residue is distilled.

Yield: 18.5 g (50.8% of theory)
Boiling point: 95°–105° C./0.1 mbar e) 2,8-Dimethyl-3-oxa-2,7-diazabicyclo[3.3.0]octane 9.2 g (42.9 mmol) of ethyl 2,8-dimethyl-3-oxa-2,7-diazabicyclo[3.3.0]octane-7-carboxylate are heated under reflhx with 23.5 g of $Ba(OH)_2 \cdot 8H_2O$ in 235 ml of water overnight. The $BaCO_3$ is filtered off with suction, $K_2CO_3$ is added to the filtrate and the solid is filtered off with suction again. The filtrate is extracted ten times with 50 ml of $CHCl_3$ each time, the extracts are dried over $K_2CO_3$ and concentrated and the residue is distilled.

Yield: 1.7 g
Boiling point: 87°–92° C./10 mbar

The product is a mixture of the possible stereo-isomers in a ratio of 3:1 ($^1$H-NMR).

4 g of starting material could to be recovered in the after-runnings.

EXAMPLE P

2-Methyl-4-oxa-2,8-diazabicyclo[4.3.0 ]nonane a) Ethyl 4-hydroxymethyl-3-methylaminopyrrolidine-1-carboxylate 10 g (50 mmol) of ethyl 2-methyl-3-oxa-2,7-diazabicyclo [3.3.0]octane-7-carboxylate (Example H d)) are hydrogenated in 200 ml of ethanol on 3 g of Pd-on-active charcoal (10% of Pd) at 50° C. under 50 bar. The catalyst is filtered off, the filtrate is concentrated and the residue is distilled.

Yield: 8.1 g (80% of theory)
Boiling point: 135°–140° C./0.1 mbar b) Ethyl 2-methyl-4-oxa-2,8-diazabicyclo[4.3.0 ]nonane-8-carboxylate 10.1 g (50 mmol) of ethyl 4-hydroxymethyl-3-methylamino pyrrolidine-1-carboxylate and 8 g (0.1 mol ) of 37% strength formaldehyde solution are dissolved in 100 ml of butanol and the solution is stirred at room temperature overnight. It is then concentrated and the residue is distilled.

Yield: 9.5 g (88.7% of theory)
Boiling point: 110° C./0.1 mbar c) 2-Methyl-4-oxa-2,8-diazabicyclo[4.3.0 ]nonane 9 g (42 mmol) of ethyl 2-methyl-4-oxa-2,8-diazabicyclo [4.3.0]nonane-8-carboxylate are heated under reflux with 28 g of Ba(OH)$_2$·8H$_2$O in 280 ml of water overnight. The BaCO$_3$ is filtered off with suction, the filtrate is concentrated and the residue is boiled up with dioxane. The dioxane solution is concentrated and the residue is distilled.

Yield: 1.3 g (21.8% of theory)
Boiling point: 115° C./8 mbar d) 4-Hydroxymethyl-3-methylaminopyrrolidine 34 g (0.168 mol) of ethyl 4-hydroxymethyl-3-methyl-aminopyrrolidine-1-carboxylate are heated under reflux with 100 g of Ba(OH)$_2$·8H$_2$O in 400 ml of water overnight. The BaCO$_3$ is filtered off with suction, the filtrate is concentrated and the residue is boiled up ten times with 100 ml of dioxane each time. The dioxane solutions are filtered, the filtrate is concentrated and the residue is distilled.

Yield: 13 g (60.3% of theory)
Boiling point: 85°–88° C./0.08 mbar e) 2-Methyl-4-oxa-2,8-diazabicyclo-4.3.0]nonane 8.1.g (0.1 mol) of 37% strength formaldehyde solution in 20 ml of n-butanol are added dropwise to 13 g (0.101 mol) of 4-hydroxymethyl-3-methylaminopyrrolidine in 100 ml of n-butanol at room temperature. The mixture is stirred at room temperature overnight and concentrated and the residue is distilled.

Yield: 8.7 g (61.2% of theory)
Boiling point: 84° C./6 mbar

EXAMPLE Q

3-Oxa-2,7-diazabicyclo[3.3.0]octane a) Ethyl 2-(tetrahydropyran-2-yl)-3-oxa-2,7-diazabicyclo [3.3.0]octane-7-carboxylate 18.1 g (0.106 mol) of ethyl N-allyl-N-(2-oxoethyl)-carbamate (Example M c)) are heated under reflux in 220 ml of toluene, and 14.2 g (0.12 mol) of 5-hydroxypentanal oxime (Acta Chim. Acad. Sci. Hung., 14, 333 (1958)), dissolved in 55 ml of hot toluene, are added dropwise. The mixture is heated under reflux overnight and concentrated and the residue is distilled.

Yield: 15.5 g (54% of theory)
Boiling point: 160° C./0.01 mbar b) Ethyl 3-oxa-2,7-diazabicyclo[3.3.0 ]octane-7-carboxylate 15 g (55.5 mmol) of ethyl 2-(tetrahydropyran-2-yl)-3-oxa-2,7-diazabicyclo[3.3.0]octane-7-carboxylate are heated under reflux with 8.25 g (56 mmol) of 70% strength perchloric acid in 100 ml of ethanol for 30 minutes. 10.5 g (58 mmol) of 30 strength sodium methylate solution are added, the mixture is concentrated, the residue is taken up in water and the solution is saturated with K$_2$CO$_3$ and extracted with CHCl$_3$. The extract is dried over K$_2$CO$_3$ and concentrated and the residue is distilled.

Yield: 7.6 g (73.5% of theory)
Boiling point: 125°–130° C./0.1 mbar c) Ethyl 3-oxa-2,7-diazabicyclo-[3.3.0]octane-7-carboxylate 8.5 g (50 mmol) of ethyl N-(2-oxoethyl)-N-allylcarbamate are heated under reflux with 5.5 g (50 mol) of o-trimethylsilylhydroxylamine in 100 ml of xylene overnight. The mixture is concentrated and the residue is distilled.

Yield: 6.8 g (73% of theory)
Boiling point: 120°–122° C./0.05 mbar d) 3-Oxa-2,7-diazabicyclo[3.3.0]octane This substance is obtained analogously to Example N d) by hydrolysis of ethyl 3-oxa-2,7-diazabicyclo[3.3.0]octane-7-carboxylate with Ba(OH)$_2$·8H$_2$O.

Boiling point: 75° C./10 mbar.

EXAMPLE R

3-Methyl-2,7-diazabicyclo[3.3.0]octane

3-Methyl-2,7-diazabicyclo[3.3.0]octane is obtained analogously to Example I.

Boiling point: 68°–70° C./6 mbar.

EXAMPLE S 2,3-Dimethyl-2,7-diazabicyclo[3.3.0]octane 2,3-Dimethyl-2,7-diazabicyclo[3.3.0]octane is obtained analogously to Example I.

Boiling point: 72°–74° C./10 mbar.

EXAMPLE T 1,2-Dimethyl-3-oxa-2,7-diazabicyclo[3.3.0]octane a) N-Allyl-N-(2,2-dimethoxypropyl)-acetamide 119 g (74 mol) of 2,2-dimethoxypropylacetamide are added dropwise to 29.6 g (0.987 mol) of sodium hydride (80% strength in paraffin oil) in 750 ml of absolute toluene at 80° C. The mixture is then stirred for one hour and 100 g (0.83 mol) of allyl bromide are subsequently added dropwise at 80° C. The mixture is stirred overnight at 80° C. and cooled and the salts are dissolved with water. The aqueous phase is separated off and extracted twice with 100 ml of toluene each time. The toluene solutions are dried over K$_2$CO$_3$ and concentrated and the residue is distilled.

Yield: 112 g (75.6% of theory)
Boiling point: 70° C./0.08 mbar.

b) N-Allyl-N-(2-oxopropyl)-acetamide 85.5 g (0.425 mol) of N-allyl-N-(2,2-dimethoxypropyl)-acetamide are heated under reflux with 212 ml of formic acid for one hour. The mixture is poured onto 500 g of ice and extracted several times with methylene chloride, the organic phases are washed with sodium bicarbonate solution, dried over magnesium sulphate and concentrated and the residue is distilled.

Yield: 50 g (75.8% of theory)
Boiling point: 79° C./0.25 mbar.

c) 7-Acetyl-1,2-dimethyl-3-oxa-2,7-diazabicyclo[3.3.0]octane 15.5 g (0.1 mol ) of N-allyl-N-(2-oxopropyl)-acetamide are dissolved in 100 ml of dioxane, and 9 g of anhydrous sodium acetate and 9 g (0.108 mol) of N-methylhydroxylamine hydrochloride in 10 ml of water are added. The mixture is heated under reflux overnight and cooled and the salts are filtered off with suction and washed with dioxane. The filtrate is concentrated, the residue is taken up in 100 ml of water and K$_2$CO$_3$ is added. The mixture is extracted with CHCl$_3$, the extract is dried over K$_2$CO$_3$ and concentrated and the residue is distilled.

Yield: 15.9 g (86.3% of theory)
Boiling point: 75° C./0.1 mbar.

d) 1,2-Dimethyl-3-oxa-2,7-diazabicyclo[3.3.0]octane 11.8 g (64 mmol) of 7-acetyl-1,2-dimethyl-3-oxa-2,7-diazabicyclo[3.3.0]octane are heated under reflux with 12 g of NaOH in 36 ml of water overnight. The mixture is saturated with K$_2$CO$_3$ and extracted several times with CHCl$_3$, the extract is dried over K$_2$CO$_3$ and concentrated and the residue is distilled.

Yield: 4.7 g (51.6% of theory)
Boiling point: 40° C./0.2 mbar.

EXAMPLE U 2,4-Dimethyl-3-oxa-2,7-diazabicyclo[3.3.0]octane a) Ethyl N-(but-2-enyl)-N-(2,2-dimethoxyethyl)-carbamate 89 g (0.5 mol) of ethyl N-(2,2-dimethoxyethyl)carbamate are added dropwise to 17.5 g (0.58 mol) of NaH (80% strength in paraffin oil) in 500 ml of absolute toluene at 80° C. The mixture is then stirred for one hour and 80 g (0.59 mol) of 1-bromo-2-butene are subsequently added dropwise at 80° C. The mixture is stirred at 80° C. overnight and cooled, the salts are dissolved with water and the aqueous phase is separated off and extracted with toluene. The toluene solutions are dried over $K_2CO_3$ and concentrated and the residue is distilled.

Yield: 90 g (77.8% of theory)
Boiling point: 65° C./0.1 mbar.

b) Ethyl N-(but-2-enyl)-N-(2-oxoethyl)-carbamate 90 g (0.39 mol) of ethyl N-(but-2-enyl)-N-(2,2-dimethoxyethyl)-carbamate are heated under reflux with 200 ml of formic acid for one hour. The mixture is poured onto 500 g of ice and extracted with methylene chloride, the organic phases are washed with sodium bicarbonate solution, dried over magnesium sulphate and concentrated and the residue is distilled.

Yield: 33.6 g (46.5% of theory)
Boiling point: 65° C./0.1 mbar.

c) Ethyl 2,4-dimethyl-3-oxa-2,7-diazabicyclo[3.3.0]-octane-7-carboxylate 18.4 g (0.1 mol) of ethyl N-(but-2-enyl)-N-(2-oxo-ethyl)-carbamate are dissolved in 100 ml of dioxane, and 9 g of anhydrous sodium acetate and 9 g (0.108 mol) of N-methylhydroxylamine hydrochloride in 10 ml of water are added. The mixture is heated under reflux overnight and cooled and the salts are filtered off with suction and washed with dioxane. The filtrate is concentrated, the residue is taken up in 100 ml of water and $K_2CO_3$ is added. The mixture is extracted with $CHCl_3$, the extract is dried over $K_2CO_3$ and concentrated and the residue is distilled.

Yield: 15.0 g (70% of theory)
Boiling point: 74°–87° C./0.1 mbar.

d) 2,4-Dimetheyl-3-oxa-2,7-diazabicyclo[3.3.0]octane 13.2 g (61.6 mmol) of ethyl 2,4-dimethyl-3-oxa-2,7-diazabicyclo[3.3.0]octane-7-carboxylate are heated under reflux with 39 g of $Ba(OH)_2 \cdot 8H_2O$ in 200 ml of water overnight. $K_2CO_3$ is added, the $BaCO_3$ is filtered off with suction and the filtrate is extracted several times with $CHCl_3$. The extract is dried over $K_2CO_3$ and concentrated and the residue is distilled.

Yield: 4.8 g (54.8% of theory)
Boiling point: 74° C./8 mbar.

EXAMPLE V

Ethyl 2,7-diazabicyclo[3.3.0]octane-2-carboxylate

7-Benzyl-2,7-diazabicyclo[3.3.0]octane (Example Jc) is reacted with ethyl chloroformate analogously to Example Oa) to give ethyl 7-benzyl-2,7-diazabicyclo[3.3.0]octane-2-carboxylate, and this is then debenzylated hydrogenolyrically analogously to Example Jd). A colorless oil of boiling point 90° C./0.1 mbar is obtained.

EXAMPLE W

2-Phenyl-2,7-diazabicyclo[3.3.0]octane

The preparation is carried out analogously to Example I);
Boiling point: 103° C./0.08 mbar.

EXAMPLE X

4-Oxa-2,8-diazabicyclo[4.3.0]nonane
a) Ethyl 3-amino-4-hydroxymethyl-pyrrolidine-1-carboxylate Ethyl 3-oxa-2,7-diazabicyclo[3.3.0]octane-7-carboxylate (Example Qc) is hydrogenated analogously to Example Pa).
Boiling point: 163°–168° C./0.8 mbar b) 3-Amino-4-hydroxymethyl-pyrrolidine Ethyl 3-amino-4-hydroxymethyl-pyrrolidine-1-carboxylate is hydrolyzed analogously to Example Pd).
Boiling point: 78° C./0.06 mbar.

c) 4-Oxa-2,8-diazabicyclo[4.3.0]nonane

3-Amino-4-hydroxymethyl-pyrrolidine is reacted with formaldehyde solution analogously to Example Pe).
Boiling point: 50°–60° C./0.07 mbar

EXAMPLE Y trans-3-Ethylamino-4-methylthio-pyrrolidine
a) 1-Benzoyl-trans-3-ethylamino-4-methylthiopyrrolidine 8.65 g (50 mmol) of 1-benzoyl-2,5-dihydropyrrole [Chem. Ber. 22, 2521 (1889)] are initially introduced into 30 ml of methylene chloride, and 4.94 g (60 mmol) of methanesulphonyl chloride in 20 ml of methylene chloride are added dropwise at 0° C. The mixture is subsequently stirred at 20°–25° C. for 16 hours and concentrated under 8 mbar and the residue is dissolved in 50 ml of tetrahydrofuran. 18 g (0.2 mol) of 50% strength aqueous ethylamine solution are then added. The batch is boiled for 18 hours, while cooling under reflux, poured into water and extracted with methylene chloride. On concentrating, 11.1 g of crude product are obtained, and the crude product is chromatographed with ethyl acetate/ethanol 5:1 on silica gel (RF value 0.34).

Yield: 7.4 g (56% of theory).

b) trans-3-Ethylamino-4-methylthio-pyrrolidine 6.0 g (22 mmol) of 1-benzoyl-trans-3-ethylamino-4-methylthio-pyrrolidine are stirred vigorously with 22 ml of 5N NaOH at 100° C. for 24 hours, until the conversion is homogeneous. The mixture is then extracted with 3×80 ml of ether and the extract is dried over sodium sulphate and concentrated on a rotary evaporator. The crude product is distilled through a micro-puncture column.

Yield: 1.56 g (44% of theory) of colorless liquid,
Boiling point: 52° C./0.1 mbar

EXAMPLE Z trans-3-amino-4-methylthior-pyrrolidine

1-Benzoyl-2,5-dihydropyrrole is reacted with methylsulfenyl chloride analogously to Example Y to give 1-benzoyl-3-chloro-4-methylthiopyrrolidine which is reacted as a crude product with ammonia to give 3-amino-1-benzoyl-4-methyl-thio-pyrrolidine and the benzoyl radical is removed with sodium hydroxide solution.

Yield over 3 stages: 47% of theory
Boiling point: 108°–110° C./11 mbar.

EXAMPLE ZA

4-Methyl-2,8-diazabicyclo[4.3.0]nonane
a) 5-Methyl-1,4-dihydropyridine-2,3-dicarboxylic acid N-benzylimide 33 g (0.29 mol) of 2-methyl-2-propenal-dimethylhydrazone and 55 g (0.29 mol) of N-benzylmaleinimide are stirred in 225 ml of acetonitrile for 3 hours at 60° C. Then the solvent is removed in a rotary evaporator, the residue is taken up in 600 ml of toluene and, after adding 150 g of silica gel, the mixture is boiled for 1 hour under reflux. Then the mixture is filtered while hot and the silica gel is boiled out several times with ethanol. The combined organic phases are concentrated in a rotary evaporator. 17.5 g (24 % of theory) of red crystals of a melting point of 184°–186° C. are obtained.

b) 5-Methyl-hexahydropyridine-2,3-dicarboxylic acid N-benzylimide 17.5 g (70 mmol) of 5-methyl-1,4-dihydropyridine-2,3-dicarboxylic acid N-benzylimide are hydrogenated in 150 ml of tetrahydrofuran at 70° C. and under 100 bar over palladium on active charcoal. Then the catalyst is filtered off and the filtrate is concentrated by evaporation. The solid oily residue (13.0 g) is used as a crude product in the next stage.

c) 8-Benzyl-4-methyl-2,8-diazabicyclo[4.3.0]nonane 13.0 g of crude 5-methyl-hexahydropyridine-2,3-dicarboxylic acid N-benzylimide are added in the form of a solution in 50 ml of absolute tetrahydrofuran to 4.6 g (0.12 mol) of lithium aluminum hydride in 100 ml of absolute tetrahydrofuran, already present in the vessel. Then the mixture is boiled for 17 hours under reflux. 4.6 g of water in 14 ml of tetrahydrofuran, 4.6 g of 10% strength sodium hydroxide solution and 13.8 g of water are added dropwise one after the other. The salts are filtered off, the filtrate is concentrated by evaporation and the residue is distilled.

Yield: 8.7 g (54%, based on 5-methyl-1,4-dihydropyridine-2,3-dicarboxylic acid N-benzylimide);

boiling point: 95°–98° C./0.1 mbar.

d) 4-Methyl-2,8-diazabicyclo[4.3.0]nonane 8.0 g (35 mmol) of 8-benzyl-4-methyl-2,8-diazabicyclo[4.3.0]nonane are dissolved in 60 ml of methanol and hydrogenated over palladium on active charcoal at 100° C. and under 100 bar. Then the catalyst is filtered off, the filtrate is concentrated by evaporation and the residue is distilled.

Yield: 3.3 g (67% of theory)

boiling point: 88°–89° C./11 mbar.

The $^1$H-NMR spectrum shows the compound to be a mixture of two stereoisomers in a ratio of 7:2.

EXAMPLE AA 5,6,7,8-Tetrafluoro-1-(2,4-difluorophenyl)-1,4-dihydro-4-oxo-3-quinolinecarboxylic acid a) Ethyl 2-(2,3,4,5,6-pentafluorobenzoyl)-3-(2,4-difluorophenylamino)-acrylate 44.3 g of 2,4-difluoroaniline are added dropwise to a solution of 115 g of ethyl 3-ethoxy-2-(2,3,4,5,6-pentafluorobenzoyl)-acrylate in 380 ml of ethanol, while cooling with ice and stirring. The mixture is stirred at room temperature for 1 hour, 380 ml of water are added, while cooling with ice, and the precipitate is filtered off with suction, washed with ethanol/H$_2$O (1:1) and dried. 135.4 g of the title compound of melting point 97°–99° C. are obtained.

b) Ethyl 5,6,7,8-tetrafluoro-1-(2,4-difluorophenyl)-1,4-dihydro-4-oxo-3-quinolinecarboxylate A mixture of 135.4 g of ethyl 2-(2,3,4,5,6-pentafluorobenzoyl)-3-(2,4-difluorophenylamino)acrylate, 20.6 g of sodium fluoride and 300 ml of anhydrous dimethylformamide is heated at 140°–150° C. for 3 hours. The suspension is poured hot onto 2 kg of ice and the precipitate is filtered off with suction, washed with water and dried. 122 g of the title compound of melting point 160°–162° C. are obtained.

c) 5,6,7,8-Tetrafluoro-1-(2,4-difluorophenyl)-1,4-dihydro-4-oxo-3-quinolinecarboxylic acid 40.1 g of ethyl 5,6,7,8-tetrafluoro-1-(2,4-difluorophenyl)-1,4-dihydro-4-oxo-3-quinolinecarboxylate are added to a mixture of 28.5 ml of concentrated sulphuric acid, 250 ml of glacial acetic acid and 200 ml of water and the mixture is heated under reflux for 2 hours. The hot solution is poured onto ice and the precipitate is filtered off with suction, washed with water and dried. 34.5 g of the title compound of melting point 250°–252° C. are obtained.

EXAMPLE AB 5,7-Dichloro-1-cyclopropyl-6-fluoro-1,4-dihydro-4-oxo-3-quinolinecarboxylic acid a) Ethyl (2,4-dichloro-3,6-difluorobenzoyl)-acetate 2.1 g of magnesium filings are suspended in 5 ml of anhydrous ethanol. 0.5 ml of carbon tetrachloride is added and, when the reaction has started, a mixture of 14 g of ethyl malonate, 10 ml of absolute ethanol and 41 ml of toluene is added dropwise. The mixture is then heated at 70° C. for a further 1.5 hours and cooled to –5° C. to –10° C. with acetone/dry ice, and a solution of 21.5 g of 2,4-dichloro-3,6-difluorobenzoyl chloride in 30 ml of toluene is slowly added dropwise at this temperature. The mixture is stirred at 0° C. for 1 hour and allowed to come to room temperature overnight, and a mixture of 35 ml of ice-water and 5 ml of concentrated sulphuric acid is allowed to run in, while cooling with ice. The phases are separated and subsequent extraction is carried out twice with toluene. The combined toluene solutions are washed once with saturated sodium chloride solution and dried with Na$_2$SO$_4$ and the solvent is stripped off in vacuo. 34.7 g of diethyl (2,4-dichloro-3,6-difluorobenzoyl)-malonate are obtained as a crude product.

0.04 g of p-toluenetoluenesulphonic acid is added to an emulsion of 34.7 g of crude diethyl (2,4-di-chloro-3,6-difluorobenzoyl)-malonate in 40 ml of water. The mixture is heated at the boiling point for 3 hours, while stirring thoroughly, the cooled emulsion is extracted several times with methylene chloride, the combined CH$_2$Cl$_2$ solutions are washed once with saturated sodium chloride solution and dried with Na$_2$SO$_4$ and the solvent is distilled off in vacuo. Fractionation of the residue (33.9 g) in vacuo gives 13.9 g of ethyl (2,4-dichloro-3,6-difluorobenzoyl)-acetate of boiling point 110°–115° C./0.05 mbar, n$_D^{25}$: 1,5241.

b) Ethyl 2-(2,4-dichloro-3,6-difluorobenzoyl)-3-ethoxyacrylate 13.7 g of ethyl (2,4-dichloro-3,6-difluorobenzoyl)acetate are heated under reflux with 10.25 g of triethyl orthoformate and 11.8 g of acetic anhydride for 2 hours. The mixture is then concentrated in vacuo up to a bath temperature of 140° C. and 15.7 g of ethyl 2-(2,4-dichloro-3,6-difluorobenzoyl)-3-ethoxy-acrylate are obtained as an oil, n$_D^{25}$: 1.5302.

c) Ethyl 2-(2,4-dichloro-3,6-difluorobenzoyl)-3-cyclopropylamino-acrylate 15.6 g of ethyl 2-(2,4-dichloro-3,6-difluorobenzoyl)-3-ethoxy-acrylate are dissolved in 50 ml of ethanol, and 2.75 g of cyclopropylamine are added dropwise, while cooling. The mixture is stirred at room temperature for 1 hour, 50 ml of water are added, while cooling with ice, and the precipitate is filtered off with suction, rinsed with ethanol/H$_2$O (1:1) and dried. 14.1 g of ethyl 2-(2,4-dichloro-3,6-difluorobenzoyl)-3-cyclopropylamino-acrylate of melting point 106°–107° C. are obtained.

d) Ethyl 5,7-dichloro-1-cyclopropyl-6-fluoro-1,4-dihydro-4-oxo-3-quinolinecarboxylate 6 g of ethyl 2-(2,4-dichloro-3,6-difluorobenzoyl)-3-cyclopropylamino-acrylate are heated in 100 ml of dimethylformamide at 150° C. with 2.75 g of potassium carbonate for 2.5 hours. The mixture is poured into 600 ml of ice-water and the precipitate is filtered off with suction, washed with water and dried. 5.2 g of ethyl 5,7-dichloro-1-cyclopropyl-6-fluoro-1,4-dihydro-4-oxo-3-quinolinecarboxylate of melting point 227°–229° C. are obtained.

e) 5,7-Dichloro-1-cyclopropyl-6-fluoro-1,4-dihydro-4-oxo-3-quinoinecarboxylic acid 5.2 g of ethyl 5,7-dichloro-1-cyclopropyl-6-fluoro-1,4-dihydro-4-oxo-3-quinolinecarboxylate are heated under reflux in a mixture of 38 ml of acetic acid, 30 ml of water and 4.3 ml of concentrated sulphuric acid for 2.5 hours. After cooling, the mixture is poured into 250 ml of ice-water and the precipitate is filtered off with suction, washed with water and dried. 4.8 g of 5,7-dichloro-1-cyclopropyl-6-fluoro-1,4-dihydro-4-oxo-3-quinolinecarboxylic acid of melting point 277°–278° C. are obtained.

EXAMPLE AC 5,7-Dichloro-6-fluoro-1-(2,4-difluorophenyl)-1,4-dihydro-4-oxo-3-quinolinecarboxylic acid a) Ethyl 2-(2,4-dichloro-3,6-difluorobenzoyl)-3-(2,4-difluoropheny)-acrylate 35.3 g of ethyl 2-(2,4-dichloro-3,6-difluorobenzoyl)-3-ethoxyacrylate are dissolved in 120 ml of ethanol, and 12.9 g of 2,4-difluoroaniline are added dropwise, while cooling with ice. The mixture is stirred at room temperature for 1.5 hours, 120 ml of water are added, while cooling, and the precipitate is filtered off with suction, rinsed with ethanol/H$_2$O (1:1) and dried. 40.5 g of ethyl 2-(2,4-dichloro-3,6-difluorobenzoyl)-3-(2,4-difluorophenylamino)acrylate are obtained, melting point: 84°–86° C.

b) Ethyl 5,7-dichloro-6-fluoro-1-(2,4-difluorophenyl)-1,4-dihydro-4-oxo-3-quinolinecarboxylate 43.6 g of ethyl 2-(2,4-dichloro-3,6-difluorobenzoyl)-3-(2,4-difluorophenylamino)-acrylate are heated in 260 ml of dimethylformamide at 150° C. with 15.2 g of potassium carbonate for 2.5 hours. The mixture is poured into 1 liter of ice-water and the precipitate is filtered off with suction, washed with water and dried. 38.6 g of ethyl 5,7-dichloro-6-fluoro-1-(2,4-difluorophenyl)-1,4-dihydro-4-oxo-3-quinolinecarboxylate are obtained.

c) 5,7-Dichloro-6-fluoro-1-(2,4-difluorophenyl)-1,4-dihydro-4-oxo-3-quinolinecarboxylic acid 41.6 g of ethyl 5,7-dichloro-6-fluoro-1-(2,4-difluorophenyl)-1,4-dihydro-4-oxo-3-quinolinecarboxylate are heated under reflux with 250 ml of acetic acid, 200 ml .of water and 28.5 ml of concentrated sulphuric acid for 3 hours. After cooling, the mixture is poured into 2 liter of ice-water and the precipitate is filtered off with suction, washed with water and dried. 35.5 g of 5,7-dichloro-6-fluoro-1-(2,4-difluorophenyl)-1,4-dihydro-4-oxo-3-quinolinecarboxylic acid are obtained, melting point: 244°–246° C.

EXAMPLE 1

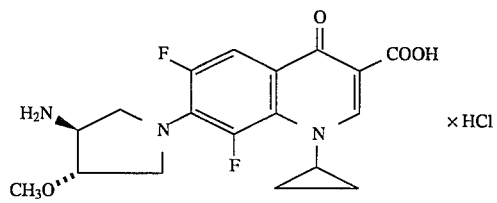

A. 855 mg (3 mmol) of 1-cyclopropyl-6,7,8-trifluoro-1,4-dihydro-4-oxo-3-quinolinecarboxylic acid are heated under reflux in a mixture of 9 ml of acetonitrile and 4.5 ml of dimethylformamide in the presence of 330 mg (3.3 mmol) of 1,4-diazabicyclo[2.2.2]octane and 750 mg of trans-3-tert.-butoxycarbonyl-amino-4-methoxy-pyrrolidine for 1 hour. The mixture is evaporated, the residue is stirred with water and the mixture is dried.

Yield: 1.3 g (90.5% of theory) of 7-(trans-3-tert.-butoxycarbonylamino-4-methoxy-1-pyrrolidinyl)-1-cyclo-propyl-6,8-difluoro-1,4-dihydro-4-oxo-3-quinolinecarboxylic acid.

Melting point: 222°–224° C. (with decomposition) (from glycol monomethyl ether).

B. 1.2 g (3.5 mmol) of the product from stage A are introduced into 10 ml of 3N hydrochloric acid, the mixture is stirred until a solution is obtained and the solution is concentrated. The residue is triturated with ethanol, filtered off with suction and dried at 60° under a high vacuum.

Yield: 0.73 g (70% of theory) of 7-(trans-3-amino-4-methoxy-1-pyrrolidinyl)-1-cyclopropyl-6,8-difluoro-4-oxo-3-quinolinecarboxylic acid hydrochloride.

Melting points 279° C. (with decomposition).

EXAMPLE 2

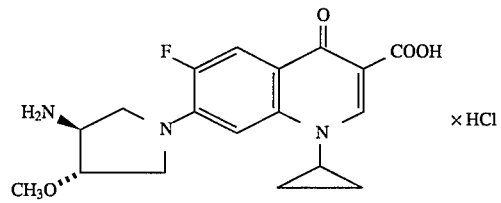

1-Cyclopropyl-6,7-difluoro-1,4-dihydro-4-oxo-3-quinolinecarboxylic acid is reacted analogously to Example 1 to give:

A. 7-(trans-3-tert.-Butoxycarbonylamino-4-methoxy-1-pyrrolidinyl)-1-cyclopropyl-6-fluoro-1,4-dihydro-4-oxo-3-quinolinecarboxylic acid, melting points 247°–249° C. (with decomposition).

B. 7-(trans-3-Amino-4-methoxy-1-pyrrolidinyl)-1-cyclopropyl-6-fluoro-4-oxo-3-quinolinecarboxylic acid hydrochloride, melting points from 293° C. (with decomposition).

EXAMPLE 3

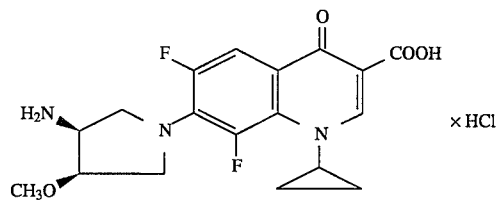

A reaction is carried out analogously to Example 1 with cis-3-tert.-butoxycarbonylamino-4-methoxy-pyrrolidine to give:

A. 7-(cis-3-tert.-Butoxycarbonylamino-4-methoxy-1-pyrrolidinyl)-1-cyclopropyl-6,8-difluoro-1,4-dihydro-4-oxo-3-quinolinecarboxylic acid, melting points 230°–231° C. (with decomposition).

B. 7-(cis-3-Amino-4-methoxy-1-pyrrolidinyl)-1-cyclo-propyl-6,8-difluoro-4-oxo-3-quinolinecarboxylic acid hydrochloride, melting point 201°–203° C. (with decomposition)

EXAMPLE 4

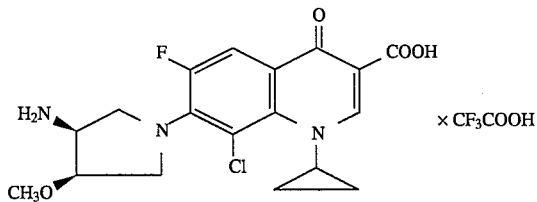

× CF₃COOH

A. 1.5 g (5 mmol) of 8-chloro-1-cyclopropyl-6,7-difluoro-1,4-dihydro-4-oxo-3-quinolinecarboxylic acid are heated under reflux in a mixture of 10 ml of acetonitrile and 5 ml of dimethylformamide with 550 mg (5 mmol) of 1,4-diazabicyclo[2.2.2]octane and 1.2 g (5.6 mmol) of cis-3-tert.-butoxycarbonylamino-4-methoxy-pyrrolidine for 2 hours. The mixture is allowed to cool and the precipitate which has separated out is filtered off with suction, rinsed thoroughly with water and dried at 100° C. in vacuo.

Yield: 2.0 g (80.7%) of 7-(cis-3-tert.-butoxycarbonylamino-4-methoxy-1-pyrrolidinyl)-8-chloro-1-cyclopropyl-6-fluoro-1,4-dihydro-4-oxo-3-quinolinecarboxylic acid, melting points 222°–225° C. (with decomposition).

B. 1.9 g (3.8 mmol) of the product from stage A are stirred in 10 ml of trifluoroacetic acid at room temperature for 20 minutes, the solution is concentrated, the oil which remains is evaporated twice with methylene chloride and the residue is stirred with ether. The precipitate which has separated out is filtered off with suction, washed with ether and dried at 60° C. in vacuo.

Yield: 1.9 g (97% of theory) of 7-(cis-3-amino-4-methoxy-1-pyrrolidinyl)-8-chloro-1-cyclopropyl-6-fluoro-1,4-dihydro-4-oxo-3-quinolinecarboxylic acid trifluoroacetate, melting point: 235°–239° C. (with decomposition).

EXAMPLE 5

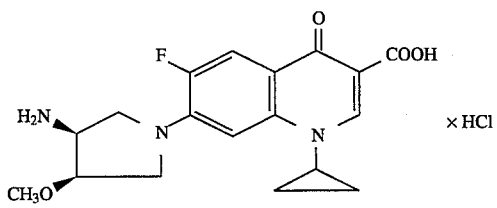

× HCl cis-3-tert.-Butoxycarbonylamino-4-methoxy-pyrrolidine is reacted with 1-cyclopropyl-6,7-difluoro-1,4-dihydro-4-oxo-3-quinolinecarboxylic acid analogously to Example 1 to give:
A. 7-(cis-3-tert.-Butoxycarbonylamino-4-methoxy-1-pyrrolidinyl)-1-cyclopropyl-6-fluoro-1,4-dihydro-4-oxo-3-quinolinecarboxylic acid, melting point 232°–233° C. (with decomposition).
B. 7-(cis-3-Amino-4-methoxy-1-pyrrolidinyl)-1-cyclo-propyl-6-fluoro-1,4-dihydro-4-oxo-3-quinolinecarboxylic acid hydrochloride, melting point 252°–256° C. (with decomposition) (sintering beforehand).

EXAMPLE 6

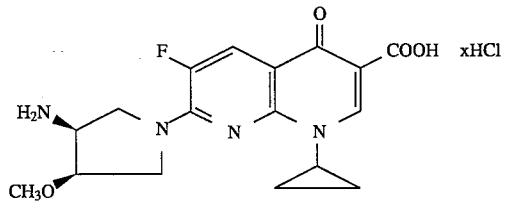

xHCl cis-3-tert.-Butoxycarbonylamino-4-methoxypyrrolidine is reacted with 7-chloro-1-cyclopropyl-6-fluoro-1,4-dihydro-4-oxo-1,8-naphthyridine-3-carboxylic acid analogously to Example 1 to give:
A. 7-(cis-tert.-Butoxycarbonylamino-4-methoxy-1-pyrrolidinyl)-1-cyclopropyl-6-fluoro-1,4-dihydro-4-oxo-1,8-naphthyridine-3-carboxylic acid, melting point 214°–216° C. (with decomposition).
B. 7-(cis-3-Amino-4-methoxy-1-pyrrolidinyl)-1-cyclopropyl-6-fluoro-1,4-dihydro-4-oxo-1,8-naphthyridine-3-carboxylic acid hydrochloride, melting point 205°–210° (with decomposition).
Mass spectrum, m/e 362 (M⁺), 330 (M⁺–32), 318 (M⁺—CO₂), 286, 260, 41 (C₃H₅), 36 (HCl).

EXAMPLE 7

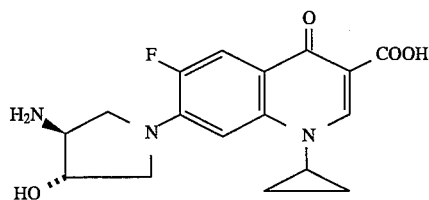

1.1 g (10 mmol) of 1,4-diazabicyclo[2.2.2]octane and 0.55 g (5.4 mmol) of trans-3-amino-4-hydroxy-pyrrolidine are added to 1.33 g (5 mmol) of 1-cyclopropyl-6,7-difluoro-1,4-dihydro-4-oxo-3-quinolinecarboxylic acid in a mixture of 30 ml of acetonitrile and 5 ml of dimethylformamide and the mixture is heated under reflux for 1 hour. The suspension is concentrated, water is added to the residue and the undissolved product is filtered off with suction and recrystallized from dimethylformamide.

Yield: 1.2 g (73% of theory) of 7-(trans-3-amino-4-hydroxy-1-pyrrolidinyl)-1-cyclopropyl-6-fluoro-1,4-dihydro-4-oxo-3-quinolinecarboxylic acid, Melting points 274°–278° C. (with decomposition).

EXAMPLE 8

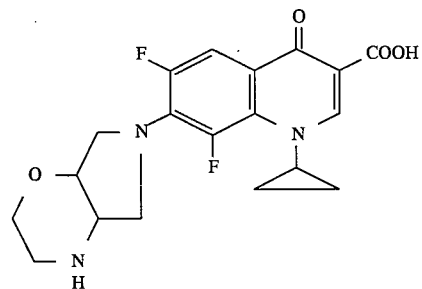

850 mg (3 mmol) of 1-cyclopropyl-6,7,8-trifluoro-1,4-dihydro-4-oxo-3-quinolinecarboxylic acid are heated under reflux in 9 ml of pyridine with 630 mg (3.1 mmol) of 2-oxa-5,8-diazabicyclo[4.3.0]nonane dihydrochloride and 500 mg (4.5 mmol) of 1,4-diazabicyclo[2.2.2]octane for 1 hour. The mixture is concentrated, the residue is stirred with water and the precipitate is filtered off with suction, washed with water, dried and recrystallized from glycol monomethyl ether.

Yield: 840 mg (72% of theory) of 1-cyclopropyl-6,8-difluoro-1,4-dihydro-7-(2-oxa-5,8-diazabicyclo[4.3.0]non-8-yl)-4-oxo-3-quinolinecarboxylic acid, Melting point: 289°–291° C. (with decomposition);

Mass spectrum: m/e 391 ($M^+$), 347 ($M^+$—$CO_2$), 331, 306, 294, 262, 234, 98, 41 ($C_3H_5$).

EXAMPLE 9

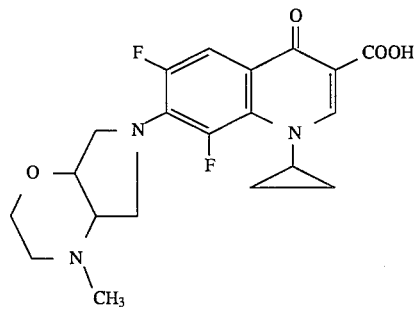

The reaction is carried out analogously to Example 8 with 5-methyl-2-oxa-5,8-diazabicyclo[4.3.0]nonane dihydrochloride to give: 1-cyclopropyl-6,8-difluoro-1,4-dihydro-7-(5-methyl-2-oxa-5,8-diazabicyclo[4.3.0]non-8-yl)-4-oxo-3-quinolinecarboxylic acid, melting point: from 270° C. (with decomposition);

Mass spectrum: m/e 405 ($M^+$), 361 ($M^+CO_2$), 331, 112, (100%).

EXAMPLE 10

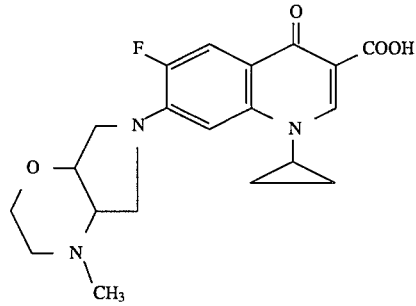

795 mg (3 mmol) of 1-cyclopropyl-6,7-difluoro-1,4-dihydro-4-oxo-3-quinolinecarboxylic acid are heated under reflux in a mixture of 9 ml of acetonitrile and 4.5 ml of dimethylformamide with 890 mg (4.1 mmol) of 5-methyl-2-oxa-5,8-diazabicyclo[4.3.0]nonane dihydrochloride and 860 mg (7.8 mmol) of 1,4-diazabicyclo[2.2.2]octane for 2 hours. The mixture is evaporated, the residue is stirred with water and the undissolved product is filtered off with suction, washed with water, dried and recrystallized from dimethylformamide.

Yield: 0.8 g (69% of theory) of 1-cyclopropyl-6-fluoro-1,4-dihydro-7-(5-methyl-2-oxa-5,8-diazabicyclo[4.3.0]non-8-yl)-4-oxo-3-quinolinecarboxylic acid, melting point 340° C. (with decomposition) (on heating up, the substance already becomes dark from about 300°).

Mass spectrum, m/e ($M^+$), 343 ($M^+$—$CO_2$), 313, 244, 112 (100%).

EXAMPLE 11

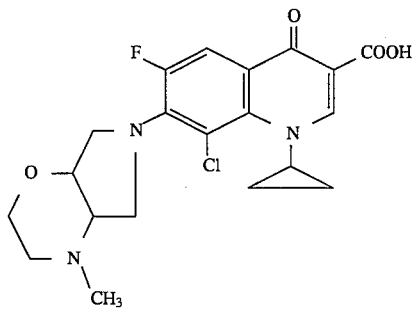

The reaction is carried out analogously to Example 10 with 8-chloro-1-cyclopropyl-6,7-difluoro-1,4-dihydro-4-oxo-3-quinolinecarboxylic acid to give 8-chloro-1-cyclopropyl-6-fluoro-1,4-dihydro-7-(5-methyl-2-oxa-5,8-diazabicyclo[4.3.0]non-8-yl)-4-oxo-3-quinolinecarboxylic acid, melting point 258°–262° C. (with decomposition) (recrystallized from dimethylformamide).

EXAMPLE 12

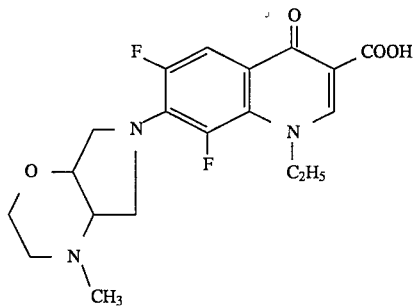

The reaction is carried out analogously to Example 10 with 1-ethyl-6,7,8-trifluoro-1,4-dihydro-4-oxo-3-quinolinecarboxylic acid to give 1-ethyl-6,8-difluoro-1,4-dihydro-7-(5-methyl-2-oxa-5,8-diazabicyclo[4.3.0]non-8-yl)-4-oxo-3-quinolinecarboxylic acid, melting point 279°–281° C. (with decomposition).

EXAMPLE 13

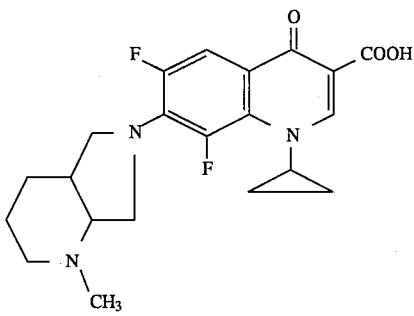

0.84 g (3 mmol) of 1-cyclopropyl-6,7,8-trifluoro-1,4-dihydro-4-oxo-3-quinolinecarboxylic acid are heated under reflux in a mixture of 6 ml of acetonitrile and 3 ml of dimethylformamide with 0.66 g (6 mmol) of 1,4-diazabicyclo[2.2.2]octane and 0.49 g (3.5 mmol) of 2-methyl-2,8-diazabicyclo[4.3.0]nonane for 2 hours. The suspension is concentrated, the residue is stirred with 20 ml of water, the mixture is brought to pH 7 with 2N hydrochloric acid and the precipitate is filtered off with suction, washed with water, dried and recrystallized from glycol monomethyl ether.

Yield: 0.7 g (58% of theory) of 1-cyclopropyl-6,8-difluoro-1,4-dihydro-7-(2-methyl-2,8-diazabicyclo [4.3.0]-non-8-yl)-4-oxo-3-quinolinecarboxylic acid, melting point 204°–207° C.

EXAMPLE 14

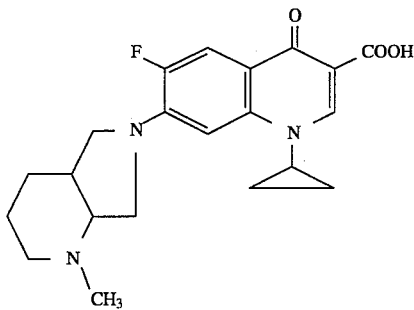

Analogously to Example 13, 1-cyclopropyl-6-fluoro-1,4-dihydro-7-(2-methyl-2,8-diazabicyclo[4.3.0]non-8-yl)-4-oxo-3-quinolinecarboxylic acid, melting point 234°–236°, is obtained with 1-cyclopropyl-6,7-difluoro-1,4-dihydro-4-oxo-3-quinolinecarboxylic acid.

EXAMPLE 15

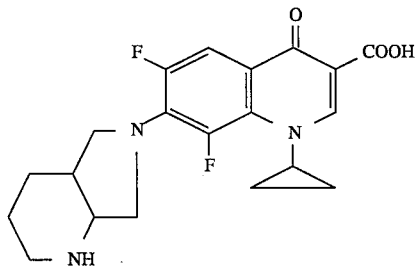

A. 1-Cyclopropyl-6,7,8-trifluoro-1,4-dihydro-4-oxo-3-quinolinecarboxylic acid is reacted with 2,8-diazabicyclo[4.3.0]nonane analogously to Example 13 to give 1-cyclopropyl-7-(2,8-diazabicyclo[4.3.0]non-8-yl)-6,8-difluoro-1,4-dihydro-4-oxo-3-quinolinecarboxylic acid, melting point 265°–267° (with decomposition) (recrystallized from dimethylformamide).

B. If the reaction of Example 15 A) is carried out in a mixture of acetonitrile/1-methyl-2-pyrrolidinone and the crude product is recrystallized from dimethylformamide, 1-cyclopropyl-7-(2,8-diazabicyclo[4.3.0]non-8-yl)-6,8-difluoro-1,4-dihydro-4-oxo-3-quinolinecarboxylic of melting point 269°–271° C. (with decomposition) is obtained. According to a comparison by chromatography and spectroscopy, the product is identical to the product prepared according to process A).

C. 65 g (167 mmol) of the betaine (stage A) are dissolved in 330 ml of half-concentrated hydrochloric acid by heating, the solution is concentrated and the residue is stirred with 300 ml of ethanol. The undissolved precipitate is filtered off with suction, washed with ethanol and dried at 100° C. in vacuo.

Yield: 66.3 g (93% of theory) of 1-cyclopropyl-7-(2,8-diazabicyclo [4.3.0]non-8-yl)-6,8-difluoro-1,4-dihydro-4-oxo-3-quinolinecarboxylic acid hydrochloride, melting point: 303°–305° C. (with decomposition).

EXAMPLE 16

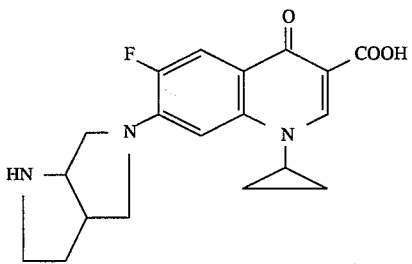

Analogously to Example 13, 1-cyclopropyl-7-(2,7-diazabicyclo[3.3.0]oct-7-yl)-6-fluoro-1,4-dihydro-4-oxo-3-quinolinecarboxylic acid, melting point: 260°–282° (with decomposition), is obtained with 1-cyclopropyl-6,7-difluoro-1,4-dihydro-4-oxo-3-quinolinecarboxylic acid and 2,7-diazabicyclo[3.3.0]octane.

Mass spectrum: m/e 357 ($M^+$), 313 (100%, $M^+$—$CO_2$), 269, 257, 244, 82, 28.

EXAMPLE 17

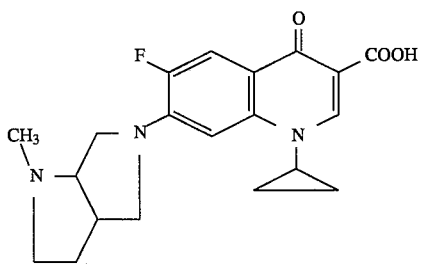

Analogously to Example 13, 1-cyclopropyl-6-fluoro-1,4-dihydro-7-(2-methyl-2,7-diazabicyclo[3.3.0]oct-7-yl)-4-oxo-3-quinolinecarboxylic acid, melting points 206°–208° C. (with decomposition), is obtained with 1-cyclopropyl-6, 7-difluoro-1,4-dihydro-4-oxo-3-quinolinecarboxylic acid and 2-methyl-2,7-diazabicyclo[3.3.0]octane.

EXAMPLE 18

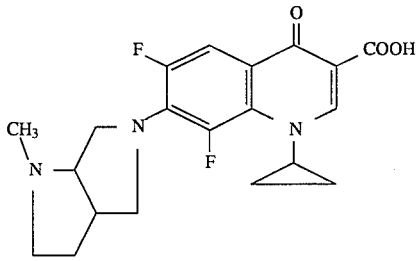

Analogously to Example 13, 1-cyclopropyl-6,8-difluoro-1,4-dihydro-7-(2-methyl-2,7-diazabicyclo [3.3.0]oct-7-yl)-4-oxo-3-quinolinecarboxylic acid, melting point 198°–200° C. (with decomposition), is obtained with 2-methyl-2,7-diazabicyclo [3.3.0 ]octane.

EXAMPLE 19

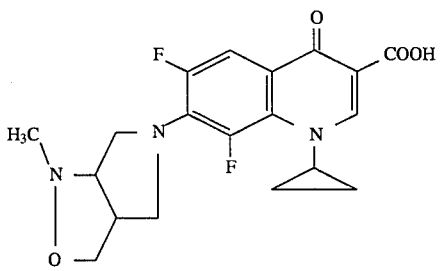

A mixture of 2.83 g (10 mmol) of 1-cyclopropyl-6,7,8-trifluoro-1,4-dihydro-4-oxo-3-quinolinecarboxylic acid, 1.1 g (10 mmol) of 1,4-diazabicyclo[2.2.2]octane and 1.4 g (11 mmol) of 2-methyl-3-oxa-2,7-diazabicyclo[3.3.0]octane in 20 ml of acetonitrile and 10 ml of 1-methyl-2-pyrrolidinone is heated under reflux for 1 hour. It is concentrated in vacuo, the residue is stirred with water (pH 7) and the precipitate is filtered off with suction, washed with water and dried at 60° in vacuo. The crude product (3.7 g) is recrystallized from dimethylformamide.

Yield: 1.9 g (49% of theory) of 1-cyclopropyl-6,8-difluoro-1,4-dihydro-7-(2-methyl-3-oxa-2,7-diazabicyclo [3.3.0]oct-7-yl)-4-oxo-3-quinolinecarboxylic acid, melting point 221°–223° C. (with decomposition).

EXAMPLE 20

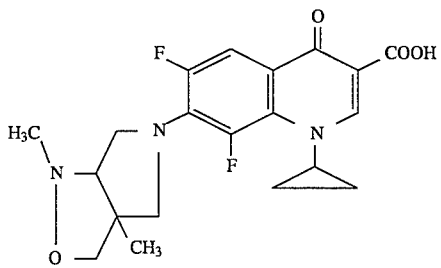

The reaction is carried out analogously to Example 19 with 2,5-dimethyl-3-oxa-2,7-diazabicyclo[3.3.0]octane to give 1-cyclopropyl-6,8-difluoro-1,4-dihydro-7-(2,5-dimethyl-3-oxa-2,7-diazabicyclo[3.3.0]oct-7-yl)-4-oxo-3-quinolinecarboxylic acid of melting point 237°–238° C. (with decomposition).

EXAMPLE 21

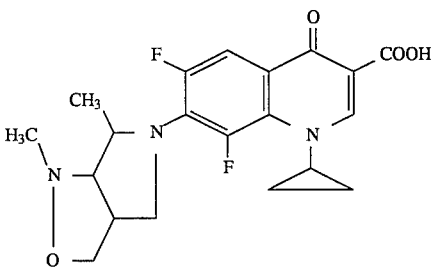

The reaction is carried out analogously to Example 19 with 2,8-dimethyl-3-oxa-2,7-diazabicyclo[3.3.0]octane to give 1-cyclopropyl-6,8-difluoro-1,4-dihydro-7-(2,8-dimethyl-3-oxa-2,7-diazabicyclo-[3.3.0]oct-7-yl)-4-oxo-3-quinolinecarboxylic acid of melting-point 197°–199° C.

EXAMPLE 22

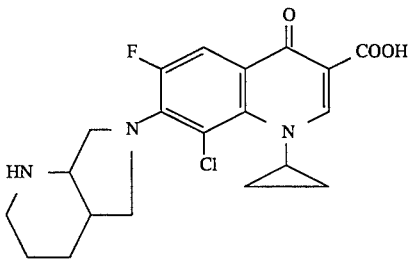

3 g (10 mmol) of 8-chloro-1-cyclopropyl-6,7-difluoro-1,4-dihydro-4-oxo-3-quinolinecarboxylic acid are heated under reflux in a mixture of 30 ml of acetonitrile and 15 ml of 1-methyl-2-pyrrolidinone with 1.4 g (11 mmol) of 2,8-diazabicyclo[4.3.0]nonane and 1.65 g (15 mmol) of 1,4-diazabicyclo[2.2.2]octane for 1 hour. After cooling, the suspension is stirred with about 150 ml of water and the undissolved precipitate is filtered off with suction, washed with water and ethanol and dried at 80° C./12 m bar. The crude product is recrystallized from 40 ml of glycol monomethyl ether.

Yield: 2.3 g (57% of theory) of 8-chloro-1-cyclopropyl-7-(2,8-diazabicyclo[4.3.0]non-8-yl)-6-fluoro-1,4-dihydro-4-oxo-3-quinolinecarboxylic acid, melting points 224°–226° C. (with decomposition).

B. The crude betaine is prepared analogously to Example 22 A and is suspended in 50 ml of water and dissolved by addition of 17 ml of 1N hydrochloric acid and heating. After cooling in an ice-bath, the precipitate which has separated out is filtered off with suction, washed with ethanol and dried at 100° C. in vacuo.

Yield: 2.7 g (61% of theory)of 8-chloro-1-cyclopropyl-7-(2,8-diazabicyclo[4.3.0]non-8-yl)-6-fluoro-1,4-dihydro-4-oxo-3-quinolinecarboxylic acid hydrochloride, melting point: from 225° C. decomposition.

EXAMPLE 23

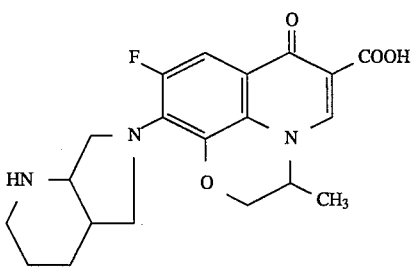

The reaction is carried out analogously to Example 22 with 9,10-difluoro-2,3-dihydro-3-methyl-7-oxo-7H-pyrido-[1,2,3-de][1,4]benzoxazine-6-carboxylic acid and the reaction product obtained is purified by chromatography on silica gel using methylene chloride/methanol/17% strength aqueous ammonia solution (30:8:1) as the mobile phase. 10-(2,8-Diazabicyclo[4.3.0]non-8-yl)-9-fluoro-2,3-dihydro-3-methyl-7-oxo-7H-pyrido[1,2,3-de][1,4]benzoxazine-6-carboxylic acid of melting point 291°–292° C. (with decomposition) is obtained.

EXAMPLE 24

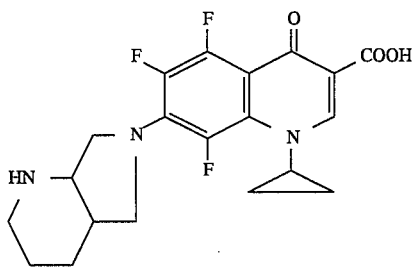

6 g (20 mmol) of 1-cyclopropyl-5,6,7,8-tetrafluoro-1,4-dihydro-4-oxo-3-quinolinecarboxylic acid are heated under reflux in 30 ml of 1-methyl-2-pyrrolidinone and 60 ml of acetonitrile with 2.2 g (20 mmol) of 1,4-diazabicyclo[2.2.2]octane and 2.7 g (21.4 mmol) of 2,8-diazabicyclo[4.3.0]nonane for 1 hour. The mixture is concentrated to a substantial degree in vacuo, the residue is stirred with 200 ml of water and the undissolved crystals are filtered off with suction, washed with water and dried.

Yield: 6.3 g (77.4% of theory) of 1-cyclopropyl-7-(2,8-diazabicyclo[4.3.0]non-8-yl]-5,6,8-trifluoro-1,4-dihydro-4-oxo-3-quinolinecarboxylic acid Melting point: 266°–269° C. (with decomposition); after recrystallization from dimethylformamide: melting point: 272°–273° C. (with decomposition).

EXAMPLE 25

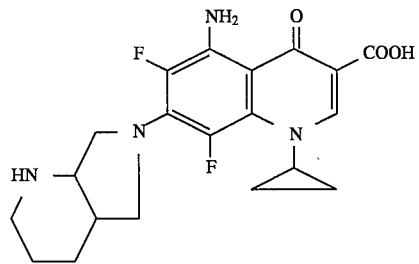

20 ml of saturated ethanolic ammonia solution are added to 4.1 g (10 mmol) of the product from Example 24 in 40 ml of pyridine, and the mixture is heated at 120° C. in an autoclave for 12 hours. The suspension is evaporated, the residue is stirred with water and the pH is brought to 7 with 2N hydrochloric acid. The precipitate which has separated out is filtered off with suction and recrystallized from glycol monomethyl ether.

Yield: 0.7 g (17% of theory) of 5-amino-1-cyclopropyl-7-(2,8-diazabicyclo[4.3.0]non-8-yl)-6,8-difluoro-1,4-dihydro-4-oxo-3-quinolinecarboxylic acid, melting point: 275°–277° C. (with decomposition).

Mass spectrum: m/e 404 ($M^+$), 384 ($M^+$—HF), 290, 249, 96 (100).

EXAMPLE 26

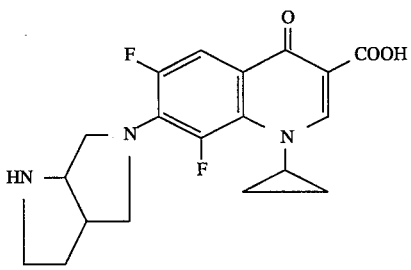

A. Analogously to Example 13, 1-cyclopropyl-7-(2,7-diazabicyclo[3.3.0]oct-7-yl)-6,8-difluoro-1,4-dihydro-4-oxo-3-quinolinecarboxylic acid, melting points 277°–280° (with decomposition), is obtained with 2,7-diazabicyclo[3.3.0]octane.

B. 370 mg of the betaine are dissolved in 13 ml of half-concentrated hydrochloric acid, the solution is concentrated and the residue is treated with 10 ml of ethanol. The undissolved product is filtered off with suction, washed with ethanol and dried.

Yield: 290 mg of 1-cyclopropyl-7-(2,7-diazabicyclo[3.3.0]oct-7-yl)-6,8-difluoro-1,4-dihydro-4-oxo-3-quinolinecarboxylic acid hydrochloride, melting points 269°–271° C. (with decomposition).

EXAMPLE 27

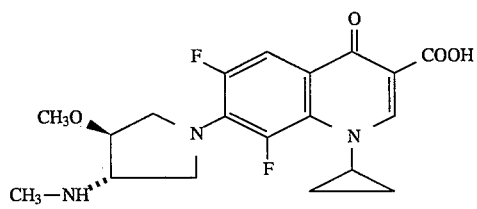

The reaction is carried out analogously to Example 8 with trans-4-methoxy-3-methylamino-pyrrolidine dihydrochloride. 1-Cyclopropyl-6,8-difluoro-1,4-dihydro-7-(trans-4-methoxy-3-methylamino-1-pyrrolidinyl)-4-oxo-3-quinolinecarboxylic acid, melting points 268°–270° C. (with decomposition) is obtained.

EXAMPLE 28

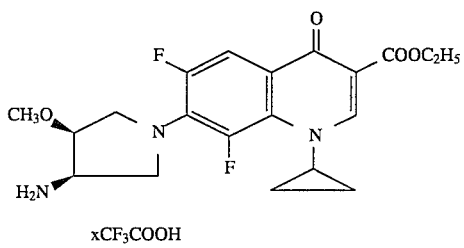

xCF₃COOH

A. 1.4 g (2.9 mmol ) of the product from Example 3 A and 1.98 ml (1.7 g, 12 mmol) of dimethylformamide diethyl acetal are heated at 120° C. in 15 ml of absolute dimethylformamide for 2 hours. The mixture is then concentrated in vacuo. The residue which remains is stirred with acetonitrile. The precipitate is filtered off with suction, washed with a little acetonitrile and dried.

Yield: 0.8 g (54.4% of theory) of ethyl 7-(cis-3-tert.-butoxycarbonylamino-4-methoxy-1-pyrrolidinyl)-1-cyclopropyl-6,8-difluoro-1,4-dihydro-4-oxo-3-quinolinecarboxylate, melting point: 151°–152° C.

B. 0.3 g (0.6 mmol ) of the product from Example 28 A are stirred in 10 ml of trifluoroacetic acid at 20° C. for 10 minutes. The trifluoroacetic acid is then removed in vacuo. The residue solidifies on addition of diethyl ether. The solid is isolated, washed with diethyl ether and dried.

Yield: 0.25 g (80.6% of theory) of ethyl 7-(cis-3-amino-4-methoxy-1-pyrrolidinyl)-1-cyclopropyl-6,8-difluoro-1,4-dihydro-4-oxo-3-quinolinecarboxylate trifluoroacetate Melting point: 124°–126° C.

EXAMPLE 29

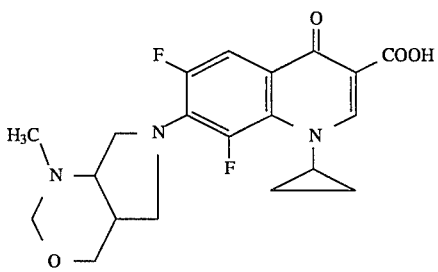

Analogously to Example 13, 1-cyclopropyl-6,8-difluoro-1,4-dihydro-7-(2-methyl-4-oxa-2,8-diazabicyclo[4.3.0]non-8-yl)-4-oxo-3-quinolinecarboxylic acid, melting point 258°–260° C. (with decomposition), is obtained with 2-methyl-4-oxo-2,8-diazabicyclo[4.3.0]nonane.

EXAMPLE 30

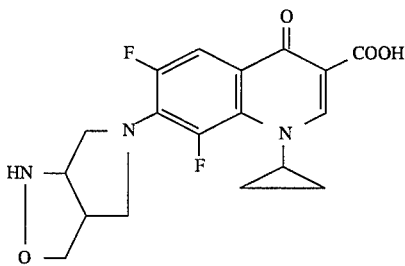

Analogously to Example 19, 1-cyclopropyl-6,8-difluoro-1,4-dihydro-7-(3-oxa-2,7-diazabicyclo[3.3.0]octan-7-yl)-4-oxo-3-quinolinecarboxylic acid is obtained with 3-oxa-2,7-diazabicyclo[3.3.0]octane.

EXAMPLE 31

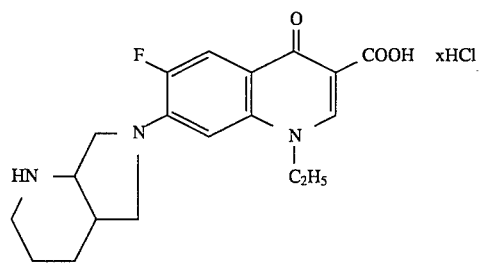

A. 1.1 g (10 mol) of 1,4-diazabicyclo[2.2.2]octane and 1.4 g (11 mmol) of 2,8-diazabicyclo[4.3.0]nonane are added to 2.53 g (10 mmol) of 1-ethyl-6,7-difluoro-1,4-dihydro-4-oxo-3-quinolinecarboxylic acid in 30 ml of acetonitrile and 15 ml of dimethylformamide and the mixture is heated under reflux for 1 hour. The mixture is concentrated, the residue is stirred with water and the precipitate is filtered off with suction, washed with water and dried.

Yield: 3.1 g (86% of theory) of 7-(2,8-diazabicyclo[4.3.0] non-8-yl)-1-ethyl-6-fluoro-4-oxo-3-quinolinecarboxylic acid, melting points 259°–261° C. (with decomposition).

B. 2.9 g (8 mmol) of the betaine from stage A are dissolved in 20 ml of half-concentrated hydrochloric acid under the influence of heat, the solution is filtered hot and the hydrochloride is precipitated from the filtrate by addition of ethanol. This hydrochloride is filtered off with suction, washed with ethanol and dried at 120° C./12 mbar.

Yield: 1.8 g (57% of theory) of 7-(2,8-diazabicyclo[4.3.0] non-8-yl)-1-ethyl-6-fluoro-4-oxo-3-quinolinecarboxylic acid hydrochloride, melting point, with decomposition: 299° C. (dark coloration already starting from about 215° C.).

EXAMPLE 32

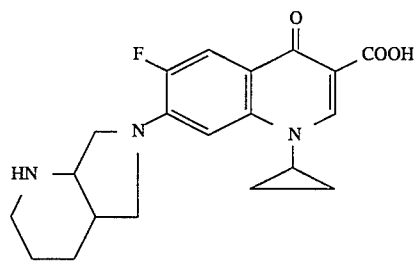

Reaction analogously to Example 31 with 1-cyclopropyl-6,7-difluoro-1,4-dihydro-4-oxo-3-quinolinecarboxylic acid gives:

A. 1-Cyclopropyl-7-(2,8-diazabicyclo[4.3.0]non-8-yl)-6-fluoro-4-oxo-3-quinolinecarboxylic acid, melting point: 249°–257° C. (with decomposition)

B. 1-Cyclopropyl-7-(2,8-diazabicyclo[4.3.0]non-8-yl)-6-fluoro-4-oxo-3-quinolinecarboxylic acid hydrochloride, melting point with decomposition: 320° C. (dark coloration already starting from about 288° C.).

EXAMPLE 33

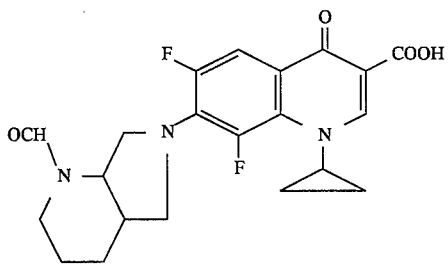

1.1 g (3 mmol) of 1-cyclopropyl-7-(2,8-diazabicyclo[4.3.0]non-8-yl)-6,8-difluoro-1,4-dihydro-4-oxo-3-quinolinecarboxylic acid are heated under reflux in 10 ml of dimethylformamide and 1 ml of formic acid for 4 hours. The mixture is evaporated, the residue is stirred with 4 ml of water and the precipitate is filtered off with suction, dried (crude yield: 1 g, contents 99.5%) and recrystallized from dimethylformamide.

Yield: 0.8 g (64% of theory) of 1-cyclopropyl-6,8-difluoro-7-(2-formyl-2,8-diazabicyclo[4.3.0]non-8-yl)-1,4-dihydro- 4-oxo-3-quinolinecarboxylic acid, melting point: 276°–278° C.

EXAMPLE 34

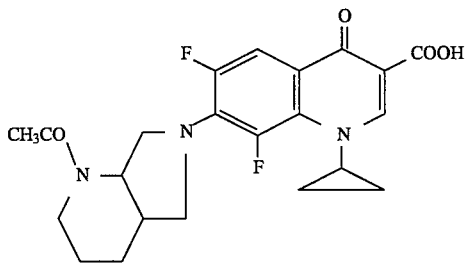

1.1 g (3 mmol ) of 1-cyclopropyl-7-(2,8-diazabicyclo[4.3.0]non-8-yl)-6,8-difluoro-1,4-dihydro-4-oxo-3-quinolinecarboxylic acid are dissolved in a mixture of 8 ml of dioxane and a solution of 120 mg of sodium hydroxide in 1 ml of water, and at the same time 3 ml of 1N sodium hydroxide solution and 260 mg of acetyl chloride are added, while cooling with ice. The mixture is subsequently stirred at room temperature for 2 hours and diluted with 30 ml of water and the precipitate which has separated out is filtered off with suction. The crude product is recrystallized from glycol monomethyl ether.

Yield: 0.6 g (46% of theory) of 7-(2-acetyl-2,8-diazabicyclo[4.3.0]non-8-yl )-1-cyclopropyl-6,8-difluoro-1,4-dihydro-4-oxo-3-quinolinecarboxylic acid, melting points 261°–263° C. (with decomposition)

EXAMPLE 35

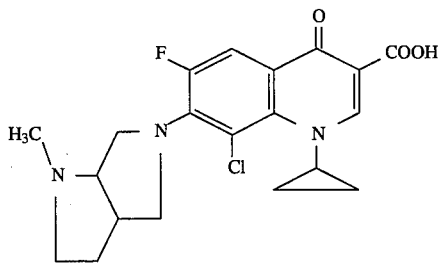

A. Analogously to Example 13, 8-chloro-1-cyclopropyl-6-fluoro-1,4-dihydro-7-(2-methyl-2,7-diazabicyclo[3.3.0]-oct-7-yl)-4-oxo-3-quinolinecarboxylic acid, melting point: 222°–227° C. (with decomposition), is obtained with 8-chloro-1-cyclopropyl-6,7-difluoro-1,4-dihydro-4-oxo-3-quinolinecarboxylic acid and 2-methyl-2,7-diazabicyclo[3.3.0]octane.

B. 2.3 g (5.8 mmol) of the betaine from stage A are dissolved in 15 ml of 1N hydrochloric acid under the influence of heat, the solution is evaporated and the residue is treated with ethanol. The precipitate is filtered off with suction, washed with water and dried.

Yield: 2.2 g (87.7% of theory) of 8-chloro-1-cyclopropyl-6-fluoro-1,4-dihydro-7-(2-methyl-2,7-diazabicyclo[3.3.0]-oct-7-yl)-4-oxo-3-quinolinecarboxylic acid hydrochloride, melting points 303°–305° C. (with decomposition).

EXAMPLE 36

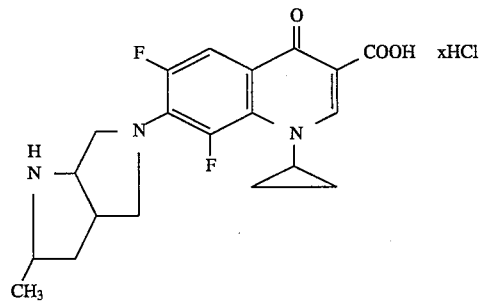

Analogously to Example 13, 1-cyclopropyl-6,8-difluoro-1,4-dihydro-7-(3-methyl-2,7-diazabicyclo[3.3.0]oct-7-yl)-4-oxo-3-quinolinecarboxylic acid is obtained with 3-methyl-2,7-diazabicyclo[3.3.0]octane, and is converted into 1-cyclopropyl-6,8-difluoro-1,4-dihydro-7-(3-methyl-2,7-diazabicyclo[3.3.0]oct-7-yl)-4-oxo-3-quinolinecarboxylic acid hydrochloride, melting point: 216°–221° C. (with decomposition), analogously to Example 15 C with half-concentrated hydrochloric acid.

EXAMPLE 37

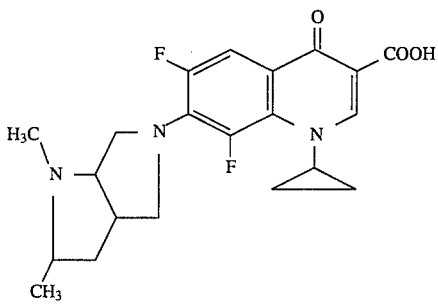

A. A mixture of 1.45 g (5 mmol) of 1-cyclopropyl-6,7,8-trifluoro-1,4-dihydro-4-oxo-3-quinolinecarboxylic acid, 0.85 g (7.5 mmol) of 1,4-diazabicyclo[2.2.2]octane and 0.77 g (5.5 mmol) of 2,3-dimethyl-2,7-diazabicyclo-[3.3.0]octane in 15 ml of acetonitrile and 7.5 ml of dimethylformamide is heated under reflux for 1 hour. After cooling, the precipitate is filtered off with suction, washed with water and recrystallized from glycol monomethyl ether.

Yield: 1 g (47% of theory) of 1-cyclopropyl-7-(2,3-dimethyl-2,7-diazabicyclo[2.2.2]oct-7-yl)-6,8-difluoro-1,4-dihydro-4-oxo-3-quinolinecarboxylic acid, melting point: 208°–209° C. (with decomposition).

B. 0.7 g (1.7 mmol) of the betaine from stage A are dissolved in 6 ml of hot half-concentrated hydrochloric acid and the solution is filtered and concentrated to a substantial degree in vacuo. About 15 ml of ethanol are added, the mixture is cooled in an ice-bath and the salt is filtered off with suction, washed with ethanol and dried at 100° C./1 mbar.

Yield: 0.64 g (84% of theory) of 1-cyclopropyl-7-(2,3-dimethyl-2,7-diazabicyclo[2.2.2]oct-7-yl)-6,8-difluoro-1,4-dihydro-4-oxo-3-quinolinecarboxylic acid hydrochloride, melting point: 233°–236° C. (with decomposition).

EXAMPLE 38

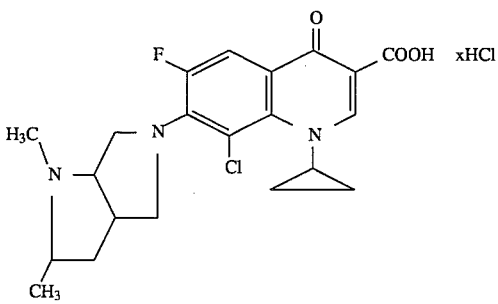

Analogously to Example 37 A and B, 8-chloro-1-cyclopropyl-7-(2,3-dimethyl-2,7-diazabicyclo[2.2.2]oct-7-yl)-6-fluoro-1,4-dihydro-4-oxo-3-quinolinecarboxylic acid hydrochloride, melting point: 240–241° C. (with decomposition), is obtained with 8-chloro-1-cyclopropyl-6,7-difluoro-1,4-dihydro-4-oxo-3-quinolinecarboxylic acid.

EXAMPLE 39

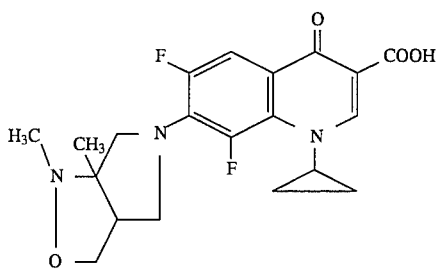

The reaction is carried out analogously to Example 19 with 1,2-dimethyl-3-oxa-2,7-diazabicyclo[3.3.0]octane to give 1-cyclopropyl-6,8-difluoro-1,4-dihydro-7-(1,2-dimethyl-3-oxa-2,7-diazabicyclo[3.3.0]oct-7-yl)-4-oxo-3-quinolinecarboxylic acid of melting point 269°–271° C. (with decomposition).

EXAMPLE 40

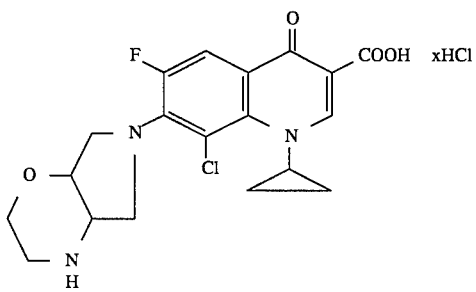

1.45 g (13 mmol) of 1,4-diazabicyclo[2.2.2]octane and 1.23 g (9.6 mmol) of 2-oxa-5,8-diazabicyclo[4.3.0]nonane are added to 2.6 g (8.7 mmol) of 8-chloro-1-cyclopropyl-6,7-difluoro-1,4-dihydro-4-oxo-3-quinolinecarboxylic acid in a mixture of 25 ml of acetonitrile and 12.5 ml of dimethylformamide and the mixture is heated under reflux for 1 hour. It is concentrated, the residue is stirred with water and the undissolved precipitate is filtered off with suction and washed with water. This crude 1-cyclopropyl-8-chloro-6-fluoro-1,4-dihydro-7-(2-oxa-5,8-diazabicyclo[4.3.0]non-8-yl)-4-oxo-3-quinolinecarboxylic acid is introduced into 85.ml of 1N hydrochloric acid, and 6 ml of concentrated hydrochloric acid are added. The hydrochloride which has precipitated out is filtered off with suction, washed with ethanol and dried.

Yield: 3.0 g (77.7% of theory) of 8-chloro-1-cyclopropyl-6-fluoro-1,4-dihydro-7-(2-oxa-5,8-diazabicyclo[4.3.0]non-8-yl)-4-oxo-3-quinolinecarboxylic acid hydrochloride, melting points from 290° C. decomposition.

EXAMPLE 41

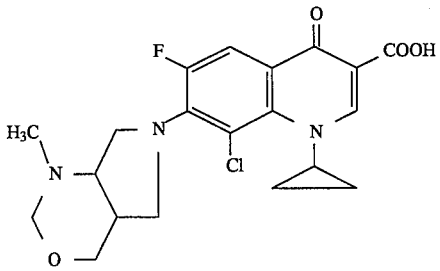

Analogously to Example 13, 8-chloro-1-cyclopropyl-6-fluoro-7-(2-methyl-4-oxa-2,8-diazabicyclo[4.3.0]non-8-yl)-4-oxo-3-quinolinecarboxylic acid, melting point, 202°–203° C. (with decomposition), is obtained with 8-chloro-1-cyclopropyl-6,7-difluoro-1,4-dihydro-4-oxo-3-quinolinecarboxylic acid and 2-methyl-4-oxa-2,8-diazabicyclo[4.3.0]nonane.

FAB mass spectrum: m/e 422 ([M+H]$^+$), 404 (422—H$_2$O).

EXAMPLE 42

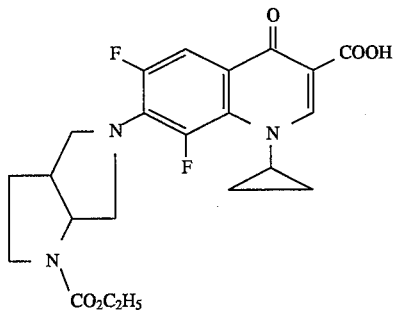

A. The reaction is carried out analogously to Example 13 with ethyl 2,7-diazabicyclo[3.3.0]octane-2-carboxylate to give 1-cyclopropyl-7-(2-ethoxycarbonyl-2,7-diazabicyclo[3.3.0]oct-7-yl)-6,8-difluoro-1,4-dihydro-4-oxo-3-quinolinecarboxylic acid of melting point 191°–192° C.

B. 1.8 g (4 mmol) of the product from Example 42A are heated in 30 ml of concentrated hydrochloric acid under gentle reflux for 15 hours. The solution is concentrated, the residue is stirred with ethanol and the precipitate is filtered off with suction, washed with ethanol and dried at 120° C./12 mbar.

Yield: 1.1 g (67% of theory) of 1-cyclopropyl-7-(2,7-diazabicyclo[3.3.0]oct-7-yl)-6,8-difluoro-1,4-dihydro-4-oxo-3-quinolinecarboxylic acid hydrochloride, melting point: 273°–275° C. (with decomposition). The product is identical to the compound obtained according to Example 26B.

EXAMPLE 43

A. 7.8 g (20 mmol) of 1-cyclopropyl-7-(2,8-diazabicyclo[4.3.0]non-8-yl)-6,8-difluoro-1,4-dihydro-4-oxo-3-quinolinecarboxylic acid are introduced into 175 ml of ethanol, and 2.4 g (25 mmol) of methanesulphonic acid are added at about 70° C. The betaine dissolves, and on cooling the salt precipitates out, this being filtered off with suction, washed with ethanol and dried at 120° C./12 mbar. It is readily soluble in water.

Yield: 8.6 g (88.6% of theory) of 1-cyclopropyl-7-(2,8-diazabicyclo[4.3.0]non-8-yl)-6,8-difluoro-1,4-dihydro-4-oxo-3-quinolinecarboxylic acid mesylate, melting point: 262°–265° C. (with decomposition).

The following compounds are obtained analogously:

B. 1-Cyclopropyl-7-(2,8-diazabicyclo[4.3.0]non-8-yl)-6,8-difluoro-1,4-dihydro-4-oxo-3-quinolinecarboxylic acid tosylate, melting points 248°–250° C. (with decomposition).

C. 1-Cyclopropyl-7-(2,8-diazabicyclo[4.3.0]non-8-yl)-6,8-difluoro-1,4-dihydro-4-oxo-3-quinolinecarboxylic acid lactate, melting points 205° C.–215° C., after sintering beforehand.

EXAMPLE 44

3.9 g (10 mmol) of 1-cyclopropyl-7-(2,8-diazabicyclo [4.3.0]non-8-yl)-6,8-difluoro-1,4-dihydro-4-oxo-3-quinolinecarboxylic acid are suspended in 50 ml of water, and 10 ml of 1N sodium hydroxide solution are added at room temperature, whereupon the product largely dissolves. A slight turbidity is removed by filtration through membrane filter, the filtrate is concentrated under a high vacuum and the residue is stirred with ether, filtered off with suction and dried.

Yield: 3.4 g (82.7% of theory) of sodium 1-cyclopropyl-7-(2,8-diazabicyclo[4.3.0]-non-8-yl)-6,8-difluoro-1,4-dihydro-4-oxo-3-quinolinecarboxylate; the salt decomposes slowly above 210° C. without melting.

EXAMPLE 45

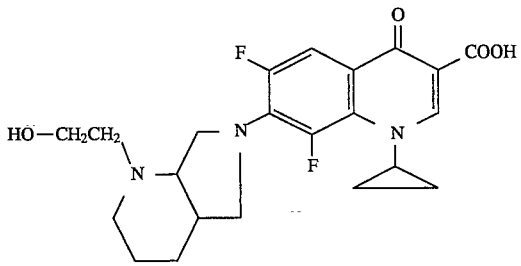

A mixture of 3.9 g (10 mmol) of 1-cyclopropyl-7-(2,8-diazabicyclo [4.3.0]non-8-yl)-6,8-difluoro-1,4-dihydro-4-oxo-3-quinolinecarboxylic acid in 100 ml of dimethylformamide is heated at 80°–100° C. with 4.2 g of triethylamine and 2.8 g of 2-bromoethanol for 20 hours. The solution is then concentrated in vacuo and the residue obtained is purified by chromatography on 200 g of silica gel (mobile phase, CH$_2$Cl$_2$/CH$_3$OH/17% strength NH$_3$=30:8:1). The eluate is concentrated and the residue is stirred with ethanol, filtered off with suction and dried.

Yield: 1.8 g (41.6% of theory) of 1-cyclopropyl-6,8-difluoro-1,4-dihydro-7-[2-(2-hydroxyethyl)-2,8-diazabicyclo[4.3.0]non-8-yl]-4-oxo-3-quinolinecarboxylic acid, melting points 200°–206° C. (with decomposition).

Mass spectrum: m/e 433 (M$^+$), 402 (M$^+$—CH$_2$OH), 140, 110 (100%), 96

EXAMPLE 46

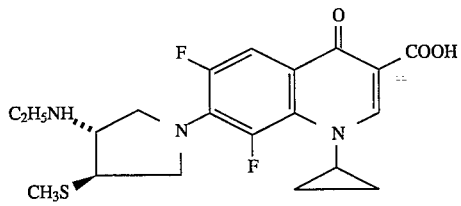

The reaction is carried out analogously to Example 13 with trans-3-ethylamino-4-methylthio-pyrrolidine to give 1-cyclopropyl-7-(trans-3-ethylamino-4-methylthio)-6,8-difluoro-1,4-dihydro-4-oxo-3-quinolinecarboxylic acid, melting points 215°–216° C. (with decomposition).

EXAMPLE 47

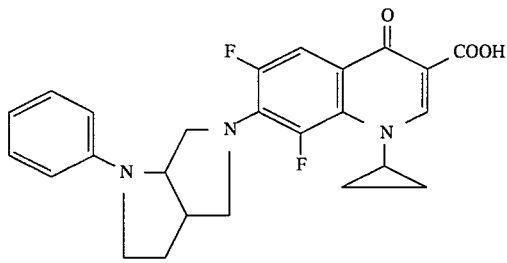

The reaction is carried out analogously to Example 13 with 2-phenyl-2,7-diazabicyclo[3.3.0]octane to give cyclopropyl-6,8-difluoro-1,4-dihydro-4-oxo-7-(2-phenyl-2,7-diazabicyclo[3.3.0]oct-7-yl)-3-quinolinecarboxylic acid, melting point, 259°–260° C. (with decomposition).

EXAMPLE 48

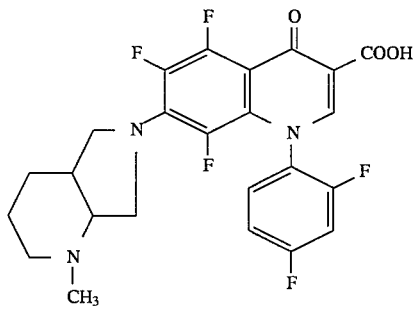

Analogously to Example 13, 5,6,8-trifluoro-1-(2,4-difluorophenyl)-1,4-dihydro-7-(2-methyl-2,8-diazabicyclo[4.3.0]non-8-yl)-4-oxo-3-quinolinecarboxylic acid is obtained with 5,6,7,8-tetrafluoro-1-(2,4-difluorophenyl)-1,4-dihydro-4-oxo-3-quinolinecarboxylic acid.

EXAMPLE 49

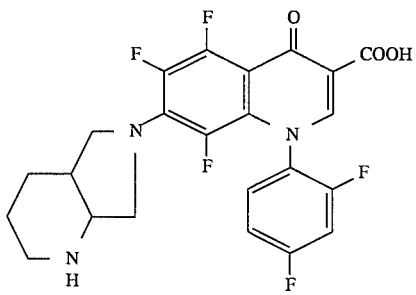

Analogously to Example 24, 7-(2,8-diazabicyclo[4.3.0]non-8-yl)-5,6,8-trifluoro-1-(2,4-difluorophenyl)-1,4-dihydro-4-oxo-3-quinolinecarboxylic acid is obtained with 5,6,7,8-tetrafluoro-1-(2,4-difluorophenyl)-1,4-dihydro-4-oxo-3-quinolinecarboxylic acid.

EXAMPLE 50

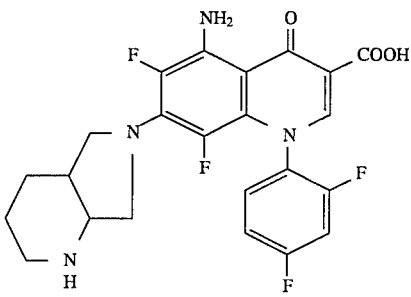

Analogously to Example 25, 5-amino-7-(2,8-diazabicyclo[4.3.0]non-8-yl)-6,8-difluoro-1-(2,4-difluorophenyl)-1,4-dihydro-4-oxo-3-quinolinecarboxylic acid is obtained with 7-(2,8-diazabicyclo[4.3.0]non-8-yl)-5,6,8-trifluoro-1-(2,4-difluorophenyl)-1,4-dihydro-4-oxo-3-quinolinecarboxylic acid.

EXAMPLE 51

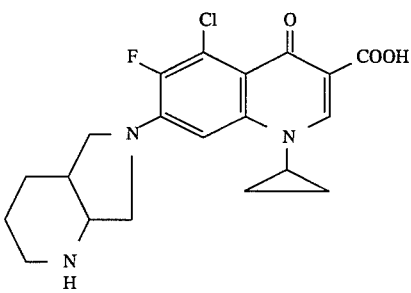

Analogously to Example 15 A, 5-chloro-1-cyclopropyl-7-(2,8-diazabicyclo[4.3.0]non-8-yl)-6-fluoro-1,4-dihydro-4-oxo-3-quinolinecarboxylic acid, melting point: 270° C. (decomposition), is obtained with 5,7-dichloro-1-cyclopropyl-6-fluoro-1,4-dihydro-4-oxo-3-quinolinecarboxylic acid (reflux for 5 hours).

EXAMPLE 52

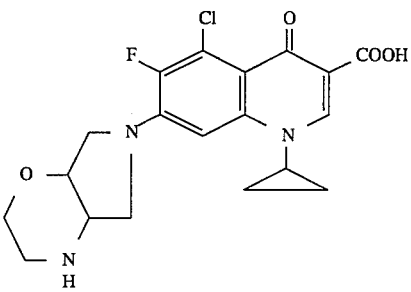

Analogously to Example 8, 5-chloro-1-cyclopropyl-6-fluoro-1,4-dihydro-7-(2-oxa-5,8-diazabicyclo [4.3.0 ]non-8-yl)-4-oxo-3-quinolinecarboxylic acid is obtained with 5,7-dichloro-1-cyclopropyl-6-fluoro-1,4-dihydro-4-oxo-3-quinolinecarboxylic acid (reflux for 5 hours).

EXAMPLE 53

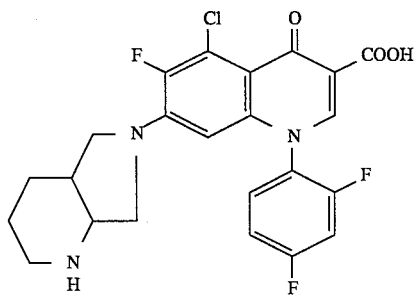

Analogously to Example 15 A, 5-chloro-7-(2,8-diazabicyclo[4.3.0]non-8-yl)-6-fluoro-1-(2,4-difluorophenyl)-1,4-dihydro-4-oxo-3-quinolinecarboxylic acid is obtained with 5,7-dichloro-6-fluoro-1-(2,4-difluorophenyl)-1,4-dihydro-4-oxo-3-quinolinecarboxylic acid (reflux for 5 hours).

EXAMPLE 54

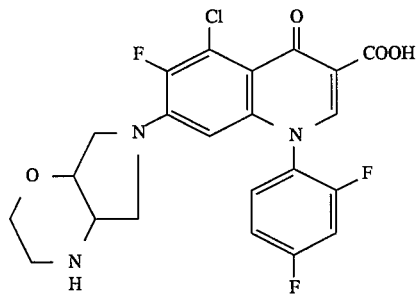

Analogously to Example 8, 5-chloro-6-fluoro-1-(2,4-difluorophenyl)-1,4-dihydro-7-(2-oxa-5,8-diazabicyclo[4.3.0]non-8-yl)-4-oxo-3-quinolinecarboxylic acid is obtained with 5,7-dichloro-6-fluoro-1-(2,4-difluorophenyl)-1,4-dihydro-4-oxo-3-quinolinecarboxylic acid (reflux for 5 hours).

EXAMPLE 55

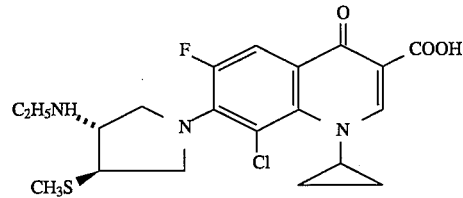

The reaction is carried out analogously to Example 13 with trans-3-ethylamino-4-methylthio-pyrrolidine and 8-chloro-1-cyclopropyl-6,7-difluoro-1,4-dihydro-4-oxo-3-quinolinecarboxylic acid to give 8-chloro-1-cyclopropyl-7-(trans-3-ethylamino-4-methylthio-1-pyrrolidinyl)-6-fluoro-1,4-dihydro-4-oxo-3-quinolinecarboxylic acid, melting points 217°–218° C. (with decomposition).

EXAMPLE 56

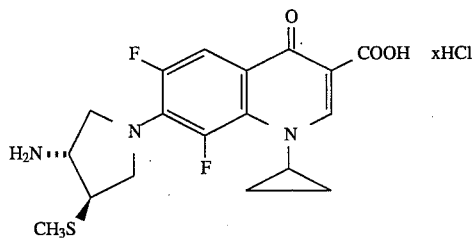

7-(trans-3-Amino-4-methylthio-1-pyrrolidinyl)-1-cyclopropyl-6,8-difluoro-1,4-dihydro-4-oxo-3-quinolinecarboxylic acid, melting point: 208°–211° C. (with decomposition) and 7-(trans-3-amino-4-methylthio-1-pyrrolidinyl)-1-cyclopropyl-6,8-difluoro-1,4-dihydro-4-oxo-3-quinolinecarboxylic acid hydrochloride, melting point: 255°–257° C. (with decomposition), are obtained with trans-3-amino-4-methylthio-pyrrolidine analogously to Examples 13 and 15.

EXAMPLE 57

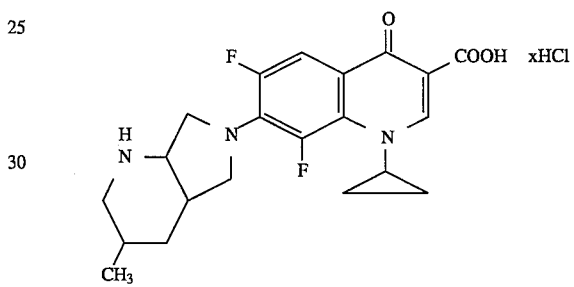

1-Cyclopropyl-6,8-difluoro-1,4-dihydro-7-(4-methyl-2,8-diazabicyclo[4.3.0]non-8-yl)-4-oxo-3-quinolinecarboxylic acid, melting point: 213°–215° C. (with decomposition) (recrystallized from glycol monomethyl ether), and 1-cyclopropyl-6,8-difluoro-1,4-dihydro-7-(4-methyl-2,8-diazabicyclo[4.3.0]non-8-yl)-4-oxo-3-quinolinecarboxylic acid hydrochloride, melting point: 204°–212° C. (with decomposition) are obtained with 4-methyl-2,8-diazabicyclo[4.3.0]-nonane analogously to Examples 13 and 15. The product consists of a mixture of two stereoisomers.

It is understood that the specification and examples are illustrative but not limitative of the present invention and that other embodiments within the spirit and scope of the invention will suggest themselves to those skilled in the art.

We claim:

1. The compound 1-cyclopropyl-7-([S,S]-2,8-diazabicyclo-[4.3.0]non-8-yl)-6-fluoro-1,4-dihydro-8-methoxy-4-oxo-3-quinolinecarboxylic acid having the formula:

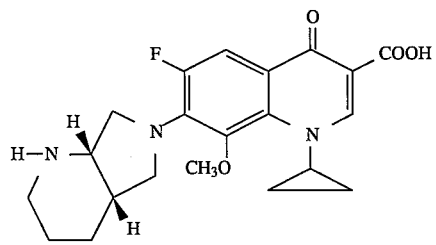

or an alkali metal, alkaline earth metal, silver or guanidinium salt thereof or a pharmaceutically utilizable hydrate or acid addition salt thereof, said compound substantially free of other enantiomers and stereoisomers.

2. The compound (1-cyclopropyl-7-(2,8-diazabicyclo [4.3.0]non-8-yl)-6-fluoro-8-methoxy-1,4-dihydro-4-oxo-3-quinolonecarboxylic acid) of the formula

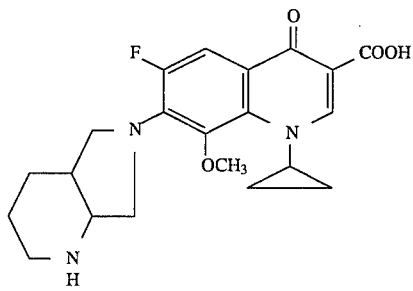

or an addition product thereof with water, an acid or an alkali.

3. An antibacterial composition comprising an antibacterially effective amount of a compound or addition product thereof according to claim 1 and a diluent.

4. An antibacterial composition comprising an antibacterially effective amount of a compound or addition product thereof according to claim 2 and a diluent.

5. A method of combating bacteria in a patient in need thereof which comprises administering to such patient an antibacterially effective amount of a compound or addition product thereof according to claim 1.

6. A method of promoting the growth of an animal which comprises administering to said animal a growth promoting effective amount of a compound or addition product thereof according to claim 1.

7. A method of combating bacteria in a patient in need thereof which comprises administering to such patient an antibacterially effective amount of a compound or addition product thereof according to claim 2.

8. A method of promoting the growth of an animal which comprises administering to said animal a growth promoting effective amount of a compound or addition product thereof according to claim 2.

* * * * *